US012276664B2

(12) United States Patent
Chew et al.

(10) Patent No.: US 12,276,664 B2

(45) Date of Patent: Apr. 15, 2025

(54) METHOD FOR CLASSIFYING CANCER PATIENTS INTO APPROPRIATE HEPATOCELLULAR CARCINOMA TREATMENT GROUPS AND COMPOUNDS FOR TREATING THE PATIENT

(71) Applicant: SINGAPORE HEALTH SERVICES PTE. LTD., Singapore (SG)

(72) Inventors: Suk Peng Chew, Singapore (SG); Salvatore Albani, Singapore (SG); Kah-Hoe Pierce Chow, Singapore (SG); Lu Pan, Singapore (SG)

(73) Assignee: SINGAPORE HEALTH SERVICES PTE. LTD., Singapore (SG)

( * ) Notice: Subject to any disclaimer, the term of this patent is extended or adjusted under 35 U.S.C. 154(b) by 669 days.

(21) Appl. No.: 16/768,001

(22) PCT Filed: Nov. 29, 2018

(86) PCT No.: PCT/SG2018/050585

§ 371 (c)(1),
(2) Date: May 28, 2020

(87) PCT Pub. No.: WO2019/108135

PCT Pub. Date: Jun. 6, 2019

(65) Prior Publication Data

US 2021/0341483 A1 Nov. 4, 2021

(30) Foreign Application Priority Data

Nov. 30, 2017 (SG) ............................ 10201709924T

(51) Int. Cl.
*G01N 33/574* (2006.01)
*A61K 51/12* (2006.01)

(52) U.S. Cl.
CPC ... *G01N 33/57438* (2013.01); *A61K 51/1251* (2013.01); *G01N 33/57492* (2013.01)

(58) Field of Classification Search
CPC ....... G01N 33/57438; G01N 33/57492; G01N 33/5047; G01N 2800/52; A61K 51/1251; A61P 35/00; C07K 16/00
See application file for complete search history.

(56) References Cited

U.S. PATENT DOCUMENTS

| | | | | |
|---|---|---|---|---|
| 2006/0115424 | A1 | 6/2006 | Gray | |
| 2013/0330325 | A1 | 12/2013 | Grabe et al. | |
| 2016/0222118 | A1 | 8/2016 | Chen et al. | |
| 2016/0312295 | A1* | 10/2016 | Ayers | G16B 25/10 |
| 2017/0362320 | A1* | 12/2017 | Sukhatme | A61K 45/06 |

OTHER PUBLICATIONS

Chew et al. (Liver Cancer 6 (suppl. 1): 1-71, published online Jul. 14, 2017).*

Dendy et al. (Oncotarget 8(23): 37912-37922, published Mar. 8, 2017).*

Saad Haider et al. A Copula Based Approach for Design of Multivariate Random Forests for Drug Sensitivity Prediction. PLoS ONE 10(12): 1-22, published: Dec. 10, 2015.*

Chinese Office Action with Search Report dated Dec. 26, 2022 for Chinese Application No. 201880077238.0.

IB Form 373 International Preliminary Report on Patentability Chapter 1 for International Patent Application No. PCT/SG2018/050585.

D'Emic Nicole et al: "Prognostic significance of neutrophil-lymphocyte ratio and platelet-lymphocyte ratio in patients treated with selective internal radiation therapy", Journal of Castrointestinal Oncology, vol. 7, No. 2, Apr. 1, 2016 (Apr. 1, 2016), pp. 269-277, XP055842642, ISSN: 2078-6891, DOI: 10.3978/j.issn.2078-6891.2015.108 *abstract*.

Tohme Samer et al: "Neutrophil-Lymphocyte Ratio is a Simple and Novel Biomarker for Prediction of Survival after Radioembolization for Metastatic Colorectal Cancer", Annals of Surgical Oncology, Raven Press, New York, NY, US, vol. 22, No. 5, Sep. 5, 2014 (Sep. 5, 2014), pp. 1701-1707, XP035444799, ISSN: 1068-9265, DOI: 10.1245/S10434-014-4050-6 [retrieved on Sep. 5, 2014] "abstract".

Extended European Search Report for Application No. 18883026.9, Sep. 2, 2022.

Examination Report dated Sep. 2, 2022 for European Application No. 18883026.9.

Kalbasi Anusha et al: "Clinical experiences of combining immunotherapy and radiation therapy in non-small cell lung cancer: lessons from melanoma", Translational lung Cancer Research, vol. 6, No. 2, Apr. 1, 2007 (Apr. 1, 2007), pp. 169-177, XP055956112, Hong Kong ISSN: 2218-6751, DOI: 10.21037/tlcr.2017.03.03.

Notice of Reasons for Rejection dated Mar. 23, 2023 for Japanese Application No. P2020-526525.

Written Opinion of Intellectual Property Office of Singapore dated Aug. 11, 2022 for SG Application No. 11202003956T.

(Continued)

*Primary Examiner* — Alana Harris Dent

(74) *Attorney, Agent, or Firm* — JCIP; Joseph G. Chu

(57) ABSTRACT

A method for the prognosis of response to treatment for a patient suffering from cancer, the method comprising: measuring the expression of at least one immune marker in a leukocyte sample taken from the patient with cancer; classifying the patient sample into (i) sustainable responders (SR) to selective internal radiation therapy (SIRT) or (ii) transient/non-responders (TR/NR) to (SIRT) based on expression of the at least one immune marker in relation to a predetermined value and treating sustainable responders (SR) to SIRT or SIRT or a composition comprising SIRT and an immunotherapy. In a preferred embodiment, the method is for the prognosis of response to treatment of a Hepatocellular carcinoma (HCC) patient comprising detecting the co-expression of PD-1 or Tim-3 with CCR5; or expression of PD-1, Tim-3, CXCR6, or combinations thereof in a leukocyte sample taken from the patient.

8 Claims, 15 Drawing Sheets

Specification includes a Sequence Listing.

(56) References Cited

OTHER PUBLICATIONS

Examination Report dated May 23, 2023 for European Application No. 18883026.9.

International Search Report and Written Opinion for International Patent Application No. PCT/SG2018/050585, Jan. 25, 2019.

Liao, Y et al., Increased Circulating Th17 Cells after Transarterial Chemoembolization Correlate with Improved Survival in Stage III Hepatocellular Carcinoma: A Prospective Study, PLoS One, Apr. 2, 2013, vol. 8, No. 4, pp. e6044: 1-9 [Retrieved on Jan. 23, 2019] <DOI: 10.1371/JOURNAL.PONE.0060444> Whole Document.

Chun, Y.S. et al., Tu1783 Synergistic Effects of Radioembolization and Ipilimumab in Metastatic Melanoma to the Liver. Gastroenterology, Apr. 2015, vol. 148, No. 4 (Supp. 1), pp. s1181 [Retrieved on Jan. 23, 2019] <DOI: 10.1016/S0016-5085(15)34031-2> Abstract.

Katz, S.C. et al., Abstract CT109:HITM-SIR: Phase Ib trial of CAR-T hepatic artery infusions and selective internal radiation therapy for liver metastases. Cancer Research, Jul. 2017, vol. 77, No. 13 Supp. [Retrieved on Jan. 23, 2019] <DOI: 10.1158/1538-7445.AM2017-CT109>Abstract.

Carpizo, D.R. et al., Pilot Study of Angiogenic Response to Yttrium-90 Radioembolization with Resin Microspheres. J Vasc Interv Radiol, Dec. 20, 2013, vol. 25, No. 2, pp. 297-306.e1 HHS Public Access Author Manuscript [Retrieved on Jan. 23, 2019 from https://www.ncbi.nlm.nih.gov/pmc/articles/PMC5496007/] <DOI: 10.1016/J.JVIR.2013.10.030> Whole document.

Damm, R. et al. Y90 Radioembolization in chemo-refractory metastastic, liver dominant colorectal cancer patients: outcome assessment applying a predictive scoring system. BMC Cancer, Jul. 20, 2016, vol. 16, pp. 509: 1-7 [Retrieved on Jan. 23, 2019] <DOI: 10.1186/S12885-016-2549-X> Whole document.

Dendy, M.S. et al., Predictors and prognosticators for survival with Yttrium-90 radioembolization therapy for unresectable colorectal cancer liver metastasis. Oncotarget, Mar. 8, 2017, vol. 8, No. 23, pp. 37912-37922 [Retrieved on Jan. 23, 2019] <DOI: 10.18632/ONCOTARGET.16007> Whole document.

Danaher, P. et al., Gene expression markers of Tumor Infiltrating Leukocytes. J Immunother Cancer, Feb. 21, 2017, vol. 5, pp. 18: 1-15 [Retrieved on Jan. 23, 2019] <DOI: 10.1186/S40425-017-0215-8> Whole document.

Chew, V. et al., Immune activation underlies a sustained clinical response to Yttrium-90 radioembolisation in hepatocellular carcinoma. Gut, Feb. 13, 2018, vol. 68, No. 2, pp. 335-346 [Retrieved on Jan. 23, 2019] <DOI: 10.1136/GUTJNL-2017-315485> Whole document.

Chew, V. et al., Discovery of Biomarkers for Clinical Response to Radiotherapy in HCC via Deep Immunoprofiling of Peripheral Blood. Liver Cancer, Jul. 6, 2018, vol. 7, No. Supp 1, p. 66 [Retrieved on Jan. 21, 2019] <DOI: 10.1159/000490877> Abstract.

Office Action dated Jul. 13, 2023 for Chinese Application No. 201880077238.0, Text in Chinese.

* cited by examiner

B

C

D

A

B

A

E

A

B

Figure 13 continued C
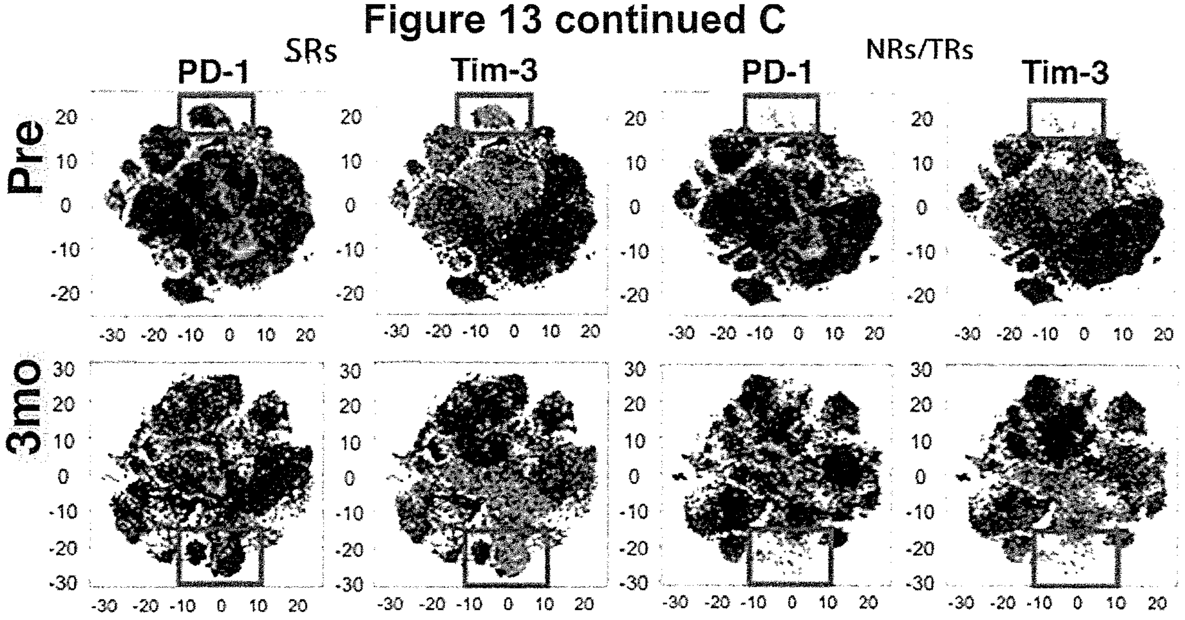
Figure 14
A
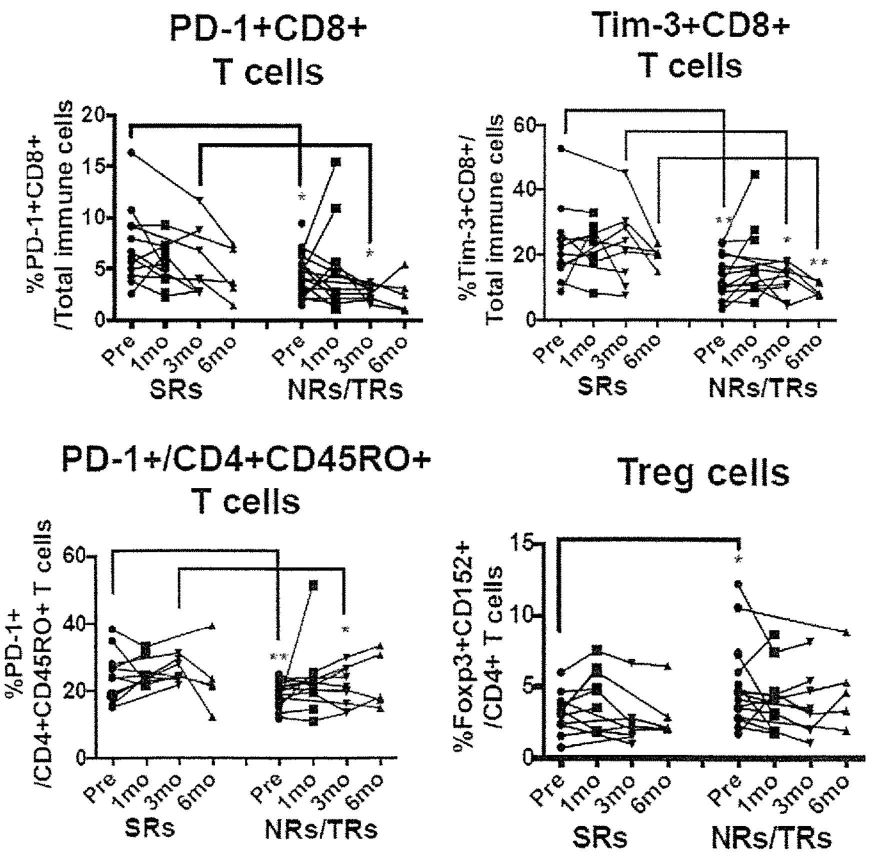

SEQUENCE LISTING

```
<160> NUMBER OF SEQ ID NOS: 42

<210> SEQ ID NO 1
<211> LENGTH: 1540
<212> TYPE: DNA
<213> ORGANISM: Homo sapiens

<400> SEQUENCE: 1

aattctaccc cccttggtgc caacagatga ggttcacaat ctcttccaca aaacatgcag     60
ttaaatatct gaggatattc agggacttgg atttggtggc aggagatcaa cataaaccaa    120
gacaaggaag aagtcaaaga aatgaatcaa aggcagccga agagttcaca agtgtgaagc    180
ctggaagccg gcgggtgccg ctgtgtagga aagaagctaa agcacttcca gagcctgtcc    240
ggagctcaga ggttcggaag acttatcgac catggagcgc gcgtcctgct tgttgctgct    300
gctgctgccg ctggtgcacg tctctgcgac cacgccagaa ccttgtgagc tggacgatga    360
agatttccgc tgcgtctgca acttctccga acctcagccc gactggtccg aagccttcca    420
gtgtgtgtct gcagtagagg tggagatcca tgccggcggt ctcaacctag agccgtttct    480
aaagcgcgtc gatgcggacg ccgacccgcg gcagtatgct gacacggtca aggctctccg    540
cgtgcggcgg ctcacagtgg gagccgcaca ggttcctgct cagctactgg taggcgccct    600
gcgtgtgcta gcgtactccc gcctcaagga actgacgctc gaggacctaa agataaccgg    660
caccatgcct ccgctgcctc tggaagccac aggacttgca ctttccagct tgcgcctacg    720
caacgtgtcg tgggcgacag ggcgttcttg gctcgccgag ctgcagcagt ggctcaagcc    780
aggcctcaag gtactgagca ttgcccaagc acactcgcct gccttttcct gcgaacaggt    840
tcgcgccttc ccggccctta ccagcctaga cctgtctgac aatcctggac tgggcgaacg    900
cggactgatg gcggctctct gtccccacaa gttcccggcc atccagaatc tagcgctgcg    960
caacacagga atggagacgc ccacaggcgt gtgcgccgca ctggcggcgg caggtgtgca   1020
gccccacagc ctagacctca gccacaactc gctgcgcgcc accgtaaacc ctagcgctcc   1080
gagatgcatg tggtccagcg ccctgaactc cctcaatctg tcgttcgctg ggctggaaca   1140
ggtgcctaaa ggactgccag ccaagctcag agtgctcgat ctcagctgca acagactgaa   1200
cagggcgccg cagcctgacg agctgcccga ggtggataac ctgacactgg acgggaatcc   1260
cttcctggtc cctggaactg ccctccccca cgagggctca atgaactccg gcgtggtccc   1320
agcctgtgca cgttcgaccc tgtcggtggg ggtgtcggga accctggtgc tgctccaagg   1380
ggcccggggc tttgcctaag atccaagaca gaataatgaa tggactcaaa ctgccttggc   1440
ttcaggggag tcccgtcagg acgttgagga cttttcgacc aattcaaccc tttgccccac   1500
ctttattaaa atcttaaaca acgggtcaaa aaaaaaaaaa                         1540

<210> SEQ ID NO 2
<211> LENGTH: 1534
<212> TYPE: DNA
```

<213> ORGANISM: Homo sapiens

<400> SEQUENCE: 2

```
tattgtcaga gtcctcttgt ttggccttct aggaaggctg tgggacccag ctttcttcaa     60
ccagtccagg tggaggcctc tgccttgaac gtttccaagt gaggtaaaac ccgcaggccc    120
agaggcctct ctacttcctg tgtggggttc agaaaccctc ctcccctccc agcctcaggt    180
gcctgcttca gaaaatgaag tagtaagtct gctggcctcc gccatcttag taaagtaaca    240
gtcccatgaa acaaagatgc agtcgggcac tcactggaga gttctgggcc tctgcctctt    300
atcagttggc gtttgggggc aagatggtaa tgaagaaatg ggtggtatta cacagacacc    360
atataaagtc tccatctctg gaaccacagt aatattgaca tgccctcagt atcctggatc    420
tgaaatacta tggcaacaca atgataaaaa cataggcggt gatgaggatg ataaaaacat    480
aggcagtgat gaggatcacc tgtcactgaa ggaattttca gaattggagc aaagtggtta    540
ttatgtctgc taccccagag gaagcaaacc agaagatgcg aacttttatc tctacctgag    600
ggcaagagtg tgtgagaact gcatggagat ggatgtgatg tcggtggcca caattgtcat    660
agtggacatc tgcatcactg gggcttgct gctgctggtt tactactgga gcaagaatag    720
aaaggccaag gccaagcctg tgacacgagg agcgggtgct ggcggcaggc aaaggggaca    780
aaacaaggag aggccaccac ctgttcccaa cccagactat gagcccatcc ggaaaggcca    840
gcgggacctg tattctggcc tgaatcagag acgcatctga ccctctggag aacactgcct    900
cccgctggcc caggtctcct ctccagtccc cctgcgactc cctgtttcct gggctagtct    960
tggaccccac gagagagaat cgttcctcag cctcatggtg aactcgcgcc ctccagcctg   1020
atcccccgct ccctcctccc tgccttctct gctggtaccc agtcctaaaa tattgctgct   1080
tcctcttcct ttgaagcatc atcagtagtc acaccctcac agctggcctg ccctcttgcc   1140
aggatattta tttgtgctat tcactccctt ccctttggat gtaacttctc cgttcagttc   1200
cctccttttc ttgcatgtaa gttgtccccc atcccaaagt attccatcta cttttctatc   1260
gccgtcccct tttgcagccc tctctgggga tggactgggt aaatgttgac agaggccctg   1320
ccccgttcac agatcctggc cctgagccag ccctgtgctc ctccctcccc caacactccc   1380
taccaacccc ctaatcccct actccctcca cccccctcc actgtaggcc actggatggt   1440
catttgcatc tccgtaaatg tgctctgctc ctcagctgag agagaaaaaa ataaactgta   1500
tttggctgca agaaaaaaaa aaaaaaaaaa aaaa                                1534
```

<210> SEQ ID NO 3
<211> LENGTH: 1968
<212> TYPE: DNA
<213> ORGANISM: Homo sapiens

<400> SEQUENCE: 3

```
aggcccctgc ctgccccagc atcccctgcg cgaagctggg tgccccggag agtctgacca     60
ccatgccacc tcctcgcctc ctcttcttcc tcctcttcct cacccccatg gaagtcaggc    120
ccgaggaacc tctagtggtg aaggtggaag agggagataa cgctgtgctg cagtgcctca    180
aggggacctc agatggcccc actcagcagc tgacctggtc tcgggagtcc ccgcttaaac    240
ccttcttaaa actcagcctg gggctgccag gcctgggaat ccacatgagg cccctggcca    300
tctggctttt catcttcaac gtctctcaac agatgggggg cttctacctg tgccagccgg    360
ggcccccctc tgagaaggcc tggcagcctg gctggacagt caatgtggag ggcagcgggg    420
agctgttccg gtggaatgtt tcggacctag gtggcctggg ctgtggcctg aagaacaggt    480
```

-continued

```
cctcagaggg ccccagctcc ccttccggga agctcatgag ccccaagctg tatgtgtggg    540

ccaaagaccg ccctgagatc tgggagggag agcctccgtg tctcccaccg agggacagcc    600

tgaaccagag cctcagccag gacctcacca tggcccctgg ctccacactc tggctgtcct    660

gtggggtacc ccctgactct gtgtccaggg gccccctctc ctggacccat gtgcacccca    720

aggggcctaa gtcattgctg agcctagagc tgaaggacga tcgcccggcc agagatatgt    780

gggtaatgga gacgggtctg ttgttgcccc gggccacagc tcaagacgct ggaaagtatt    840

attgtcaccg tggcaacctg accatgtcat tccacctgga gatcactgct cggccagtac    900

tatggcactg gctgctgagg actggtggct ggaaggtctc agctgtgact ttggcttatc    960

tgatcttctg cctgtgttcc cttgtgggca ttcttcatct tcaaagagcc ctggtcctga   1020

ggaggaaaag aaagcgaatg actgacccca ccaggagatt cttcaaagtg acgcctcccc   1080

caggaagcgg gccccagaac cagtacggga acgtgctgtc tctccccaca cccacctcag   1140

gcctcggacg cgcccagcgt tggccgcag gcctgggggg cactgccccg tcttatggaa   1200

acccgagcag cgacgtccag gcggatggag ccttggggtc ccggagcccg ccgggagtgg   1260

gcccagaaga agaggaaggg gagggctatg aggaacctga cagtgaggag gactccgagt   1320

tctatgagaa cgactccaac cttgggcagg accagctctc ccaggatggc agcggctacg   1380

agaaccctga ggatgagccc ctgggtcctg aggatgaaga ctccttctcc aacgctgagt   1440

cttatgagaa cgaggatgaa gagctgaccc agccggtcgc caggacaatg gacttcctga   1500

gccctcatgg gtcagcctgg gaccccagcc gggaagcaac ctccctggca gggtcccagt   1560

cctatgagga tatgagagga atcctgtatg cagcccccca gctccgctcc attcggggcc   1620

agcctggacc caatcatgag gaagatgcag actcttatga gaacatggat aatcccgatg   1680

ggccagaccc agcctgggga ggagggggcc gcatgggcac ctggagcacc aggtgatcct   1740

caggtggcca gcctggatct cctcaagtcc ccaagattca cacctgactc tgaaatctga   1800

agacctcgag cagatgatgc caacctctgg agcaatgttg cttaggatgt gtgcatgtgt   1860

gtaagtgtgt gtgtgtgtgt gtgtgtgtat acatgccagt gacacttcca gtcccctttg   1920

tattccttaa ataaactcaa tgagctcttc caatcctaaa aaaaaaaa                 1968


<210> SEQ ID NO 4
<211> LENGTH: 4946
<212> TYPE: DNA
<213> ORGANISM: Homo sapiens

<400> SEQUENCE: 4

agaacaactt ttttgacttc ctgcaaagag gacccttaca gtatttttgg agaagttagt     60

aaaaccgaat ctgacatcat cacctagcag ttcatgcagc tagcaagtgg tttgttctta    120

gggtaacaga ggaggaaatt gttcctcgtc tgataagaca acagtggaga aaggacgcat    180

gctgtttctt agggacacgg ctgacttcca gatatgacca tgtatttgtg gcttaaactc    240

ttggcatttg gctttgcctt tctggacaca gaagtatttg tgacagggca aagcccaaca    300

ccttccccca ctgatgccta ccttaatgcc tctgaaacaa ccactctgag cccttctgga    360

agcgctgtca tttcaaccac aacaatagct actactccat ctaagccaac atgtgatgaa    420

aaatatgcaa acatcactgt ggattactta tataacaagg aaactaaatt atttacagca    480

aagctaaatg ttaatgagaa tgtggaatgt ggaaacaata cttgcacaaa caatgaggtg    540

cataacctta cagaatgtaa aaatgcgtct gtttccatat ctcataattc atgtactgct    600
```

-continued

```
cctgataaga cattaatatt agatgtgcca ccaggggttg aaaagtttca gttacatgat    660
tgtacacaag ttgaaaaagc agatactact atttgtttaa aatggaaaaa tattgaaacc    720
tttacttgtg atacacagaa tattacctac agatttcagt gtggtaatat gatatttgat    780
aataaagaaa ttaaattaga aaaccttgaa cccgaacatg agtataagtg tgactcagaa    840
atactctata ataaccacaa gtttactaac gcaagtaaaa ttattaaaac agattttggg    900
agtccaggag agcctcagat tattttttgt agaagtgaag ctgcacatca aggagtaatt    960
acctggaatc cccctcaaag atcatttcat aattttaccc tctgttatat aaaagagaca   1020
gaaaaagatt gcctcaatct ggataaaaac ctgatcaaat atgatttgca aaatttaaaa   1080
ccttatacga aatatgtttt atcattacat gcctacatca ttgcaaaagt gcaacgtaat   1140
ggaagtgctg caatgtgtca tttcacaact aaaagtgctc ctccaagcca ggtctggaac   1200
atgactgtct ccatgacatc agataatagt atgcatgtca agtgtaggcc tcccagggac   1260
cgtaatggcc cccatgaacg ttaccatttg gaagttgaag ctggaaatac tctggttaga   1320
aatgagtcgc ataagaattg cgatttccgt gtaaaagatc ttcaatattc aacagactac   1380
acttttaagg cctattttca caatggagac tatcctggag aacccttat tttacatcat   1440
tcaacatctt ataattctaa ggcactgata gcatttctgg catttctgat tattgtgaca   1500
tcaatagccc tgcttgttgt tctctacaaa atctatgatc tacataagaa aagatcctgc   1560
aatttagatg aacagcagga gcttgttgaa agggatgatg aaaaacaact gatgaatgtg   1620
gagccaatcc atgcagatat tttgttggaa acttataaga ggaagattgc tgatgaagga   1680
agactttttc tggctgaatt tcagagcatc ccgcgggtgt tcagcaagtt tcctataaag   1740
gaagctcgaa agccctttaa ccagaataaa aaccgttatg ttgacattct tccttatgat   1800
tataaccgtg ttgaactctc tgagataaac ggagatgcag ggtcaaacta cataaatgcc   1860
agctatattg atggtttcaa agaacccagg aaatacattg ctgcacaagg tcccagggat   1920
gaaactgttg atgatttctg gaggatgatt tgggaacaga aagccacagt tattgtcatg   1980
gtcactcgat gtgaagaagg aaacaggaac aagtgtgcag aatactggcc gtcaatggaa   2040
gagggcactc gggcttttgg agatgttgtt gtaaagatca accagcacaa aagatgtcca   2100
gattacatca ttcagaaatt gaacattgta aataaaaaag aaaaagcaac tggaagagag   2160
gtgactcaca ttcagttcac cagctggcca gaccacgggg tgcctgagga tcctcacttg   2220
ctcctcaaac tgagaaggag agtgaatgcc ttcagcaatt tcttcagtgg tcccattgtg   2280
gtgcactgca gtgctggtgt tgggcgcaca ggaacctata tcggaattga tgccatgcta   2340
gaaggcctgg aagccgagaa caaagtggat gtttatggtt atgttgtcaa gctaaggcga   2400
cagagatgcc tgatggttca agtagaggcc cagtacatct tgatccatca ggctttggtg   2460
gaatacaatc agtttggaga aacagaagtg aatttgtctg aattacatcc atatctacat   2520
aacatgaaga aaagggatcc acccagtgag ccgtctccac tagaggctga attccagaga   2580
cttccttcat ataggagctg gaggacacag cacattggaa atcaagaaga aaataaaagt   2640
aaaaacagga attctaatgt catcccatat gactataaca gagtgccact taaacatgag   2700
ctggaaatga gtaaagagag tgagcatgat tcagatgaat cctctgatga tgacagtgat   2760
tcagaggaac caagcaaata catcaatgca tcttttataa tgagctactg gaaacctgaa   2820
gtgatgattg ctgctcaggg accactgaag gagaccattg gtgacttttg gcagatgatc   2880
ttccaaagaa aagtcaaagt tattgttatg ctgacagaac tgaaacatgg agaccaggaa   2940
atctgtgctc agtactgggg agaaggaaag caaacatatg gagatattga agttgacctg   3000
```

-continued

```
aaagacacag acaaatcttc aacttatacc cttcgtgtct ttgaactgag acattccaag   3060

aggaaagact ctcgaactgt gtaccagtac caatatacaa actggagtgt ggagcagctt   3120

cctgcagaac ccaaggaatt aatctctatg attcaggtcg tcaaacaaaa acttccccag   3180

aagaattcct ctgaagggaa caagcatcac aagagtacac ctctactcat tcactgcagg   3240

gatggatctc agcaaacggg aatattttgt gctttgttaa atctcttaga aagtgcggaa   3300

acagaagagg tagtggatat ttttcaagtg gtaaaagctc tacgcaaagc taggccaggc   3360

atggtttcca cattcgagca atatcaattc ctatatgacg tcattgccag cacctaccct   3420

gctcagaatg gacaagtaaa gaaaaacaac catcaagaag ataaaattga atttgataat   3480

gaagtggaca aagtaaagca ggatgctaat tgtgttaatc cacttggtgc cccagaaaag   3540

ctccctgaag caaaggaaca ggctgaaggt tctgaaccca cgagtggcac tgaggggcca   3600

gaacattctg tcaatggtcc tgcaagtcca gctttaaatc aaggttcata ggaaaagaca   3660

taaatgagga aactccaaac ctcctgttag ctgttatttc tatttttgta gaagtaggaa   3720

gtgaaaatag gtatacagtg gattaattaa atgcagcgaa ccaatatttg tagaagggtt   3780

atattttact actgtggaaa aatatttaag atagttttgc cagaacagtt tgtacagacg   3840

tatgcttatt ttaaaatttt atctcttatt cagtaaaaaa caacttcttt gtaatcgtta   3900

tgtgtgtata tgtatgtgtg tatgggtgtg tgtttgtgtg agagacagag aaagagagag   3960

aattctttca agtgaatcta aaagcttttg cttttccttt gtttttatga agaaaaaata   4020

cattttatat tagaagtgtt aacttagctt gaaggatctg tttttaaaaa tcataaactg   4080

tgtgcagact caataaaatc atgtacattt ctgaaatgac ctcaagatgt cctccttgtt   4140

ctactcatat atatctatct tatatagttt actattttac ttctagagat agtacataaa   4200

ggtggtatgt gtgtgtatgc tactacaaaa aagttgttaa ctaaattaac attgggaaat   4260

cttatattcc atatattagc atttagtcca atgtcttttt aagcttattt aattaaaaaa   4320

tttccagtga gcttatcatg ctgtctttac atggggtttt caattttgca tgctcgatta   4380

ttccctgtac aatatttaaa atttattgct tgatactttt gacaacaaat taggttttgt   4440

acaattgaac ttaaataaat gtcattaaaa taaataaatg caatatgtat taatattcat   4500

tgtataaaaa tagaagaata caaacatatt tgttaaatat ttacatatga aatttaatat   4560

agctattttt atggaatttt tcattgatat gaaaaatatg atattgcata tgcatagttc   4620

ccatgttaaa tcccattcat aactttcatt aaagcattta ctttgaattt ctccaatgct   4680

tagaatgttt ttaccaggaa tggatgtcgc taatcataat aaaattcaac cattattttt   4740

ttcttgttta taatacattg tgttatatgt tcaaatatga aatgtgtatg cacctattga   4800

aatatgttta atgcatttat taacatttgc aggacacttt tacaggcccc aattatccaa   4860

tagtctaata attgtttaag atctagaaaa aaaaaatcaa gaatagtggt atttttcatg   4920

aagtaataaa aactcgtttt ggtgaa                                        4946
```

<210> SEQ ID NO 5
<211> LENGTH: 1312
<212> TYPE: DNA
<213> ORGANISM: Homo sapiens

<400> SEQUENCE: 5

```
ttttaatggt cagactctat tacaccccac attctctttt cttttattct tgtctgttct     60

gcctcactcc cgagctctac tgactcccaa cagagcgccc aagaagaaaa tggccataag    120
```

-continued tggagtccct gtgctaggat ttttcatcat agctgtgctg atgagcgctc aggaatcatg 180
ggctatcaaa gaagaacatg tgatcatcca ggccgagttc tatctgaatc ctgaccaatc 240
aggcgagttt atgtttgact ttgatggtga tgagattttc catgtggata tggcaaagaa 300
ggagacggtc tggcggcttg aagaatttgg acgatttgcc agctttgagg ctcaaggtgc 360
attggccaac atagctgtgg acaaagccaa cctggaaatc atgacaaagc gctccaacta 420
tactccgatc accaatgtac ctccagaggt aactgtgctc acaaacagcc ctgtggaact 480
gagagagccc aacgtcctca tctgtttcat agacaagttc accccaccag tggtcaatgt 540
cacgtggctt cgaaatggaa aacctgtcac cacaggagtg tcagagacag tcttcctgcc 600
cagggaagac caccttttcc gcaagttcca ctatctcccc ttcctgccct caactgagga 660
cgtttacgac tgcagggtgg agcactgggg cttggatgag cctcttctca agcactggga 720
gtttgatgct ccaagccctc tcccagagac tacagagaac gtggtgtgtg ccctgggcct 780
gactgtgggt ctggtgggca tcattattgg gaccatcttc atcatcaagg gattgcgcaa 840
aagcaatgca gcagaacgca gggggcctct gtaaggcaca tggaggtgat ggtgtttctt 900
agagagaaga tcactgaaga aacttctgct ttaatggctt tacaaagctg gcaatattac 960
aatccttgac ctcagtgaaa gcagtcatct tcagcatttt ccagccctat agccacccca 1020
agtgtggata tgcctcttcg attgctccgt actctaacat ctagctggct tccctgtcta 1080
ttgccttttc ctgtatctat tttcctctat ttcctatcat tttattatca ccatgcaatg 1140
cctctggaat aaaacataca ggagtctgtc tctgctatgg aatgccccat ggggcatctc 1200
ttgtgtactt attgtttaag gtttcctcaa actgtgattt ttctgaacac aataaactat 1260
tttgatgatc ttgggtggaa aaaaaaaaaa aaaaaaaaaa aaaaaaaaaa aa 1312

<210> SEQ ID NO 6
<211> LENGTH: 2621
<212> TYPE: DNA
<213> ORGANISM: Homo sapiens

<400> SEQUENCE: 6
agcacccaag ggctggtcaa ccaagctggg ggttgaattt ccatccagca atgcaggcca 60
tgggaggctg cagcagtgac gctgtcagat ccccttttgtg agaataataa tttttataac 120
aacgtggctg gaggactgat caggagagag actggtgtga attgaaggct gttgcaatgg 180
ctccaagaag agatgaggct gtgtgttttc agctgccccc agttgcctgg ccaggctgcc 240
tcgacggccc tattcacggg ccccagcctc ctcgccgggc tggaaggcga caaccgcgaa 300
aaggagggtg actctcctcg gcgggggctt cgggtgacat cacatcctcc aaatgcgaaa 360
tcaggctccg ggccggccga agggcgcaac tttcccccct cggcgcccca ccggctcccg 420
cgcgcctccc ctcgcgcccg agcttcgagc caagcagcgt cctggggagc gcgtcatggc 480
cttaccagtg accgccttgc tcctgccgct ggccttgctg ctccacgccg ccaggccgag 540
ccagttccgg gtgtcgccgc tggatcggac ctggaacctg ggcgagacag tggagctgaa 600
gtgccaggtg ctgctgtcca acccgacgtc gggctgctcg tggctcttcc agccgcgcgg 660
cgccgccgcc agtcccacct tcctcctata cctctcccaa aacaagccca aggcggccga 720
ggggctggac acccagcggt tctcgggcaa gaggttgggg gacaccttcg tcctcaccct 780
gagcgacttc cgccgagaga acgagggcta ctatttctgc tcggccctga gcaactccat 840
catgtacttc agccacttcg tgccggtctt cctgccagcg aagcccacca cgacgccagc 900
gccgcgacca ccaacaccgg cgcccaccat cgcgtcgcag cccctgtccc tgcgcccaga 960
ggcgtgccgg ccagcggcgg ggggcgcagt gcacacgagg gggctggact tcgcctgtga 1020
tatctacatc tgggcgccct tggccgggac ttgtggggtc cttctcctgt cactggttat 1080 cacccttac tgcaaccaca ggaaccgaag acgtgtttgc aaatgtcccc ggcctgtggt 1140
caaatcggga gacaagccca gcctttcggc gagatacgtc taaccctgtg caacagccac 1200
tacattactt caaactgaga tccttccttt tgagggagca agtccttccc tttcattttt 1260
tccagtcttc ctccctgtgt attcattctc atgattatta ttttagtggg ggcggggtgg 1320
gaaagattac tttttcttta tgtgtttgac gggaaacaaa actaggtaaa atctacagta 1380
caccacaagg gtcacaatac tgttgtgcgc acatcgcggt agggcgtgga aaggggcagg 1440
ccagagctac ccgcagagtt ctcagaatca tgctgagaga gctggaggca cccatgccat 1500
ctcaacctct tccccgcccg ttttacaaag gggaggcta aagcccagag acagcttgat 1560
caaaggcaca cagcaagtca gggttggagc agtagctgga gggaccttgt ctcccagctc 1620
agggctcttt cctccacacc attcaggtct ttctttccga ggcccctgtc tcagggtgag 1680
gtgcttgagt ctccaacggc aagggaacaa gtacttcttg atacctggga tactgtgccc 1740
agagcctcga ggaggtaatg aattaaagaa gagaactgcc tttggcagag ttctataatg 1800
taaacaatat cagacttttt tttttataa tcaagcctaa aattgtatag acctaaaata 1860
aaatgaagtg gtgagcttaa ccctggaaaa tgaatccctc tatctctaaa gaaaatctct 1920
gtgaaacccc tatgtggagg cggaattgct ctcccagccc ttgcattgca gaggggccca 1980
tgaaagagga caggctaccc ctttacaaat agaatttgag catcagtgag gttaaactaa 2040
ggccctcttg aatctctgaa tttgagatac aaacatgttc ctgggatcac tgatgacttt 2100
ttatactttg taaagacaat tgttggagag cccctcacac agccctggcc tctgctcaac 2160
tagcagatac agggatgagg cagacctgac tctcttaagg aggctgagag cccaaactgc 2220
tgtcccaaac atgcacttcc ttgcttaagg tatggtacaa gcaatgcctg cccattggag 2280
agaaaaaact taagtagata aggaaataag aaccactcat aattcttcac cttaggaata 2340
atctcctgtt aatatggtgt acattcttcc tgattatttt ctacacatac atgtaaaata 2400
tgtctttctt ttttaaatag ggttgtacta tgctgttatg agtggcttta atgaataaac 2460
atttgtagca tcctctttaa tgggtaaaca gcatccgaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa a 2621

<210> SEQ ID NO 7
<211> LENGTH: 2589
<212> TYPE: DNA
<213> ORGANISM: Homo sapiens

<400> SEQUENCE: 7
cggcccgctg gagaggaagc ccgagagctg ccgcgcgcct gccggacgag ggcgtagaag 60
ccaggcgtca gagcccgggc tccggtgggg tcccccaccc ggccctcggg tcccccgccc 120
cctgctccct gcccatccca gcccacgcga ccctctcgcg cgcggagggg cgggtcctcg 180
acggctacgg gaaggtgcca gcccgccccg gatgggcatc gtggagccgg gttgcggaga 240
catgctgacg ggcaccgagc cgatgccggg gagcgacgag ggccgggcgc ctggcgccga 300
cccgcagcac cgctacttct acccggagcc gggcgcgcag gacgcggacg agcgtcgcgg 360
gggcggcagc ctggggtctc cctacccggg gggcgccttg gtgcccgccc cgccgagccg 420

-continued

```
cttccttgga gcctacgcct acccgccgcg accccaggcg gccggcttcc ccggcgcggg    480
cgagtccttc ccgccgcccg cggacgccga gggctaccag ccgggcgagg gctacgccgc    540
cccggacccg cgcgccgggc tctacccggg gccgcgtgag gactacgcgc tacccgcggg    600
actggaggtg tcggggaaac tgagggtcgc gctcaacaac cacctgttgt ggtccaagtt    660
taatcagcac cagacagaga tgatcatcac caagcaggga cggcggatgt tcccattcct    720
gtcatttact gtggccgggc tggagcccac cagccactac aggatgtttg tggacgtggt    780
cttggtggac cagcaccact ggcggtacca gagcggcaag tgggtgcagt gtggaaaggc    840
cgagggcagc atgccaggaa accgcctgta cgtccacccg gactccccca acacaggagc    900
gcactggatg cgccaggaag tttcatttgg gaaactaaag ctcacaaaca acaagggggc    960
gtccaacaat gtgacccaga tgattgtgct ccagtccctc cataagtacc agccccggct   1020
gcatatcgtt gaggtgaacg acggagagcc agaggcagcc tgcaacgctt ccaacacgca   1080
tatctttact ttccaagaaa cccagttcat tgccgtgact gcctaccaga atgccgagat   1140
tactcagctg aaaattgata ataacccctt tgccaaagga ttccgggaga actttgagtc   1200
catgtacaca tctgttgaca ccagcatccc ctccccgcct ggacccaact gtcaattcct   1260
tgggggagat cactactctc ctctcctacc caaccagtat cctgttccca gccgcttcta   1320
ccccgacctt cctggccagg cgaaggatgt ggttccccag gcttactggc tgggggcccc   1380
ccgggaccac agctatgagg ctgagtttcg agcagtcagc atgaagcctg cattcttgcc   1440
ctctgcccct gggcccacca tgtcctacta ccgaggccag gaggtcctgg cacctggagc   1500
tggctggcct gtggcacccc agtaccctcc caagatgggc ccggccagct ggttccgccc   1560
tatgcggact ctgcccatgg aacccggccc tggaggctca gagggacggg gaccagagga   1620
ccagggtccc cccttggtgt ggactgagat tgcccccatc cggccggaat ccagtgattc   1680
aggactgggc gaaggagact ctaagaggag gcgcgtgtcc ccctatcctt ccagtggtga   1740
cagctcctcc cctgctgggg ccccttctcc ttttgataag gaagctgaag gacagtttta   1800
taactatttt cccaactgag cagatgacat gatgaaagga acagaaacag tgttattagg   1860
ttggaggaca ccgactaatt tgggaaacgg atgaaggact gagaaggccc ccgctccctc   1920
tggcccttct ctgtttagta gttggttggg gaagtggggc tcaagaagga ttttggggtt   1980
caccagatgc ttcctggccc acgatgaaac ctgagagggg tgtccccttg ccccatcctc   2040
tgccctaact acagtcgttt acctggtgct gcgtcttgct tttggtttcc agctggagaa   2100
aagaagacaa gaaagtcttg ggcatgaagg agctttttgc atctagtggg tgggaggggt   2160
caggtgtggg acatgggagc aggagactcc actttcttcc tttgtacagt aactttcaac   2220
cttttcgttg gcatgtgtgt taatccctga tccaaaaaga acaaatacac gtatgttata   2280
accatcagcc cgccagggtc agggaaagga ctcacctgac tttggacagc tggcctgggc   2340
tccccctgct caaacacagt ggggatcaga gaaaaggggc tggaaagggg ggaatggccc   2400
acatctcaag aagcaagata ttgtttgtgg tggttgtgtg tgggtgtgtg ttttttcttt   2460
ttctttcttt ttattttttt tgaatggggg aggctattta ttgtactgag agtggtgtct   2520
ggatatattc cttttgtctt catcactttc tgaaaataaa cataaaactg ttaaaaaaaa   2580
aaaaaaaaa                                                           2589
```

<210> SEQ ID NO 8
<211> LENGTH: 4609
<212> TYPE: DNA
<213> ORGANISM: Homo sapiens

<400> SEQUENCE: 8
taaagtcatc aaaacaacgt tatatcctgt gtgaaatgct gcagtcagga tgccttgtgg 60
tttgagtgcc ttgatcatgt gccctaaggg gatggtggcg gtggtggtgg ccgtggatga 120
cggagactct caggccttgg caggtgcgtc tttcagttcc cctcacactt cgggttcctc 180
ggggaggagg ggctggaacc ctagcccatc gtcaggacaa agatgctcag gctgctcttg 240
gctctcaact tattcccttc aattcaagta acaggaaaca agattttggt gaagcagtcg 300
cccatgcttg tagcgtacga caatgcggtc aaccttagct ggaaacacct ttgtccaagt 360
cccctatttc ccggaccttc taagcccttt tgggtgctgg tggtggttgg tggagtcctg 420
gcttgctata gcttgctagt aacagtggcc tttattattt tctgggtgag gagtaagagg 480
agcaggctcc tgcacagtga ctacatgaac atgactcccc gccgccccgg gcccacccgc 540
aagcattacc agccctatgc cccaccacgc gacttcgcag cctatcgctc ctgacacgga 600
cgcctatcca gaagccagcc ggctggcagc ccccatctgc tcaatatcac tgctctggat 660
aggaaatgac cgccatctcc agccggccac ctcaggcccc tgttgggcca ccaatgccaa 720
tttttctcga gtgactagac caaatatcaa gatcattttg agactctgaa atgaagtaaa 780
agagatttcc tgtgacaggc caagtcttac agtgccatgg cccacattcc aacttaccat 840
gtacttagtg acttgactga gaagttaggg tagaaaacaa aaagggagtg gattctggga 900
gcctcttccc tttctcactc acctgcacat ctcagtcaag caaagtgtgg tatccacaga 960
cattttagtt gcagaagaaa ggctaggaaa tcattccttt tggttaaatg ggtgtttaat 1020
cttttggtta gtgggttaaa cggggtaagt tagagtaggg ggagggatag gaagacatat 1080
ttaaaaacca ttaaaacact gtctcccact catgaaatga gccacgtagt tcctatttaa 1140
tgctgttttc ctttagttta gaaatacata gacattgtct tttatgaatt ctgatcatat 1200
ttagtcattt tgaccaaatg agggatttgg tcaaatgagg gattccctca aagcaatatc 1260
aggtaaacca agttgctttc ctcactccct gtcatgagac ttcagtgtta atgttcacaa 1320
tatactttcg aaagaataaa atagttctcc tacatgaaga aagaatatgt caggaaataa 1380
ggtcacttta tgtcaaaatt atttgagtac tatgggacct ggcgcagtgg ctcatgcttg 1440
taatcccagc actttgggag gccgaggtgg gcagatcact tgagatcagg accagcctgg 1500
tcaagatggt gaaactccgt ctgtactaaa aatacaaaat ttagcttggc ctggtggcag 1560
gcacctgtaa tcccagctgc ccaagaggct gaggcatgag aatcgcttga acctggcagg 1620
cggaggttgc agtgagccga gatagtgcca cagctctcca gcctgggcga cagagtgaga 1680
ctccatctca aacaacaaca acaacaacaa caacaacaac aaaccacaaa attatttgag 1740
tactgtgaag gattatttgt ctaacagttc attccaatca gaccaggtag gagctttcct 1800
gtttcatatg tttcagggtt gcacagttgg tctctttaat gtcggtgtgg agatccaaag 1860
tgggttgtgg aaagagcgtc cataggagaa gtgagaatac tgtgaaaaag ggatgttagc 1920
attcattaga gtatgaggat gagtcccaag aaggttcttt ggaaggagga cgaatagaat 1980
ggagtaatga aattcttgcc atgtgctgag gagatagcca gcattaggtg acaatcttcc 2040
agaagtggtc aggcagaagg tgccctggtg agagctcctt tacagggact ttatgtggtt 2100
tagggctcag agctccaaaa ctctgggctc agctgctcct gtaccttgga ggtccattca 2160
catgggaaag tattttggaa tgtgtctttt gaagagagca tcagagttct taagggactg 2220
ggtaaggcct gaccctgaaa tgaccatgga tatttttcta cctacagttt gagtcaacta 2280

-continued

```
gaatatgcct ggggaccttg aagaatggcc cttcagtggc cctcaccatt tgttcatgct   2340
tcagttaatt caggtgttga aggagcttag gttttagagg cacgtagact tggttcaagt   2400
ctcgttagta gttgaatagc ctcaggcaag tcactgccca cctaagatga tggttcttca   2460
actataaaat ggagataatg gttacaaatg tctcttccta tagtataatc tccataaggg   2520
catggcccaa gtctgtcttt gactctgcct atccctgaca tttagtagca tgcccgacat   2580
acaatgttag ctattggtat tattgccata tagataaatt atgtataaaa attaaactgg   2640
gcaatagcct aagaaggggg gaatattgta acacaaattt aaacccacta cgcagggatg   2700
aggtgctata atatgaggac cttttaactt ccatcatttt cctgtttctt gaaatagttt   2760
atcttgtaat gaaatataag gcacctccca cttttatgta tagaaagagg tcttttaatt   2820
ttttttaat gtgagaagga agggaggagt aggaatcttg agattccaga tcgaaaatac   2880
tgtactttgg ttgattttta agtgggcttc cattccatgg atttaatcag tcccaagaag   2940
atcaaactca gcagtacttg ggtgctgaag aactgttgga tttaccctgg cacgtgtgcc   3000
acttgccagc ttcttgggca cacagagttc ttcaatccaa gttatcagat tgtatttgaa   3060
aatgacagag ctggagagtt ttttgaaatg gcagtggcaa ataaataaat actttttttt   3120
aaatggaaag acttgatcta tggtaataaa tgattttgtt ttctgactgg aaaaataggc   3180
ctactaaaga tgaatcacac ttgagatgtt tcttactcac tctgcacaga aacaaagaag   3240
aaatgttata cagggaagtc cgttttcact attagtatga accaagaaat ggttcaaaaa   3300
cagtggtagg agcaatgctt tcatagtttc agatatggta gttatgaaga aaacaatgtc   3360
atttgctgct attattgtaa gagtcttata attaatggta ctcctataat ttttgattgt   3420
gagctcacct atttgggtta agcatgccaa tttaaagaga ccaagtgtat gtacattatg   3480
ttctacatat tcagtgataa aattactaaa ctactatatg tctgctttaa atttgtactt   3540
taatattgtc ttttggtatt aagaaagata tgctttcaga atagatatgc ttcgctttgg   3600
caaggaattt ggatagaact tgctatttaa aagaggtgtg gggtaaatcc ttgtataaat   3660
ctccagttta gccttttttg aaaaagctag actttcaaat actaatttca cttcaagcag   3720
ggtacgtttc tggtttgttt gcttgacttc agtcacaatt tcttatcaga ccaatggctg   3780
acctctttga gatgtcaggc taggcttacc tatgtgttct gtgtcatgtg aatgctgaga   3840
agtttgacag agatccaact tcagccttga ccccatcagt ccctcgggtt aactaactga   3900
gccaccggtc ctcatggcta ttttaatgag ggtattgatg gttaaatgca tgtctgatcc   3960
cttatcccag ccatttgcac tgccagctgg gaactatacc agacctggat actgatccca   4020
aagtgttaaa ttcaactaca tgctggagat tagagatggt gccaataaag gacccagaac   4080
caggatcttg attgctatag acttattaat aatccaggtc aaagagagtg acacacactc   4140
tctcaagacc tggggtgagg gagtctgtgt tatctgcaag gccatttgag gctcagaaag   4200
tctctctttc ctatagatat atgcatactt tctgacatat aggaatgtat caggaatact   4260
caaccatcac aggcatgttc ctacctcagg gcctttacat gtcctgttta ctctgtctag   4320
aatgtccttc tgtagatgac ctggcttgcc tcgtcaccct tcaggtcctt gctcaagtgt   4380
catcttctcc cctagttaaa ctaccccaca ccctgtctgc tttccttgct tatttttctc   4440
catagcattt taccatctct tacattagac atttttctta tttatttgta gtttataagc   4500
ttcatgaggc aagtaacttt gctttgtttc ttgctgtatc tccagtgccc agagcagtgc   4560
ctggtatata ataaatattt attgactgag tgaaaaaaaa aaaaaaaaa               4609
```

```
<210> SEQ ID NO 9
<211> LENGTH: 2115
<212> TYPE: DNA
<213> ORGANISM: Homo sapiens

<400> SEQUENCE: 9

agtttccctt ccgctcacct ccgcctgagc agtggagaag gcggcactct ggtggggctg     60

ctccaggcat gcagatccca caggcgccct ggccagtcgt ctgggcggtg ctacaactgg    120

gctggcggcc aggatggttc ttagactccc cagacaggcc ctggaacccc cccaccttct    180

ccccagccct gctcgtggtg accgaagggg acaacgccac cttcacctgc agcttctcca    240

acacatcgga gagcttcgtg ctaaactggt accgcatgag ccccagcaac cagacggaca    300

agctggccgc cttccccgag gaccgcagcc agcccggcca ggactgccgc ttccgtgtca    360

cacaactgcc caacgggcgt gacttccaca tgagcgtggt cagggcccgg cgcaatgaca    420

gcggcaccta cctctgtggg gccatctccc tggcccccaa ggcgcagatc aaagagagcc    480

tgcgggcaga gctcagggtg acagagagaa gggcagaagt gcccacagcc caccccagcc    540

cctcacccag gccagccggc cagttccaaa ccctggtggt tggtgtcgtg ggcggcctgc    600

tgggcagcct ggtgctgcta gtctgggtcc tggccgtcat ctgctcccgg gccgcacgag    660

ggacaatagg agccaggcgc accggccagc ccctgaagga ggacccctca gccgtgcctg    720

tgttctctgt ggactatggg gagctggatt tccagtggcg agagaagacc ccggagcccc    780

ccgtgccctg tgtccctgag cagacggagt atgccaccat tgtctttcct agcggaatgg    840

gcacctcatc ccccgcccgc aggggctcag ctgacggccc tcggagtgcc cagccactga    900

ggcctgagga tggacactgc tcttggcccc tctgaccggc ttccttggcc accagtgttc    960

tgcagaccct ccaccatgag cccgggtcag cgcatttcct caggagaagc aggcagggtg   1020

caggccattg caggccgtcc aggggctgag ctgcctgggg gcgaccgggg ctccagcctg   1080

cacctgcacc aggcacagcc ccaccacagg actcatgtct caatgcccac agtgagccca   1140

ggcagcaggt gtcaccgtcc cctacaggga gggccagatg cagtcactgc ttcaggtcct   1200

gccagcacag agctgcctgc gtccagctcc ctgaatctct gctgctgctg ctgctgctgc   1260

tgctgctgcc tgcggcccgg ggctgaaggc gccgtggccc tgcctgacgc cccggagcct   1320

cctgcctgaa cttgggggct ggttggagat ggccttggag cagccaaggt gcccctggca   1380

gtggcatccc gaaacgccct ggacgcaggg cccaagactg ggcacaggag tgggaggtac   1440

atggggctgg ggactcccca ggagttatct gctccctgca ggcctagaga agtttcaggg   1500

aaggtcagaa gagctcctgg ctgtggtggg cagggcagga aacccctcca cctttacaca   1560

tgcccaggca gcacctcagg ccctttgtgg ggcagggaag ctgaggcagt aagcgggcag   1620

gcagagctgg aggcctttca ggcccagcca gcactctggc ctcctgccgc cgcattccac   1680

cccagcccct cacaccactc gggagaggga catcctacgg tcccaaggtc aggagggcag   1740

ggctggggtt gactcaggcc cctcccagct gtggccacct gggtgttggg agggcagaag   1800

tgcaggcacc tagggccccc catgtgccca ccctgggagc tctccttgga acccattcct   1860

gaaattattt aaaggggttg gccgggctcc caccagggcc tgggtgggaa ggtacaggcg   1920

ttcccccggg gcctagtacc cccgccgtgg cctatccact cctcacatcc acacactgca   1980

cccccactcc tggggcaggg ccaccagcat ccaggcggcc agcaggcacc tgagtggctg   2040

ggacaaggga tccccccttcc ctgtggttct attatattat aattataatt aaatatgaga   2100

gcatgctaag gaaaa                                                    2115
```

<210> SEQ ID NO 10
<211> LENGTH: 1834
<212> TYPE: DNA
<213> ORGANISM: Homo sapiens

<400> SEQUENCE: 10
actttgacag tcttctcatg ctgcctctgc caccttctct gccagaagat accatttcaa 60
ctttaacaca gcatgatcga aacatacaac caaacttctc cccgatctgc ggccactgga 120
ctgcccatca gcatgaaaat ttttatgtat ttacttactg tttttcttat cacccagatg 180
attgggtcag cactttttgc tgtgtatctt catagaaggt tggacaagat agaagatgaa 240
aggaatcttc atgaagattt tgtattcatg aaaacgatac agagatgcaa cacaggagaa 300
agatccttat ccttactgaa ctgtgaggag attaaaagcc agtttgaagg ctttgtgaag 360
gatataatgt taaacaaaga ggagacgaag aaagaaaaca gctttgaaat gcaaaaaggt 420
gatcagaatc ctcaaattgc ggcacatgtc ataagtgagg ccagcagtaa aacaacatct 480
gtgttacagt gggctgaaaa aggatactac accatgagca acaacttggt aaccctggaa 540
aatgggaaac agctgaccgt taaaagacaa ggactctatt atatctatgc ccaagtcacc 600
ttctgttcca atcgggaagc ttcgagtcaa gctccattta tagccagcct ctgcctaaag 660
tcccccggta gattcgagag aatcttactc agagctgcaa atacccacag ttccgccaaa 720
ccttgcgggc aacaatccat tcacttggga ggagtatttg aattgcaacc aggtgcttcg 780
gtgtttgtca atgtgactga tccaagccaa gtgagccatg gcactggctt cacgtccttt 840
ggcttactca aactctgaac agtgtcacct tgcaggctgt ggtggagctg acgctgggag 900
tcttcataat acagcacagc ggttaagccc accccctgtt aactgcctat ttataaccct 960
aggatcctcc ttatggagaa ctatttatta tacactccaa ggcatgtaga actgtaataa 1020
gtgaattaca ggtcacatga aaccaaaacg ggccctgctc cataagagct tatatatctg 1080
aagcagcaac cccactgatg cagacatcca gagagtccta tgaaaagaca aggccattat 1140
gcacaggttg aattctgagt aaacagcaga taacttgcca agttcagttt tgtttctttg 1200
cgtgcagtgt ctttccatgg ataatgcatt tgatttatca gtgaagatgc agaagggaaa 1260
tggggagcct cagctcacat tcagttatgg ttgactctgg gttcctatgg ccttgttgga 1320
gggggccagg ctctagaacg tctaacacag tggagaaccg aaaccccccc cccccccccg 1380
ccaccctctc ggacagttat tcattctctt tcaatctctc tctctccatc tctctctttc 1440
agtctctctc tctcaacctc tttcttccaa tctctctttc tcaatctctc tgtttccctt 1500
tgtcagtctc ttccctcccc cagtctctct tctcaatccc cctttctaac acacacacac 1560
acacacacac acacacacac acacacacac acacacacac agagtcaggc cgttgctagt 1620
cagttctctt ctttccaccc tgtccctatc tctaccacta tagatgaggg tgaggagtag 1680
ggagtgcagc cctgagcctg cccactcctc attacgaaat gactgtattt aaaggaaatc 1740
tattgtatct acctgcagtc tccattgttt ccagagtgaa cttgtaatta tcttgttatt 1800
tattttttga ataataaaga cctcttaaca ttaa 1834

<210> SEQ ID NO 11
<211> LENGTH: 3878
<212> TYPE: DNA
<213> ORGANISM: Homo sapiens

<400> SEQUENCE: 11
ccgcctcctg gcctcctggc tgaggggaag ctgagtgggc cacggcccat gtgtcgcact 60

-continued

```
cgcctcggct cccacacagc cgcctctgct ccagcaagga tgtggctctt ccacactctg    120
ctctgcatag ccagcctggc cctgctggcc gctttcaatg tggatgtggc ccggccctgg    180
ctcacgccca agggaggtgc ccctttcgtg ctcagctccc ttctgcacca agaccccagc    240
accaaccaga cctggctcct ggtcaccagc cccagaacca agaggacacc agggcccctc    300
catcgatgtt cccttgtcca ggatgaaatc ctttgccatc ctgtagagca tgtccccatc    360
cccaagggga ggcaccgggg agtgaccgtt gtccggagcc accacggtgt tttgatatgc    420
attcaagtgc tggtccggcg gcctcacagc ctcagctcag aactcacagg cacctgtagc    480
ctcctgggcc ctgacctccg tccccaggct caggccaact tcttcgacct tgaaaatctc    540
ctggatccag atgcacgtgt ggacactgga gactgctaca gcaacaaaga aggcggtgga    600
gaagacgatg tgaacacagc caggcagcgc cgggctctgg agaaggagga ggaggaagac    660
aaggaggagg aggaagacga ggaggaggag gaagctggca ccgagattgc catcatcctg    720
gatggctcag gaagcattga tcccccagac tttcagagag ccaaagactt catctccaac    780
atgatgagga acttctatga aaagtgtttt gagtgcaact ttgccttggt gcagtatgga    840
ggagtgatcc agactgagtt tgaccttcgg gacagccagg atgtgatggc ctccctcgcc    900
agagtccaga acatcactca agtggggagt gtcaccaaga ctgcctcagc catgcaacac    960
gtcttagaca gcatcttcac ctcaagccac ggctccagga gaaaggcatc caaggtcatg   1020
gtggtgctca ccgatggtgg catattcgag gaccccctca accttacgac agtcatcaac   1080
tcccccaaaa tgcagggtgt tgagcgcttt gccattgggg tgggagaaga atttaagagt   1140
gctaggactg cgagggaact gaacctgatc gcctcagacc cggatgagac ccatgctttc   1200
aaggtgacca actacatggc gctggatggg ctgctgagca aactgcggta caacatcatc   1260
agcatggaag gcacggttgg agacgccctt cactaccagc tggcacagat tggcttcagt   1320
gctcagatcc tggatgagcg gcaggtgctg ctcggcgccg tcggggcctt tgactggtcc   1380
ggaggggcgt tgctctacga cacacgcagc cgccggggcc gcttcctgaa ccagacagcg   1440
gcggcggcgg cagacgcgga ggctgcgcag tacagctacc tgggttacgc tgtggccgtg   1500
ctgcacaaga cctgcagcct ctcctacatc gcgggggctc cacggtacaa acatcatggg   1560
gccgtgtttg agctccagaa ggagggcaga gaggccagct tcctgccagt gctggaggga   1620
gagcagatgg ggtcctattt tggctctgag ctgtgccctg tggacattga catggatgga   1680
agcacggact tcttgctggt ggctgctcca ttttaccacg ttcatggaga agaaggcaga   1740
gtctacgtgt accgtctcag cgagcaggat ggttctttct ccttggcacg catactgagt   1800
gggcaccccg ggttcaccaa tgcccgcttt ggctttgcca tggcggctat gggggatctc   1860
agtcaggata agctcacaga tgtggccatc ggggcccccc tggaaggttt tggggcagat   1920
gatggtgcca gcttcggcag tgtgtatatc tacaatggac actgggacgg cctctccgcc   1980
agcccctcgc agcggatcag agcctccacg gtggccccag gactccagta cttcggcatg   2040
tccatggctg gtggctttga tattagtggc gacggccttg ccgacatcac cgtgggcact   2100
ctgggccagg cggttgtgtt ccgctcccgg cctgtggttc gcctgaaggt ctccatggcc   2160
ttcaccccca gcgcactgcc catcggcttc aacggcgtcg tgaatgtccg tttatgtttt   2220
gaaatcagct ctgtaaccac agcctctgag tcaggcctcc gcgaggcact tctcaacttc   2280
acgctggatg tggatgtggg gaagcagagg agacggctgc agtgttcaga cgtaagaagc   2340
tgtctgggct gcctgaggga gtggagcagc ggatcccagc tttgtgagga cctcctgctc   2400
```

-continued atgcccacag agggagagct ctgtgaggag gactgcttct ccaatgccag tgtcaaagtc 2460
agctaccagc tccagacccc tgagggacag acggaccatc cccagcccat cctggaccgc 2520
tacactgagc cctttgccat cttccagctg ccctatgaga aggcctgcaa gaataagctg 2580
ttttgtgtcg cagaattaca gttggccacc accgtctctc agcaggagtt ggtggtgggt 2640
ctcacaaagg agctgaccct gaacattaac ctaactaact ccggggaaga ttcctacatg 2700
acaagcatgg ccttgaatta ccccagaaac ctgcagttga agaggatgca aaagcctccc 2760
tctccaaaca ttcagtgtga tgaccctcag ccggttgctt ctgtcctgat catgaactgc 2820
aggattggtc accccgtcct caagaggtca tctgctcatg tttcagtcgt ttggcagcta 2880
gaggagaatg cctttccaaa caggacagca gacatcactg tgactgtcac caattccaat 2940
gaaagacggt ctttggccaa cgagacccac acccttcaat tcaggcatgg cttcgttgca 3000
gttctgtcca aaccatccat aatgtacgtg aacacaggcc aggggctttc tcaccacaaa 3060
gaattcctct tccatgtaca tggggagaac ctctttggag cagaatacca gttgcaaatt 3120
tgcgtcccaa ccaaattacg aggtctccag gttgtagcag tgaagaagct gacgaggact 3180
caggcctcca cggtgtgcac ctggagtcag gagcgcgctt gtgcgtacag ttcggttcag 3240
catgtggaag aatggcattc agtgagctgt gtcatcgctt cagataaaga aaatgtcacc 3300
gtggctgcag agatctcctg ggatcactct gaggagttac taaaagatgt aactgaactg 3360
cagatccttg gtgaaatatc tttcaacaaa tctctatatg agggactgaa tgcagagaac 3420
cacagaacta agatcactgt cgtcttcctg aaagatgaga agtaccattc tttgcctatc 3480
atcattaaag gcagcgttgg tggacttctg gtgttgatcg tgattctggt catcctgttc 3540
aagtgtggct tttttaaaag aaaatatcaa caactgaact tggagagcat caggaaggcc 3600
cagctgaaat cagagaatct gctcgaagaa gagaattagg acctgctatc cactgggaga 3660
ggctatcagc cagtcctggg acttggagac ccagcatcct ttgcattact ttttccttca 3720
ggatgatcta gagcagcatg gagctgttgg tagaatatta gtttttaacc atacattgtc 3780
ccaaaagtgt ctgtgcattg tgcaaaaagt aaacttagga aacatttggt attaaataaa 3840
tttacacttt tctttgcagt aaaaaaaaaa aaaaaaaa 3878

<210> SEQ ID NO 12
<211> LENGTH: 1953
<212> TYPE: DNA
<213> ORGANISM: Homo sapiens

<400> SEQUENCE: 12
gcagaccttg cttcatgagc aagctcatct ctggaacaaa ctggcaaagc atctctgctg 60
gtgttcatca gaacagacac catggcagag catgattacc atgaagacta tgggttcagc 120
agtttcaatg acagcagcca ggaggagcat caagacttcc tgcagttcag caaggtcttt 180
ctgccctgca tgtacctggt ggtgtttgtc tgtggtctgg tggggaactc tctggtgctg 240
gtcatatcca tcttctacca taagttgcag agcctgacgg atgtgttcct ggtgaaccta 300
cccctggctg acctggtgtt tgtctgcact ctgcccttct gggcctatgc aggcatccat 360
gaatgggtgt ttggccaggt catgtgcaag agcctactgg gcatctacac tattaacttc 420
tacacgtcca tgctcatcct cacctgcatc actgtggatc gtttcattgt agtggttaag 480
gccaccaagg cctacaacca gcaagccaag aggatgacct ggggcaaggt caccagcttg 540
ctcatctggg tgatatccct gctggtttcc ttgccccaaa ttatctatgg caatgtcttt 600
aatctcgaca agctcatatg tggttaccat gacgaggcaa tttccactgt ggttcttgcc 660

-continued

```
acccagatga cactggggtt cttcttgcca ctgctcacca tgattgtctg ctattcagtc    720
ataatcaaaa cactgcttca tgctggaggc ttccagaagc acagatctct aaagatcatc    780
ttcctggtga tggctgtgtt cctgctgacc cagatgccct tcaacctcat gaagttcatc    840
cgcagcacac actgggaata ctatgccatg accagctttc actacaccat catggtgaca    900
gaggccatcg catacctgag ggcctgcctt aaccctgtgc tctatgcctt tgtcagcctg    960
aagtttcgaa agaacttctg gaaacttgtg aaggacattg gttgcctccc ttaccttggg   1020
gtctcacatc aatggaaatc ttctgaggac aattccaaga ctttttctgc ctcccacaat   1080
gtggaggcca ccagcatgtt ccagttatag gccttgccag ggtttcgaga agctgctctg   1140
gaatttgcaa gtcatggctg tgccctcttg atgtggtgag gcaggctttg tttatagctt   1200
gcgcattctc atggagaagt tatcagacac tctggctggt ttggaatgct tcttctcagg   1260
catgaacatg tactgttctc ttcttgaaca ctcatgctga aagcccaagt agggggtcta   1320
aaatttttaa ggactttcct tcctccatct ccaagaatgc tgaaaccaag gggatgaca   1380
tgtgactcct atgatctcag gttctccttg attgggactg gggctgaagg ttgaagaggt   1440
gagcacggcc aacaaagctg ttgatggtag gtggcacact gggtgcccaa gctcagaagg   1500
ctcttctgac tactgggcaa agagtgtaga tcagagcagc agtgaaaaca agtgctggca   1560
ccaccaggca cctcacagaa atgagatcag gctctgcctc accttggggc ttgacttttg   1620
tataggtaga tgttcagatt gctttgatta atccagaata actagcacca gggactatga   1680
atgggcaaaa ctgaattata agaggctgat aattccagtg gtccatggaa tgcttgaaaa   1740
atgtgcaaaa cagcgtttaa gactgtaatg aatctaagca gcatttctga agtggactct   1800
ttggtggctt tgcattttaa aaatgaaatt ttccaatgtc tgccacacaa acgtatgtaa   1860
atgtatatac ccacacacat acacacatat gtcatatatt actagcatat gagtttcata   1920
gctaagaaat aaaactgtta aagtctccaa act                                 1953
```

<210> SEQ ID NO 13
<211> LENGTH: 1686
<212> TYPE: DNA
<213> ORGANISM: Homo sapiens

<400> SEQUENCE: 13

```
cagacgctcc ctcagcaagg acagcagagg accagctaag agggagagaa gcaactacag     60
accccccctg aaaacaaccc tcagacgcca catcccctga caagctgcca ggcaggttct    120
cttcctctca catactgacc cacggctcca ccctctctcc cctggaaagg acaccatgag    180
cactgaaagc atgatccggg acgtggagct ggccgaggag gcgctcccca agaagacagg    240
ggggccccag ggctccaggc ggtgcttgtt cctcagcctc ttctccttcc tgatcgtggc    300
aggcgccacc acgctcttct gcctgctgca ctttggagtg atcggccccc agagggaaga    360
gttccccagg gacctctctc taatcagccc tctggcccag gcagtcagat catcttctcg    420
aaccccgagt gacaagcctg tagcccatgt tgtagcaaac cctcaagctg aggggcagct    480
ccagtggctg aaccgccggg ccaatgccct cctggccaat ggcgtggagc tgagagataa    540
ccagctggtg gtgccatcag agggcctgta cctcatctac tcccaggtcc tcttcaaggg    600
ccaaggctgc ccctccaccc atgtgctcct cacccacacc atcagccgca tcgccgtctc    660
ctaccagacc aaggtcaacc tcctctctgc catcaagagc ccctgccaga gggagacccc    720
agagggggct gaggccaagc cctggtatga gcccatctat ctgggagggg tcttccagct    780
```

```
ggagaagggt gaccgactca gcgctgagat caatcggccc gactatctcg actttgccga    840

gtctgggcag gtctactttg ggatcattgc cctgtgagga ggacgaacat ccaaccttcc    900

caaacgcctc ccctgcccca atccctttat tacccctcc ttcagacacc ctcaacctct     960

tctggctcaa aaagagaatt gggggcttag ggtcggaacc caagcttaga actttaagca   1020

acaagaccac cacttcgaaa cctgggattc aggaatgtgt ggcctgcaca gtgaagtgct   1080

ggcaaccact aagaattcaa actggggcct ccagaactca ctggggccta cagctttgat   1140

ccctgacatc tggaatctgg agaccaggga gcctttggtt ctggccagaa tgctgcagga   1200

cttgagaaga cctcacctag aaattgacac aagtggacct taggccttcc tctctccaga   1260

tgtttccaga cttccttgag acacggagcc cagccctccc catggagcca gctccctcta   1320

tttatgtttg cacttgtgat tatttattat ttatttatta tttatttatt tacagatgaa   1380

tgtatttatt tgggagaccg gggtatcctg ggggacccaa tgtaggagct gccttggctc   1440

agacatgttt tccgtgaaaa cggagctgaa caataggctg ttcccatgta gccccctggc   1500

ctctgtgcct tcttttgatt atgtttttta aaatatttat ctgattaagt tgtctaaaca   1560

atgctgattt ggtgaccaac tgtcactcat tgctgagcct ctgctcccca ggggagttgt   1620

gtctgtaatc gccctactat tcagtggcga gaaataaagt ttgcttagaa aagaaaaaaa   1680

aaaaaa                                                              1686
```

```
<210> SEQ ID NO 14
<211> LENGTH: 3216
<212> TYPE: DNA
<213> ORGANISM: Homo sapiens

<400> SEQUENCE: 14

ggcagtttcc tggctgaaca cgccagccca atacttaaag agagcaactc ctgactccga     60

tagagactgg atggacccac aagggtgaca gcccaggcgg accgatcttc ccatcccaca    120

tcctccggcg cgatgccaaa aagaggctga cggcaactgg gccttctgca gagaaagacc    180

tccgcttcac tgccccggct ggtcccaagg gtcaggaaga tggattcata cctgctgatg    240

tggggactgc tcacgttcat catggtgcct ggctgccagg cagagctctg tgacgatgac    300

ccgccagaga tcccacacgc cacattcaaa gccatggcct acaaggaagg aaccatgttg    360

aactgtgaat gcaagagagg tttccgcaga ataaaaagcg ggtcactcta tatgctctgt    420

acaggaaact ctagccactc gtcctgggac aaccaatgtc aatgcacaag ctctgccact    480

cggaacacaa cgaaacaagt gacacctcaa cctgaagaac agaaagaaag gaaaaccaca    540

gaaatgcaaa gtccaatgca gccagtggac caagcgagcc ttccaggtca ctgcagggaa    600

cctccaccat gggaaaatga agccacagag agaatttatc atttcgtggt ggggcagatg    660

gtttattatc agtgcgtcca gggatacagg gctctacaca gaggtcctgc tgagagcgtc    720

tgcaaaatga cccacgggaa gacaaggtgg acccagcccc agctcatatg cacaggtgaa    780

atggagacca gtcagtttcc aggtgaagag aagcctcagg caagccccga aggccgtcct    840

gagagtgaga cttcctgcct cgtcacaaca acagattttc aaatacagac agaaatggct    900

gcaaccatgg agacgtccat atttacaaca gagtaccagg tagcagtggc cggctgtgtt    960

ttcctgctga tcagcgtcct cctcctgagt gggctcacct ggcagcggag acagaggaag   1020

agtagaagaa caatctagaa aaccaaaaga acaagaattt cttggtaaga agccgggaac   1080

agacaacaga agtcatgaag cccaagtgaa atcaaaggtg ctaaatggtc gcccaggaga   1140

catccgttgt gcttgcctgc gttttggaag ctctgaagtc acatcacagg acacggggca   1200
```

```
gtggcaacct tgtctctatg ccagctcagt cccatcagag agcgagcgct acccacttct   1260

aaatagcaat ttcgccgttg aagaggaagg gcaaaaccac tagaactctc catcttattt   1320

tcatgtatat gtgttcatta aagcatgaat ggtatggaac tctctccacc ctatatgtag   1380

tataaagaaa agtaggttta cattcatctc attccaactt cccagttcag gagtcccaag   1440

gaaagcccca gcactaacgt aaatacacaa cacacacact ctaccctata caactggaca   1500

ttgtctgcgt ggttcctttc tcagccgctt ctgactgctg attctcccgt tcacgttgcc   1560

taataaacat ccttcaagaa ctctgggctg ctacccagaa atcattttac ccttggctca   1620

atcctctaag ctaacccccct tctactgagc cttcagtctt gaatttctaa aaaacagagg   1680

ccatggcaga ataatctttg ggtaacttca aaacggggca gccaaaccca tgaggcaatg   1740

tcaggaacag aaggatgaat gaggtcccag gcagagaatc atacttagca aagttttacc   1800

tgtgcgttac taattggcct ctttaagagt tagtttcttt gggattgcta tgaatgatac   1860

cctgaatttg gcctgcacta atttgatgtt tacaggtgga cacacaaggt gcaaatcaat   1920

gcgtacgttt cctgagaagt gtctaaaaac accaaaaagg gatccgtaca ttcaatgttt   1980

atgcaaggaa ggaaagaaag aaggaagtga agagggagaa gggatggagg tcacactggt   2040

agaacgtaac cacggaaaag agcgcatcag gcctggcacg gtggctcagg cctataaccc   2100

cagctcccta ggagaccaag gcgggagcat ctcttgaggc caggagtttg agaccagcct   2160

gggcagcata gcaagacaca tccctacaaa aaattagaaa ttggctggat gtggtggcat   2220

acgcctgtag tcctagccac tcaggaggct gaggcaggag gattgcttga gcccaggagt   2280

tcgaggctgc agtcagtcat gatggcacca ctgcactcca gcctgggcaa cagagcaaga   2340

tcctgtcttt aaggaaaaaa agacaagatg agcataccag cagtccttga acattatcaa   2400

aaagttcagc atattagaat caccgggagg ccttgttaaa agagttcgct gggcccatct   2460

tcagagtctc tgagttgttg gtctggaata gagccaaatg ttttgtgtgt ctaacaattc   2520

ccaggtgctg ttgctgctgc tactattcca ggaacacact ttgagaacca ttgtgttatt   2580

gctctgcacg cccacccact ctcaactccc acgaaaaaaa tcaacttcca gagctaagat   2640

ttcggtggaa gtcctggttc catatctggt gcaagatctc ccctcacgaa tcagttgagt   2700

caacattcta gctcaacaac atcacacgat taacattaac gaaaattatt catttgggaa   2760

actatcagcc agttttcact tctgaagggg caggagagtg ttatgagaaa tcacggcagt   2820

tttcagcagg gtccagattc agattaaata actattttct gtcatttctg tgaccaacca   2880

catacaaaca gactcatctg tgcactctcc ccctccccct tcaggtatat gttttctgag   2940

taaagttgaa aagaatctca gaccagaaaa tatagatata tatttaaatc ttacttgagt   3000

agaactgatt acgacttttg ggtgttgagg ggtctataag atcaaaactt ttccatgata   3060

atactaagat gttatcgacc atttatctgt ccttctctca aaagtgtatg gtggaatttt   3120

ccagaagcta tgtgatacgt gatgatgtca tcactctgct gttaacatat aataaattta   3180

ttgctattgt ttataaaaga ataaatgata tttttt                             3216
```

<210> SEQ ID NO 15
<211> LENGTH: 1320
<212> TYPE: DNA
<213> ORGANISM: Homo sapiens

<400> SEQUENCE: 15

```
cggaagggga agggggtgga ggttgctgct atgagagaga aaaaaaaaac agccacaata     60
```

-continued

```
gagattctgc cttcaaaggt tggcttgcca cctgaagcag ccactgccca gggggtgcaa    120
agaagagaca gcagcgccca gcttggaggt gctaactcca gaggccagca tcagcaactg    180
ggcacagaaa ggagccgcct gggcagggac catggcacgg ccacatccct ggtggctgtg    240
cgttctgggg accctggtgg ggctctcagc tactccagcc cccaagagct gcccagagag    300
gcactactgg gctcagggaa agctgtgctg ccagatgtgt gagccaggaa cattcctcgt    360
gaaggactgt gaccagcata gaaaggctgc tcagtgtgat ccttgcatac cgggggtctc    420
cttctctcct gaccaccaca cccggcccca ctgtgagagc tgtcggcact gtaactctgg    480
tcttctcgtt cgcaactgca ccatcactgc caatgctgag tgtgcctgtc gcaatggctg    540
gcagtgcagg gacaaggagt gcaccgagtg tgatcctctt ccaaaccctt cgctgaccgc    600
tcggtcgtct caggccctga gcccacaccc tcagcccacc cacttacctt atgtcagtga    660
gatgctggag gccaggacag ctgggcacat gcagactctg gctgacttca ggcagctgcc    720
tgcccggact ctctctaccc actggccacc ccaaagatcc ctgtgcagct ccgattttat    780
tcgcatcctt gtgatcttct ctggaatgtt ccttgttttc accctggccg gggccctgtt    840
cctccatcaa cgaaggaaat atagatcaaa caaaggagaa agtcctgtgg agcctgcaga    900
gccttgtcgt tacagctgcc ccagggagga ggagggcagc accatcccca tccaggagga    960
ttaccgaaaa ccggagcctg cctgctcccc ctgagccagc acctgcggga gctgcactac   1020
agccctggcc tccaccccca ccccgccgac catccaaggg agagtgagac ctggcagcca   1080
caactgcagt cccatcctct tgtcagggcc ctttcctgtg tacacgtgac agagtgcctt   1140
ttcgagactg gcagggacga ggacaaatat ggatgaggtg gagagtggga agcaggagcc   1200
cagccagctg cgcctgcgct gcaggagggc gggggctctg gttgtaaaac acacttcctg   1260
ctgcgaaaga cccacatgct acaagacggg caaaataaag tgacagatga ccaccctgca   1320
```

<210> SEQ ID NO 16
<211> LENGTH: 1923
<212> TYPE: DNA
<213> ORGANISM: Homo sapiens

<400> SEQUENCE: 16

```
cttctgtgtg tgcacatgtg taatacatat ctgggatcaa agctatctat ataaagtcct     60
tgattctgtg tgggttcaaa cacatttcaa agcttcagga tcctgaaagg ttttgctcta    120
cttcctgaag acctgaacac cgctcccata aagccatggc ttgccttgga tttcagcggc    180
acaaggctca gctgaacctg gctaccagga cctggccctg cactctcctg tttttcttc    240
tcttcatccc tgtcttctgc aaagcaatgc acgtggccca gcctgctgtg gtactggcca    300
gcagccgagg catcgccagc tttgtgtgtg agtatgcatc tccaggcaaa gccactgagg    360
tccgggtgac agtgcttcgg caggctgaca gccaggtgac tgaagtctgt gcggcaacct    420
acatgatggg gaatgagttg accttcctag atgattccat ctgcacgggc acctccagtg    480
gaaatcaagt gaacctcact atccaaggac tgagggccat ggacacggga ctctacatct    540
gcaaggtgga gctcatgtac ccaccgccat actacctggg cataggcaac ggaacccaga    600
tttatgtaat tgctaaagaa aagaagccct cttacaacag ggtctatgt gaaaatgccc    660
ccaacagagc cagaatgtga aaagcaattt cagccttatt ttattcccat caattgagaa    720
accattatga agaagagagt ccatatttca atttccaaga gctgaggcaa ttctaacttt    780
tttgctatcc agctattttt atttgtttgt gcatttgggg ggaattcatc tctctttaat    840
ataaagttgg atgcggaacc caaattacgt gtactacaat ttaaagcaaa ggagtagaaa    900
```

gacagagctg ggatgtttct gtcacatcag ctccactttc agtgaaagca tcacttggga 960
ttaatatggg gatgcagcat tatgatgtgg gtcaaggaat taagttaggg aatggcacag 1020
cccaaagaag gaaaaggcag ggagcgaggg agaagactat attgtacaca ccttatattt 1080
acgtatgaga cgtttatagc cgaaatgatc ttttcaagtt aaattttatg ccttttattt 1140
cttaaacaaa tgtatgatta catcaaggct tcaaaaatac tcacatggct atgttttagc 1200
cagtgatgct aaaggttgta ttgcatatat acatatatat atatatatat atatatatat 1260
atatatatat atatatatat atatatattt taatttgata gtattgtgca tagagccacg 1320
tatgtttttg tgtatttgtt aatggtttga atataaacac tatatggcag tgtctttcca 1380
ccttgggtcc cagggaagtt ttgtggagga gctcaggaca ctaatacacc aggtagaaca 1440
caaggtcatt tgctaactag cttggaaact ggatgaggtc atagcagtgc ttgattgcgt 1500
ggaattgtgc tgagttggtg ttgacatgtg ctttggggct tttacaccag ttcctttcaa 1560
tggtttgcaa ggaagccaca gctggtggta tctgagttga cttgacagaa cactgtcttg 1620
aagacaatgg cttactccag gagacccaca ggtatgacct tctaggaagc tccagttcga 1680
tgggcccaat tcttacaaac atgtggttaa tgccatggac agaagaaggc agcaggtggc 1740
agaatggggt gcatgaaggt ttctgaaaat taacactgct tgtgttttta actcaatatt 1800
ttccatgaaa atgcaacaac atgtataata tttttaatta aataaaaatc tgtggtggtc 1860
gttttaaaaa aaaaaaaaaa aaaaaaaaaa aaaaaaaaaa aaaaaaaaaa aaaaaaaaaa 1920
aaa 1923

<210> SEQ ID NO 17
<211> LENGTH: 907
<212> TYPE: DNA
<213> ORGANISM: Homo sapiens

<400> SEQUENCE: 17
ggcgcaacgc tgagcagctg gcgcgtcccg cgcggcccca gttctgcgca gcttcccgag 60
gctccgcacc agccgcgctt ctgtccgcct gcagggcatt ccagaaagat gaggatattt 120
gctgtcttta tattcatgac ctactggcat ttgctgaacg catttactgt cacggttccc 180
aaggacctat atgtggtaga gtatggtagc aatatgacaa ttgaatgcaa attcccagta 240
gaaaaacaat tagacctggc tgcactaatt gtctattggg aaatggagga taagaacatt 300
attcaatttg tgcatggaga ggaagacctg aaggttcagc atagtagcta cagacagagg 360
gcccggctgt tgaaggacca gctctccctg ggaaatgctg cacttcagat cacagatgtg 420
aaattgcagg atgcaggggt gtaccgctgc atgatcagct atggtggtgc cgactacaag 480
cgaattactg tgaaagtcaa tgccccatac aacaaaatca accaaagaat tttggttgtg 540
gatccagtca cctctgaaca tgaactgaca tgtcaggctg agggctaccc caaggccgaa 600
gtcatctgga caagcagtga ccatcaagtc ctgagtggta agaccaccac caccaattcc 660
aagagagagg agaagctttt caatgtgacc agcacactga gaatcaacac aacaactaat 720
gagattttct actgcacttt taggagatta gatcctgagg aaaaccatac agctgaattg 780
gtcatcccag gtaatattct gaatgtgtcc attaaaatat gtctaacact gtcccctagc 840
acctagcatg atgtctgcct atcatagtca ttcagtgatt gttgaataaa tgaatgaatg 900
aataaca 907

<210> SEQ ID NO 18

<211> LENGTH: 2543
<212> TYPE: DNA
<213> ORGANISM: Homo sapiens

<400> SEQUENCE: 18
cttgtgggaa ctgtcagacc agctccaggc gctggggctt tctcagtggc cttgtcagct 60
cacagcaggc gttaacagcc tctaattgag gaaactgtgg ctggacaggt tgcaaggcag 120
ttctgctccc catcgtcctc ttgctgactg ggactgctg agcccgtgca cggcagagag 180
tctggtgggg tggaggggct ggcctggccc ctctgtcctg tggaaatgct ggggcaagtg 240
gtcaccctca tactcctcct gctcctcaag gtgtatcagg gcaaaggatg ccagggatca 300
gctgaccatg tggttagcat ctcgggagtg cctcttcagt tacaaccaaa cagcatacag 360
acgaaggttg acagcattgc atggaagaag ttgctgccct cacaaaatgg atttcatcac 420
atattgaagt gggagaatgg ctctttgcct tccaatactt ccaatgatag attcagtttt 480
atagtcaaga acttgagtct tctcatcaag gcagctcagc agcaggacag tggcctctac 540
tgcctggagg tcaccagtat atctggaaaa gttcagacag ccacgttcca ggtttttgta 600
tttgaatctc tgcttccaga taaagttgag aaaccccgcc tacaggggca ggggaagatc 660
ctggacagag ggagatgcca agtggctctg tcttgcttgg tctccaggga tggcaatgtg 720
tcctatgctt ggtacagagg gagcaagctg atccagacag cagggaacct cacctacctg 780
gacgaggagg ttgacattaa tggcactcac acatatacct gcaatgtcag caatcctgtt 840
agctgggaaa gccacaccct gaatctcact caggactgtc agaatgccca tcaggaattc 900
agattttggc cgtttttggt gatcatcgtg attctaagcg cactgttcct tggcaccctt 960
gcctgcttct gtgtgtggag gagaaagagg aaggagaagc agtcagagac cagtcccaag 1020
gaatttttga caatttacga agatgtcaag gatctgaaaa ccaggagaaa tcacgagcag 1080
gagcagactt ttcctggagg ggggagcacc atctactcta tgatccagtc ccagtcttct 1140
gctcccacgt cacaagaacc tgcatataca ttatattcat taattcagcc ttccaggaag 1200
tctggatcca ggaagaggaa ccacagccct tccttcaata gcactatcta tgaagtgatt 1260
ggaaagagtc aacctaaagc ccagaaccct gctcgattga gccgcaaaga gctggagaac 1320
tttgatgttt attcctagtt gctgcagcaa ttctcacctt tcttgcacat cagcatctgc 1380
tttgggaatt ggcacagtgg atgacggcac aggagtctct atagaacagt tcctagtctg 1440
gagaggatat ggaaatttgt tcttgttcta tattttgttt tgaaaatgat gtctaacaac 1500
catgataaga gcaaggctgt taaataatat cttccaattt acagatcaga catgaatggg 1560
tggaggggtt aggttgttca caaaaggcca cattccaagt atttgtaatc tagaaagtgt 1620
tatgtaagtg atgttattag catcgagatt ccctccacct gattttcaag ctgtcacttg 1680
tttccttttc tcccctctct gggttgactg catttctaga ctctcgccgg cccaggccca 1740
tcttccaaag caagaggaag gaatgataat ggtgactcag gggaagaaga aacagccctc 1800
ctctgaaagc ctggactgtc cggctgtgaa ctggctggca ggttctgcac gtgggtgggg 1860
gccagggcct gggctttact caattgcaga gaaaaaactt tctccctgca tctcatacct 1920
ttacctctgg ccagttggcc accaggggga gtgggctgaa gggagagtag atggtgcaaa 1980
gcaagcccat ctctaagtag aaaaatcacc cagagcacat gctgacctga taactggggt 2040
gttgagacca gctttgtcca tggtatgatg tttgatttat gaagacgcat tgttagaaat 2100
ccatttggct tcttcataga agtggcttcc cagaggaaga ggcctctcag aaaccatgtt 2160
ctatttaagt tctgagtcct gatgagtgtt ccccaggatg cacattgaag ggagggctca 2220

-continued ggcagctgag ggctgagaat gaggcagttg gaatctagac actatgctgg gttccctgag 2280
tcgtcaggcc agacatttca acaaggctgt ggggagcagg gctgtgactc tggctgagcc 2340
caggaaagcg acaagggtga actgggagag gacttactca gagaccccaa caggtgatac 2400
tgcacaaagc ctggttcttc aattttccta ccctgtatct aacataggag tttcatataa 2460
aacggtgata tcatgcagat gcagtctgaa ttccttgcct gaattaaatt tatgtatcct 2520
ctccaaaaaa aaaaaaaaaa aaa 2543

<210> SEQ ID NO 19
<211> LENGTH: 1629
<212> TYPE: DNA
<213> ORGANISM: Homo sapiens

<400> SEQUENCE: 19
acacatcagg ggcttgctct tgcaaaacca aaccacaaga cagacttgca aaagaaggca 60
tgcacagctc agcactgctc tgttgcctgg tcctcctgac tggggtgagg gccagcccag 120
gccagggcac ccagtctgag aacagctgca cccacttccc aggcaacctg cctaacatgc 180
ttcgagatct ccgagatgcc ttcagcagag tgaagacttt ctttcaaatg aaggatcagc 240
tggacaactt gttgttaaag gagtccttgc tggaggactt taagggttac ctgggttgcc 300
aagccttgtc tgagatgatc cagttttacc tggaggaggt gatgccccaa gctgagaacc 360
aagacccaga catcaaggcg catgtgaact ccctggggga gaacctgaag accctcaggc 420
tgaggctacg gcgctgtcat cgatttcttc cctgtgaaaa caagagcaag gccgtggagc 480
aggtgaagaa tgcctttaat aagctccaag agaaaggcat ctacaaagcc atgagtgagt 540
ttgacatctt catcaactac atagaagcct acatgacaat gaagatacga aactgagaca 600
tcagggtggc gactctatag actctaggac ataaattaga ggtctccaaa atcggatctg 660
gggctctggg atagctgacc cagccccttg agaaacctta ttgtacctct cttatagaat 720
atttattacc tctgatacct caacccccat ttctatttat ttactgagct tctctgtgaa 780
cgatttagaa agaagcccaa tattataatt tttttcaata tttattattt tcacctgttt 840
ttaagctgtt tccatagggt gacacactat ggtatttgag tgttttaaga taaattataa 900
gttacataag ggaggaaaaa aaatgttctt tggggagcca acagaagctt ccattccaag 960
cctgaccacg ctttctagct gttgagctgt tttccctgac ctccctctaa tttatcttgt 1020
ctctgggctt ggggcttcct aactgctaca aatactctta ggaagagaaa ccagggagcc 1080
cctttgatga ttaattcacc ttccagtgtc tcggagggat tcccctaacc tcattcccca 1140
accacttcat tcttgaaagc tgtggccagc ttgttattta taacaaccta aatttggttc 1200
taggccgggc gcggtggctc acgcctgtaa tcccagcact ttgggaggct gaggcgggtg 1260
gatcacttga ggtcaggagt tcctaaccag cctggtcaac atggtgaaac cccgtctcta 1320
ctaaaaatac aaaaattagc cgggcatggt ggcgcgcacc tgtaatccca gctacttggg 1380
aggctgaggc aagagaattg cttgaaccca ggagatggaa gttgcagtga gctgatatca 1440
tgcccctgta ctccagcctg ggtgacagag caagactctg tctcaaaaaa taaaaataaa 1500
aataaatttg gttctaatag aactcagttt taactagaat ttattcaatt cctctgggaa 1560
tgttacattg tttgtctgtc ttcatagcag attttaattt tgaataaata aatgtatctt 1620
attcacatc 1629

<210> SEQ ID NO 20

-continued

<211> LENGTH: 1995
<212> TYPE: DNA
<213> ORGANISM: Homo sapiens

<400> SEQUENCE: 20
acaggggtga aggcccagag accagcagaa cggcatccca gccacgacgg ccactttgct 60
ctgtctgctc tccgccacgg ccctgctctg ttccctggga cacccccgcc cccacctcct 120
caggctgcct gatctgccca gctttccagc tttcctctgg attccggcct ctggtcatcc 180
ctccccaccc tctctccaag gccctctcct ggtctccctt cttctagaac cccttcctcc 240
acctccctct ctgcagaact tctcctttac cccccacccc ccaccactgc cccctttcct 300
tttctgacct ccttttggag ggctcagcgc tgcccagacc ataggagaga tgtgggaggc 360
tcagttcctg ggcttgctgt ttctgcagcc gctttgggtg gctccagtga agcctctcca 420
gccaggggct gaggtcccgg tggtgtgggc ccaggagggg gctcctgccc agctcccctg 480
cagccccaca atcccctcc aggatctcag ccttctgcga agagcagggg tcacttggca 540
gcatcagcca gacagtggcc cgcccgctgc cgcccccggc catcccctgg cccccggccc 600
tcacccggcg gcgccctcct cctgggggcc caggccccgc cgctacacgg tgctgagcgt 660
gggtcccgga ggcctgcgca gcgggaggct gcccctgcag ccccgcgtcc agctggatga 720
gcgcggccgg cagcgcgggg acttctcgct atggctgcgc ccagcccggc gcgcggacgc 780
cggcgagtac cgcgccgcgg tgcacctcag ggaccgcgcc ctctcctgcc gcctccgtct 840
gcgcctgggc caggcctcga tgactgccag ccccccagga tctctcagag cctccgactg 900
ggtcattttg aactgctcct tcagccgccc tgaccgccca gcctctgtgc attggttccg 960
gaaccggggc cagggccgag tccctgtccg ggagtccccc catcaccact tagcggaaag 1020
cttcctcttc ctgccccaag tcagccccat ggactctggg ccctggggct gcatcctcac 1080
ctacagagat ggcttcaacg tctccatcat gtataacctc actgttctgg gtctggagcc 1140
cccaactccc ttgacagtgt acgctggagc aggttccagg gtggggctgc cctgccgcct 1200
gcctgctggt gtggggaccc ggtctttcct cactgccaag tggactcctc ctgggggagg 1260
ccctgacctc ctggtgactg gagacaatgg cgactttacc cttcgactag aggatgtgag 1320
ccaggcccag gctgggacct acacctgcca tatccatctg caggaacagc agctcaatgc 1380
cactgtcaca ttggcaatca tcacagtgac tcccaaatcc tttgggtcac ctggatccct 1440
ggggaagctg ctttgtgagg tgactccagt atctggacaa gaacgctttg tgtggagctc 1500
tctggacacc ccatcccaga ggagtttctc aggaccttgg ctggaggcac aggaggccca 1560
gctcctttcc cagccttggc aatgccagct gtaccagggg gagaggcttc ttggagcagc 1620
agtgtacttc acagagctgt ctagcccagg tgcccaacgc tctgggagag ccccaggtgc 1680
cctcccagca ggccacctcc tgctgtttct catccttggt gtcctttctc tgctcctttt 1740
ggtgactgga gcctttggct ttcacctttg gagaagacag tggcgaccaa gacgattttc 1800
tgccttagag caagggattc accctccgca ggctcagagc aagatagagg agctggagca 1860
agaaccggag ccggagccgg agccggaacc ggagcccgag cccgagcccg agccggagca 1920
gctctgacct ggagctgagg cagccagcag atctcagcag cccagtccaa ataaactccc 1980
tgtcagcagc aaaaa 1995

<210> SEQ ID NO 21
<211> LENGTH: 2448
<212> TYPE: DNA
<213> ORGANISM: Homo sapiens

<400> SEQUENCE: 21

```
agaacactta caggatgtgt gtagtgtggc atgacagaga actttggttt cctttaatgt     60
gactgtagac ctggcagtgt tactataaga atcactggca atcagacacc cgggtgtgct    120
gagctagcac tcagtggggg cggctactgc tcatgtgatt gtggagtaga cagttggaag    180
aagtacccag tccatttgga gagttaaaac tgtgcctaac agaggtgtcc tctgactttt    240
cttctgcaag ctccatgttt tcacatcttc cctttgactg tgtcctgctg ctgctgctgc    300
tactacttac aaggtcctca gaagtggaat acagagcgga ggtcggtcag aatgcctatc    360
tgccctgctt ctacacccca gccgccccag ggaacctcgt gcccgtctgc tggggcaaag    420
gagcctgtcc tgtgtttgaa tgtggcaacg tggtgctcag gactgatgaa agggatgtga    480
attattggac atccagatac tggctaaatg gggatttccg caaaggagat gtgtccctga    540
ccatagagaa tgtgactcta gcagacagtg ggatctactg ctgccggatc caaatcccag    600
gcataatgaa tgatgaaaaa tttaacctga agttggtcat caaaccagcc aaggtcaccc    660
ctgcaccgac tcggcagaga gacttcactg cagcctttcc aaggatgctt accaccaggg    720
gacatggccc agcagagaca cagacactgg ggagcctccc tgatataaat ctaacacaaa    780
tatccacatt ggccaatgag ttacgggact ctagattggc caatgactta cgggactctg    840
gagcaaccat cagaataggc atctacatcg gagcagggat ctgtgctggg ctggctctgg    900
ctcttatctt cggcgcttta attttcaaat ggtattctca tagcaaagag aagatacaga    960
atttaagcct catctctttg gccaacctcc ctccctcagg attggcaaat gcagtagcag   1020
agggaattcg ctcagaagaa aacatctata ccattgaaga gaacgtatat gaagtggagg   1080
agcccaatga gtattattgc tatgtcagca gcaggcagca accctcacaa cctttgggtt   1140
gtcgctttgc aatgccatag atccaaccac cttatttttg agcttggtgt tttgtctttt   1200
tcagaaacta tgagctgtgt cacctgactg gttttggagg ttctgtccac tgctatggag   1260
cagagttttc ccattttcag aagataatga ctcacatggg aattgaactg ggacctgcac   1320
tgaacttaaa caggcatgtc attgcctctg tatttaagcc aacagagtta cccaacccag   1380
agactgttaa tcatggatgt tagagctcaa acgggctttt atatacacta ggaattcttg   1440
acgtggggtc tctggagctc caggaaattc gggcacatca tatgtccatg aaacttcaga   1500
taaactaggg aaaactgggt gctgaggtga aagcataact tttttggcac agaaagtcta   1560
aaggggccac tgattttcaa agagatctgt gatccctttt tgtttttttgt ttttgagatg   1620
gagtcttgct ctgttgccca ggctggagtg caatggcaca atctcggctc actgcaagct   1680
ccgcctcctg ggttcaagcg attctcctgc ctcagcctcc tgagtggctg ggattacagg   1740
catgcaccac catgcccagc taatttgttg tatttttagt agagacaggg tttcaccatg   1800
ttggccagtg tggtctcaaa ctcctgacct catgatttgc ctgcctcggc ctcccaaagc   1860
actgggatta caggcgtgag ccaccacatc cagccagtga tccttaaaag attaagagat   1920
gactggacca ggtctacctt gatcttgaag attcccttgg aatgttgaga tttaggctta   1980
tttgagcact gcctgcccaa ctgtcagtgc cagtgcatag cccttctttt gtctccctta   2040
tgaagactgc cctgcagggc tgagatgtgg caggagctcc cagggaaaaa cgaagtgcat   2100
ttgattggtg tgtattggcc aagttttgct tgttgtgtgc ttgaaagaaa atatctctga   2160
ccaacttctg tattcgtgga ccaaactgaa gctatatttt tcacagaaga agaagcagtg   2220
acggggacac aaattctgtt gcctggtgga aagaaggcaa aggccttcag caatctatat   2280
```

-continued

```
taccagcgct ggatcctttg acagagagtg gtccctaaac ttaaatttca agacggtata   2340

ggcttgatct gtcttgctta ttgttgcccc ctgcgcctag cacaattctg acacacaatt   2400

ggaacttact aaaaattttt ttttactgtt aaaaaaaaaa aaaaaaaa                2448


<210> SEQ ID NO 22
<211> LENGTH: 2207
<212> TYPE: DNA
<213> ORGANISM: Homo sapiens

<400> SEQUENCE: 22

cacttcctcc ccagacaggg gtagtgcgag gccgggcaca gccttcctgt gtggttttac     60

cgcccagaga gcgtcatgga cctggggaaa ccaatgaaaa gcgtgctggt ggtggctctc    120

cttgtcattt tccaggtatg cctgtgtcaa gatgaggtca cggacgatta catcggagac    180

aacaccacag tggactacac tttgttcgag tctttgtgct ccaagaagga cgtgcggaac    240

tttaaagcct ggttcctccc tatcatgtac tccatcattt gtttcgtggg cctactgggc    300

aatgggctgg tcgtgttgac ctatatctat ttcaagaggc tcaagaccat gaccgatacc    360

tacctgctca acctggcggt ggcagacatc ctcttcctcc tgacccttcc cttctgggcc    420

tacagcgcgg ccaagtcctg ggtcttcggt gtccactttt gcaagctcat ctttgccatc    480

tacaagatga gcttcttcag tggcatgctc ctacttcttt gcatcagcat tgaccgctac    540

gtggccatcg tccaggctgt ctcagctcac cgccaccgtg cccgcgtcct tctcatcagc    600

aagctgtcct gtgtgggcat ctggatacta gccacagtgc tctccatccc agagctcctg    660

tacagtgacc tccagaggag cagcagtgag caagcgatgc gatgctctct catcacagag    720

catgtggagg cctttatcac catccaggtg gcccagatgg tgatcggctt tctggtcccc    780

ctgctggcca tgagcttctg ttaccttgtc atcatccgca ccctgctcca ggcacgcaac    840

tttgagcgca acaaggccat caaggtgatc atcgctgtgg tcgtggtctt catagtcttc    900

cagctgccct acaatggggt ggtcctggcc cagacggtgg ccaacttcaa catcaccagt    960

agcacctgtg agctcagtaa gcaactcaac atcgcctacg acgtcaccta cagcctggcc   1020

tgcgtccgct gctgcgtcaa ccctttcttg tacgccttca tcggcgtcaa gttccgcaac   1080

gatctcttca agctcttcaa ggacctgggc tgcctcagcc aggagcagct ccggcagtgg   1140

tcttcctgtc ggcacatccg gcgctcctcc atgagtgtgg aggccgagac caccaccacc   1200

ttctccccat aggcgactct tctgcctgga ctagagggac ctctcccagg gtccctgggg   1260

tggggatagg gagcagatgc aatgactcag gacatccccc cgccaaaagc tgctcaggga   1320

aaagcagctc tcccctcaga gtgcaagccc ctgctccaga agatagcttc accccaatcc   1380

cagctacctc aaccaatgcc aaaaaaagac agggctgata agctaacacc agacagacaa   1440

cactgggaaa cagaggctat tgtcccctaa accaaaaact gaaagtgaaa gtccagaaac   1500

tgttcccacc tgctggagtg aaggggccaa ggagggtgag tgcaaggggc gtgggagtgg   1560

cctgaagagt cctctgaatg aaccttctgg cctcccacag actcaaatgc tcagaccagc   1620

tcttccgaaa accaggcctt atctccaaga ccagagatag tggggagact tcttggcttg   1680

gtgaggaaaa gcggacatca gctggtcaaa caaactctct gaacccctcc ctccatcgtt   1740

ttcttcactg tcctccaagc cagcgggaat ggcagctgcc acgccgccct aaaagcacac   1800

tcatcccctc acttgccgcg tcgccctccc aggctctcaa caggggagag tgtggtgttt   1860

cctgcaggcc aggccagctg cctccgcgtg atcaaagcca cactctgggc tccagagtgg   1920

ggatgacatg cactcagctc ttggctccac tgggatggga ggagaggaca agggaaatgt   1980
```

-continued

```
caggggcggg gagggtgaca gtggccgccc aaggcccacg agcttgttct ttgttctttg   2040

tcacagggac tgaaaacctc tcctcatgtt ctgctttcga ttcgttaaga gagcaacatt   2100

ttacccacac acagataaag ttttcccttg aggaaacaac agctttaaaa gaaaaagaaa   2160

aaaaaagtct ttggtaaatg gcaaaaaaaa aaaaaaaaaa aaaaaaa                 2207
```

<210> SEQ ID NO 23
<211> LENGTH: 5977
<212> TYPE: DNA
<213> ORGANISM: Homo sapiens

<400> SEQUENCE: 23

```
tgtctctctt acctccttga tgttcggcac tatttgtggc cggcgtggtg gaaggacaca     60

gtgaggttct cacccccgcc ccccgctcct cgctcccatc ccagttccat caaaacgaac    120

ccgggccagc gcaaggatct ccgagttgcg agtgtgctga ggctgggact gtcactcatt    180

ctccgatcag cgcgtgaacg cagctcggct gccgctggca ggaaacaatt ctgcaaaaat    240

aatcatactc agcctggcaa ttgtctgccc ctaggtctgt cgctcagccg ccgtccacac    300

tcgctgcagg ggggggggca cagaatttac cgcggcaaga acatccctcc cagccagcag    360

attacaatgc tgcaaactaa ggatctcatc tggactttgt ttttcctggg aactgcagtt    420

tctctgcagg tggatattgt tcccagccag ggggagatca gcgttggaga gtccaaattc    480

ttcttatgcc aagtggcagg agatgccaaa gataaagaca tctcctggtt ctcccccaat    540

ggagaaaagc tcaccccaaa ccagcagcgg atctcagtgg tgtggaatga tgattcctcc    600

tccaccctca ccatctataa cgccaacatc gacgacgccg gcatttacaa gtgtgtggtt    660

acaggcgagg atggcagtga gtcagaggcc accgtcaacg tgaagatctt tcagaagctc    720

atgttcaaga atgcgccaac cccacaggag ttccgggagg gggaagatgc cgtgattgtg    780

tgtgatgtgg tcagctccct cccaccaacc atcatctgga aacacaaagg ccgagatgtc    840

atcctgaaaa aagatgtccg attcatagtc ctgtccaaca actacctgca gatccggggc    900

atcaagaaaa cagatgaggg cacttatcgc tgtgagggca gaatcctggc acgggggggag   960

atcaacttca aggacattca ggtcattgtg aatgtgccac ctaccatcca ggccaggcag   1020

aatattgtga atgccaccgc caacctcggc cagtccgtca ccctggtgtg cgatgccgaa   1080

ggcttcccag agcccaccat gagctggaca aaggatgggg aacagataga gcaagaggaa   1140

gacgatgaga agtacatctt cagcgacgat agttcccagc tgaccatcaa aaaggtggat   1200

aagaacgacg aggctgagta catctgcatt gctgagaaca aggctggcga gcaggatgcg   1260

accatccacc tcaaagtctt tgcaaaaccc aaaatcacat atgtagagaa ccagactgcc   1320

atggaattag aggagcaggt cactcttacc tgtgaagcct ccggagaccc cattccctcc   1380

atcacctgga ggacttctac ccggaacatc agcagcgaag aaaagactct ggatgggcac   1440

atggtggtgc gtagccatgc ccgtgtgtcg tcgctgaccc tgaagagcat ccagtacact   1500

gatgccggag agtacatctg caccgccagc aacaccatcg gccaggactc ccagtccatg   1560

taccttgaag tgcaatatgc cccaaagcta cagggccctg tggctgtgta cacttgggag   1620

gggaaccagg tgaacatcac ctgcgaggta tttgcctatc ccagtgccac gatctcatgg   1680

tttcgggatg gccagctgct gccaagctcc aattacagca atatcaagat ctacaacacc   1740

ccctctgcca gctatctgga ggtgacccca gactctgaga atgattttgg gaactacaac   1800

tgtactgcag tgaaccgcat tgggcaggag tccttggaat tcatccttgt tcaagcagac   1860
```

-continued

```
acccccctctt caccatccat cgaccaggtg gagccatact ccagcacagc ccaggtgcag   1920
tttgatgaac cagaggccac aggtggggtg cccatcctca aatacaaagc tgagtggaga   1980
gcagttggtg aagaagtatg gcattccaag tggtatgatg ccaaggaagc cagcatggag   2040
ggcatcgtca ccatcgtggg cctgaagccc gaaacaacgt acgccgtaag gctggcggcg   2100
ctcaatggca aagggctggg tgagatcagc gcggcctccg agttcaagac gcagccagtc   2160
caaggggaac ccagtgcacc taagctcgaa gggcagatgg gagaggatgg aaactctatt   2220
aaagtgaacc tgatcaagca ggatgacggc ggctccccca tcagacacta tctggtcagg   2280
taccgagcgc tctcctccga gtggaaacca gagatcaggc tcccgtctgg cagtgaccac   2340
gtcatgctga agtccctgga ctggaatgct gagtatgagg tctacgtggt ggctgagaac   2400
cagcaaggaa aatccaaggc ggctcatttt gtgttcagga cctcggccca gcccacagcc   2460
atcccagcca acggcagccc cacctcaggc ctgagcaccg gggccatcgt gggcatcctc   2520
atcgtcatct tcgtcctgct cctggtggtt gtggacatca cctgctactt cctgaacaag   2580
tgtggcctgt tcatgtgcat tgcggtcaac ctgtgtggaa aagccgggcc cggggccaag   2640
ggcaaggaca tggaggaggg caaggccgcc ttctcgaaag atgagtccaa ggagcccatc   2700
gtggaggttc gaacggagga ggagaggacc ccaaaccatg atggagggaa acacacagag   2760
cccaacgaga ccacgccact gacggagccc gagaagggcc ccgtagaagc aaagccagag   2820
tgccaggaga cagaaacgaa gccagcgcca gccgaagtca agacggtccc caatgacgcc   2880
acacagacaa aggagaacga gagcaaagca tgatgggtga agagaaccga gcaaagatca   2940
aaataaaaag tgacacagca gcttcaccag agcatttcca acaccacaga cacacacacg   3000
cacgcacaca cacaaacaca catgcacaca cacacatctc atttctctag tgtcttttgc   3060
ctttaaaaaa aactaaacag ataaaacatg ggaatctcct ttttgtaggt ttatagaaag   3120
ggtccctttg ttgcacactc acttgtaaga aaatgagaca aaaaggttaa acccacagcc   3180
aaactaggac actccgttcc ctgaaaccgt taaaaaatca aacaaaagga ccccaaatta   3240
agaatctagg aagctcagaa acgaaatcta ggttcaggaa gaccacactt ggtgttaccc   3300
gattggcaca gaccagtttc agagaaatac tttcaggcac taagactaat cgaatgaaca   3360
aagtccacag tttattttta tactttcagt caagtttgaa ctctgtaaaa cctcataaat   3420
aagttataat ttctgttcac tttgtatttg ttcagtatgc aaagtgtgtc accctttcta   3480
gctgaattca attcccacgt agactcttat tttataggac gaatgccaaa ttgcagcttc   3540
tgggggtaga tctcaatttg cagtattcag acttcttttt ctttctttta cattcttttt   3600
tctttctttc tttctgccaa ctttgttttc cagtgtttac aaggtgacaa atgtttgact   3660
ttggttgtgt ttaaatgtcc gtgtaaaata gctgcctttt attttttaag gtaacaaata   3720
ccacctagag gtaggtagga tcatcccacg cttgctttag cacaggacaa ctttacaaaa   3780
catgattgtt tacagctgct cttcccctct tttctgatct gcagtttttg cctgggtccc   3840
actcaggtga aaatccatct cattctggaa tggttttgct tttgaatttt tggttatttt   3900
tgtgtttctt tgggggttag accactttct gattagccgc cacctgcctg catctgtgaa   3960
aagggatctg ctcccaggcg ttctcaccct tcttttgaag gactccttag gctttgttga   4020
atgaagcaga gaagattgta tagttggggc tggtcttggt gaacacacat tattacccca   4080
cacatcccct ttgtgtagaa agccaaataa aatctataca taccatttcc ttttgagccc   4140
agaatctaga tttgagcgga agagcatgtg tgcttcaggg aattagtgtc tttttttgga   4200
aatctgttga agtaaagtaa catcggcctt ctgttcactt aggcagcatt tatagaaaca   4260
```

-continued aaagaagaaa gaaacaacct actgtctgga gtcataacac aactttcctg gattggaaac 4320
caagtggggg aaaaaataca gaaactttaa gggggatggg aggggggga gaagggaaaa 4380 gccagccctt tgtatagaaa ttttgctttt ttttccctca ttctacttta gaactgcaag 4440
cttgtgcact gtggatgcgt gaatatttta gtgtgaaacg tgtttttgtc atagtattga 4500
aataaaactt caacatagtt tggttgtgga aggtatagca gatagttcag aaaaaatatt 4560
caggaaacaa aaatcactca aacggaatcg aagcctttta acaaagaaaa tgaaatacag 4620
atgatgatga tgatgatgaa gatgatgcta agtaaacaga aatcagtact ccgcatgcgc 4680
tcctctccta aggtacaaag cagcaagagg ttagggtggc aaggctgcct ctgggtccat 4740
tctgtgggcc actctcccca acgttctgac acttctgcag tctgatcagt ggcgatgcta 4800
gattataatt tcaaactgtg aagaataatg gtcttgtcat ttgctcaatg tggggttatg 4860
ttgcattttc tcagctcctg gggatggaaa tggaggatcc cagaacacac agccctggcc 4920
cctttgattc tagggcctgc acagatctct ggttcaaatg cacaggccct cagaatagag 4980
gaacatgaag agagatctta gagcacacag tagaatgtga gagcctgggt gtctgagacc 5040
gggagggccc agcagtgagg ggcaggctct tctggtcacc aggctgttca gtggactcag 5100
ttcttcatct tgtaatgtcg atggctttgc cacaccaggc caagcccatg ccataccttg 5160
tcaagactgt caaagtggtt gtggttaggt caaactggtt ttggttctga tggttaggaa 5220
gaaacaggtc agccctcaga tcacctggcc cgggacagct gaccccctag aaccctggct 5280
ctgccattag ctaggaccta agactctgcc cacattttgg tctgttctct cccattacac 5340
ataggtttgt ctcagcatgc aagagttttt cctttaaaaa aaaaaaaaaa aaaaaaaaaa 5400
aagcaatgct ttctctaaaa tcaaagaggg agtcatttta ttccaagatg ttttatcttt 5460
tatgttaaga gatcaaagct tataattttc ttttttaatt tttgaaggag ggatcaactc 5520
cagtttccaa tgtctatgtg tctatgtgtg tatgtgccat acatatgtat tcacatgaag 5580
accggcatgg ccaagttctg ctggaggagc actcaagtgt gacgagcagg gccactggac 5640
cctgcagggc tgtggtgtat atagtgcagc tttggaggtg gaactctatt ttcacacttt 5700
tctatggagc cttccgagtc ccaggttttc acttgaggct gtctgtctgg atggcggttt 5760
tcagacctcc attaacatcc ctacccagca ttctgtactt cgggggcctt ctctcttgtt 5820
ataaaacttt ttaccaagtg aaacatcgat accacctttg tttccattct cactggtgta 5880
aatactgagt actaactgag aattttgact ttgcattctg tcggaatact tgtgttcaat 5940
aaaaattgaa agaaaaaagc taaaaaaaaa aaaaaaa 5977

<210> SEQ ID NO 24
<211> LENGTH: 1914
<212> TYPE: DNA
<213> ORGANISM: Homo sapiens

<400> SEQUENCE: 24
ccaaccacaa gcaccaaagc agaggggcag gcagcacacc acccagcagc cagagcacca 60
gcccagccat ggtccttgag gggtccctgg gccgatggga tcacgcagaa gaatgcgaga 120
gaagcagcct ttgagaaggg aagtcactat cccagagccc aggctgagcg gatggagttg 180
aggaagtacg gccctggaag actggcgggg acagttatag gaggagctgc tcagagtaaa 240
tcacagacta aatcagactc aatcacaaaa gagttcctgc caggccttta cacagcccct 300
tcctccccgt tcccgccctc acaggtgagt gaccaccaag tgctaaatga cgccgaggtt 360

-continued

```
gccgccctcc tggagaactt cagctcttcc tatgactatg gagaaaacga gagtgactcg    420

tgctgtacct ccccgccctg cccacaggac ttcagcctga acttcgaccg ggccttcctg    480

ccagccctct acagcctcct ctttctgctg gggctgctgg gcaacggcgc ggtggcagcc    540

gtgctgctga gccggcggac agccctgagc agcaccgaca ccttcctgct ccacctagct    600

gtagcagaca cgctgctggt gctgacactg ccgctctggg cagtggacgc tgccgtccag    660

tgggtctttg gctctggcct ctgcaaagtg gcaggtgccc tcttcaacat caacttctac    720

gcaggagccc tcctgctggc ctgcatcagc tttgaccgct acctgaacat agttcatgcc    780

acccagctct accgccgggg gcccccggcc cgcgtgaccc tcacctgcct ggctgtctgg    840

gggctctgcc tgcttttcgc cctcccagac ttcatcttcc tgtcggccca ccacgacgag    900

cgcctcaacg ccacccactg ccaatacaac ttcccacagg tgggccgcac ggctctgcgg    960

gtgctgcagc tggtggctgg ctttctgctg cccctgctgg tcatggccta ctgctatgcc   1020

cacatcctgg ccgtgctgct ggtttccagg ggccagcggc gcctgcgggc catgcggctg   1080

gtggtggtgg tcgtggtggc ctttgccctc tgctggaccc cctatcacct ggtggtgctg   1140

gtggacatcc tcatggacct gggcgctttg gcccgcaact gtggccgaga aagcagggta   1200

gacgtggcca agtcggtcac ctcaggcctg ggctacatgc actgctgcct caacccgctg   1260

ctctatgcct ttgtaggggt caagttccgg gagcggatgt ggatgctgct cttgcgcctg   1320

ggctgcccca accagagagg gctccagagg cagccatcgt cttcccgccg ggattcatcc   1380

tggtctgaga cctcagaggc ctcctactcg ggcttgtgag gccggaatcc gggctcccct   1440

ttcgcccaca gtctgacttc cccgcattcc aggctcctcc ctccctctgc cggctctggc   1500

tctccccaat atcctcgctc ccgggactca ctggcagccc cagcaccacc aggtctcccg   1560

ggaagccacc ctcccagctc tgaggactgc accattgctg ctccttagct gccaagcccc   1620

atcctgccgc ccgaggtggc tgcctggagc cccactgccc ttctcatttg gaaactaaaa   1680

cttcatcttc cccaagtgcg ggagtacaa ggcatggcgt agagggtgct gccccatgaa   1740

gccacagccc aggcctccag ctcagcagtg actgtggcca tggtccccaa gacctctata   1800

tttgctcttt tatttttatg tctaaaatcc tgcttaaaac ttttcaataa acaagatcgt   1860

caggaccaaa aaaaaaaaaa aaaaaaaaaa aaaaaaaaaa aaaaaaaaaa aaaa         1914
```

<210> SEQ ID NO 25
<211> LENGTH: 1193
<212> TYPE: DNA
<213> ORGANISM: Homo sapiens

<400> SEQUENCE: 25

```
gtctacaccc cctcctcaca cgcacttcac ctgggtcggg attctcaggt catgaacggt     60

cccagccacc tccgggcagg gcgggtgagg acggggacgg ggcgtgtcca actggctgtg    120

ggctcttgaa acccgagcat ggcacagcac ggggcgatgg gcgcgtttcg ggccctgtgc    180

ggcctggcgc tgctgtgcgc gctcagcctg ggtcagcgcc ccaccggggg tcccgggtgc    240

ggccctgggc gcctcctgct tgggacggga acggacgcgc gctgctgccg ggttcacacg    300

acgcgctgct gccgcgatta cccgggcgag gagtgctgtt ccgagtggga ctgcatgtgt    360

gtccagcctg aattccactg cggagaccct tgctgcacga cctgccggca ccacccttgt    420

cccccaggcc agggggtaca gtcccagggg aaattcagtt ttggcttcca gtgtatcgac    480

tgtgcctcgg ggaccttctc cgggggccac gaaggccact gcaaaccttg gacagactgc    540

acccagttcg ggtttctcac tgtgttccct gggaacaaga cccacaacgc tgtgtgcgtc    600
```

-continued ccagggtccc cgccggcaga gccgcttggg tggctgaccg tcgtcctcct ggccgtggcc 660
gcctgcgtcc tcctcctgac ctcggcccag cttggactgc acatctggca gctgaggaag 720
acccagctgc tgctggaggt gccgccgtcg accgaagacg ccagaagctg ccagttcccc 780
gaggaagagc ggggcgagcg atcggcagag gagaaggggc ggctgggaga cctgtgggtg 840
tgagcctggc cgtcctccgg ggccaccgac cgcagccagc ccctccccag gagctcccca 900
ggccgcaggg gctctgcgtt ctgctctggg ccgggccctg ctcccctggc agcagaagtg 960
ggtgcaggaa ggtggcagtg accagcgccc tggaccatgc agttcggcgg ccgcggctgg 1020 gcccctgcagg agggagagag agacacagtc atggcccccct tcctcccttg ctggccctga 1080
tggggtgggg tcttaggacg ggaggctgtg tccgtgggtg tgcagtgccc agcacgggac 1140
ccggctgcag gggaccttca ataaacactt gtccagtgaa aaaaaaaaaa aaa 1193

<210> SEQ ID NO 26
<211> LENGTH: 2292
<212> TYPE: DNA
<213> ORGANISM: Homo sapiens

<400> SEQUENCE: 26
gcacacactc atcgaaaaaa atttggatta ttagaagaga gaggtctgcg gcttccacac 60
cgtacagcgt ggtttttctt ctcggtataa aagcaaagtt gtttttgata cgtgacagtt 120
tcccacaagc caggctgatc cttttctgtc agtccacttc accaagcctg cccttggaca 180
aggacccgat gcccaacccc aggcctggca agccctcggc cccttccttg gcccttggcc 240
catccccagg agcctcgccc agctggaggg ctgcacccaa agcctcagac ctgctggggg 300
cccggggccc agggggaacc ttccagggcc gagatcttcg aggcggggcc catgcctcct 360
cttcttcctt gaaccccatg ccaccatcgc agctgcagct ctcaacggtg gatgcccacg 420
cccggacccc tgtgctgcag gtgcaccccc tggagagccc agccatgatc agcctcacac 480
cacccaccac cgccactggg gtcttctccc tcaaggcccg gcctggcctc ccacctggga 540
tcaacgtggc cagcctggaa tgggtgtcca gggagccggc actgctctgc accttcccaa 600
atcccagtgc acccaggaag gacagcaccc tttcggctgt gccccagagc tcctacccac 660
tgctggcaaa tggtgtctgc aagtggcccg gatgtgagaa ggtcttcgaa gagccagagg 720
acttcctcaa gcactgccag gcggaccatc ttctggatga gaagggcagg gcacaatgtc 780
tcctccagag agagatggta cagtctctgg agcagcagct ggtgctggag aaggagaagc 840
tgagtgccat gcaggcccac ctggctggga aaatggcact gaccaaggct tcatctgtgg 900
catcatccga caagggctcc tgctgcatcg tagctgctgg cagccaaggc cctgtcgtcc 960
cagcctggtc tggcccccgg gaggcccctg acagcctgtt tgctgtccgg aggcacctgt 1020
ggggtagcca tggaaacagc acattcccag agttcctcca caacatggac tacttcaagt 1080
tccacaacat gcgaccccct ttcacctacg ccacgctcat ccgctgggcc atcctggagg 1140
ctccagagaa gcagcggaca ctcaatgaga tctaccactg gttcacacgc atgtttgcct 1200
tcttcagaaa ccatcctgcc acctggaaga acgccatccg ccacaacctg agtctgcaca 1260
agtgctttgt gcgggtggag agcgagaagg gggctgtgtg gaccgtggat gagctggagt 1320
tccgcaagaa acggagccag aggcccagca ggtgttccaa ccctacacct ggcccctgac 1380
ctcaagatca aggaaaggag gatggacgaa caggggccaa actggtggga ggcagaggtg 1440
gtgggggcag ggatgatagg ccctggatgt gcccacaggg accaagaagt gaggtttcca 1500

-continued

```
ctgtcttgcc tgccagggcc cctgttcccc cgctggcagc cacccccctcc cccatcatat   1560

cctttgcccc aaggctgctc agaggggccc cggtcctggc cccagccccc acctccgccc   1620

cagacacacc ccccagtcga gccctgcagc caaacagagc cttcacaacc agccacacag   1680

agcctgcctc agctgctcgc acagattact tcagggctgg aaaagtcaca cagacacaca   1740

aaatgtcaca atcctgtccc tcactcaaca caaaccccaa aacacagaga gcctgcctca   1800

gtacactcaa acaacctcaa agctgcatca tcacacaatc acacacaagc acagccctga   1860

caacccacac accccaaggc acgcacccac agccagcctc agggcccaca ggggcactgt   1920

caacacaggg gtgtgcccag aggcctacac agaagcagcg tcagtaccct caggatctga   1980

ggtcccaaca cgtgctcgct cacacacacg gcctgttaga attcacctgt gtatctcacg   2040

catatgcaca cgcacagccc cccagtgggt ctcttgagtc ccgtgcagac acacacagcc   2100

acacacactg ccttgccaaa aataccccgt gtctcccctg ccactcacct cactcccatt   2160

ccctgagccc tgatccatgc ctcagcttag actgcagagg aactactcat ttatttggga   2220

tccaaggccc ccaacccaca gtaccgtccc caataaactg cagccgagct ccccacaaaa   2280

aaaaaaaaaa aa                                                       2292
```

<210> SEQ ID NO 27
<211> LENGTH: 12507
<212> TYPE: DNA
<213> ORGANISM: Homo sapiens

<400> SEQUENCE: 27

```
taccgggcgg aggtgagcgc ggcgccggct cctcctgcgg cggactttgg gtgcgacttg     60

acgagcggtg gttcgacaag tggccttgcg ggccggatcg tcccagtgga agagttgtaa    120

atttgcttct ggccttcccc tacggattat acctggcctt cccctacgga ttatactcaa    180

cttactgttt agaaaatgtg gcccacgaga cgcctggtta ctatcaaaag gagcggggtc    240

gacggtcccc actttcccct gagcctcagc acctgcttgt ttggaagggg tattgaatgt    300

gacatccgta tccagcttcc tgttgtgtca aaacaacatt gcaaaattga aatccatgag    360

caggaggcaa tattacataa tttcagttcc acaaatccaa cacaagtaaa tgggtctgtt    420

attgatgagc ctgtacggct aaaacatgga gatgtaataa ctattattga tcgttccttc    480

aggtatgaaa atgaaagtct tcagaatgga aggaagtcaa ctgaatttcc aagaaaaata    540

cgtgaacagg agccagcacg tcgtgtctca agatctagct tctcttctga ccctgatgag    600

aaagctcaag attccaaggc ctattcaaaa atcactgaag gaaaagtttc aggaaatcct    660

caggtacata tcaagaatgt caaagaagac agtaccgcag atgactcaaa agacagtgtt    720

gctcagggaa caactaatgt tcattcctca gaacatgctg gacgtaatgg cagaaatgca    780

gctgatccca tttctgggga ttttaaagaa atttccagcg ttaaattagt gagccgttat    840

ggagaattga agtctgttcc cactacacaa tgtcttgaca atagcaaaaa aaatgaatct    900

ccccttttgga agctttatga gtcagtgaag aaagagttgg atgtaaaatc acaaaaagaa    960

aatgtcctac agtattgtag aaaatctgga ttacaaactg attacgcaac agagaaagaa   1020

agtgctgatg gtttacaggg ggagacccaa ctgttggtct cgcgtaagtc aagaccaaaa   1080

tctggtggga gcggccacgc tgtggcagag cctgcttcac ctgaacaaga gcttgaccag   1140

aacaagggga agggaagaga cgtggagtct gttcagactc ccagcaaggc tgtgggcgcc   1200

agctttcctc tctatgagcc ggctaaaatg aagacccctg tacaatattc acagcaacaa   1260

aattctccac aaaaacataa gaacaaagac ctgtatacta ctggtagaag agaatctgtg   1320
```

aatctgggta aaagtgaagg cttcaaggct ggtgataaaa ctcttactcc caggaagctt 1380
tcaactagaa atcgaacacc agctaaagtt gaagatgcag ctgactctgc cactaagcca 1440
gaaaatctct cttccaaaac cagaggaagt attcctacag atgtggaagt tctgcctacg 1500
gaaactgaaa ttcacaatga gccatttttta actctgtggc tcactcaagt tgagaggaag 1560
atccaaaagg attccctcag caagcctgag aaattgggca ctacagctgg acagatgtgc 1620
tctgggttac ctggtcttag ttcagttgat atcaacaact ttggtgattc cattaatgag 1680
agtgagggaa tacctttgaa aagaaggcgt gtgtcctttg gtgggcacct aagacctgaa 1740
ctatttgatg aaaacttgcc tcctaatacg cctctcaaaa ggggagaagc cccaaccaaa 1800
agaaagtctc tggtaatgca cactccacct gtcctgaaga aaatcatcaa ggaacagcct 1860
caaccatcag gaaaacaaga gtcaggttca gaaatccatg tggaagtgaa ggcacaaagc 1920
ttggttataa gccctccagc tcctagtcct aggaaaactc cagttgccag tgatcaacgc 1980
cgtaggtcct gcaaaacagc ccctgcttcc agcagcaaat ctcagacaga ggttcctaag 2040
agaggaggga gaaagagtgg caacctgcct tcaaagagag tgtctatcag ccgaagtcaa 2100
catgatattt tacagatgat atgttccaaa agaagaagtg gtgcttcgga agcaaatctg 2160
attgttgcaa aatcatgggc agatgtagta aaacttggtg caaaacaaac acaaactaaa 2220
gtcataaaac atggtcctca aaggtcaatg aacaaaaggc aaagaagacc tgctactcca 2280
aagaagcctg tgggcgaagt tcacagtcaa tttagtacag gccacgcaaa ctctccttgt 2340
accataataa tagggaaagc tcatactgaa aaagtacatg tgcctgctcg accctacaga 2400
gtgctcaaca acttcatttc caaccaaaaa atggacttta aggaagatct ttcaggaata 2460
gctgaaatgt tcaagacccc agtgaaggag caaccgcagt tgacaagcac atgtcacatc 2520
gctatttcaa attcagagaa tttgcttgga aaacagtttc aaggaactga ttcaggagaa 2580
gaacctctgc tccccacctc agagagtttt ggaggaaatg tgttcttcag tgcacagaat 2640
gcagcaaaac agccatctga taaatgctct gcaagccctc ccttaagacg gcagtgtatt 2700
agagaaaatg gaaacgtagc aaaaaacgcc aggaacacct acaaaatgac ttctctggag 2760
acaaaaaactt cagatactga gacagagcct tcaaaaacag tatccactgc aaacaggtca 2820
ggaaggtcta cagagttcag gaatatacag aagctacctg tggaaagtaa gagtgaagaa 2880
acaaatacag aaattgttga gtgcatccta aaaagaggtc agaaggcaac actactacaa 2940
caaaggagag aaggagagat gaaggaaata gaaagacctt ttgagacata taaggaaaat 3000
attgaattaa aagaaaacga tgaaaagatg aaagcaatga agagatcaag aacttggggg 3060
cagaaatgtg caccaatgtc tgacctgaca gacctcaaga gcttgcctga tacagaactc 3120
atgaaagaca cggcacgtgg ccagaatctc ctccaaaccc aagatcatgc caaggcacca 3180
aagagtgaga aaggcaaaat cactaaaatg ccctgccagt cattacaacc agaaccaata 3240
aacaccccaa cacacacaaa acaacagttg aaggcatccc tggggaaagt aggtgtgaaa 3300
gaagagctcc tagcagtcgg caagttcaca cggacgtcag gggagaccac gcacacgcac 3360
agagagccag caggagatgg caagagcatc agaacgttta aggagtctcc aaagcagatc 3420
ctggacccag cagcccgtgt aactggaatg aagaagtggc caagaacgcc taaggaagag 3480
gcccagtcac tagaagacct ggctggcttc aaagagctct tccagacacc aggtccctct 3540
gaggaatcaa tgactgatga gaaaactacc aaaatagcct gcaaatctcc accaccagaa 3600
tcagtggaca ctccaacaag cacaaagcaa tggcctaaga gaagtctcag gaaagcagat 3660

-continued

```
gtagaggaag aattcttagc actcaggaaa ctaacaccat cagcagggaa agccatgctt   3720
acgcccaaac cagcaggagg tgatgagaaa gacattaaag catttatggg aactccagtg   3780
cagaaactgg acctggcagg aactttacct ggcagcaaaa gacagctaca gactcctaag   3840
gaaaaggccc aggctctaga agacctggct ggctttaaag agctcttcca gactcctggt   3900
cacaccgagg aattagtggc tgctggtaaa accactaaaa taccctgcga ctctccacag   3960
tcagacccag tggacacccc aacaagcaca aagcaacgac ccaagagaag tatcaggaaa   4020
gcagatgtag agggagaact cttagcgtgc aggaatctaa tgccatcagc aggcaaagcc   4080
atgcacacgc ctaaaccatc agtaggtgaa gagaaagaca tcatcatatt tgtgggaact   4140
ccagtgcaga aactggacct gacagagaac ttaaccggca gcaagagacg gccacaaact   4200
cctaaggaag aggcccaggc tctggaagac ctgactggct ttaaagagct cttccagacc   4260
cctggtcata ctgaagaagc agtggctgct ggcaaaacta ctaaaatgcc ctgcgaatct   4320
tctccaccag aatcagcaga caccccaaca agcacaagaa ggcagcccaa gacacctttg   4380
gagaaaaggg acgtacagaa ggagctctca gccctgaaga agctcacaca gacatcaggg   4440
gaaaccacac acacagataa agtaccagga ggtgaggata aaagcatcaa cgcgtttagg   4500
gaaactgcaa aacagaaact ggacccagca gcaagtgtaa ctggtagcaa gaggcaccca   4560
aaaactaagg aaaaggccca accccctagaa gacctggctg gcttgaaaga gctcttccag   4620
acaccagtat gcactgacaa gcccacgact cacgagaaaa ctaccaaaat agcctgcaga   4680
tcacaaccag acccagtgga cacaccaaca agctccaagc cacagtccaa gagaagtctc   4740
aggaaagtgg acgtagaaga agaattcttc gcactcagga aacgaacacc atcagcaggc   4800
aaagccatgc acacacccaa accagcagta agtggtgaga aaaacatcta cgcatttatg   4860
ggaactccag tgcagaaact ggacctgaca gagaacttaa ctggcagcaa gagacggcta   4920
caaactccta aggaaaaggc ccaggctcta gaagacctgg ctggctttaa agagctcttc   4980
cagacacgag gtcacactga ggaatcaatg actaacgata aaactgccaa agtagcctgc   5040
aaatcttcac aaccagaccc agacaaaaac ccagcaagct ccaagcgacg gctcaagaca   5100
tccctgggga aagtgggcgt gaaagaagag ctcctagcag ttggcaagct cacacagaca   5160
tcaggagaga ctacacacac acacacagag ccaacaggag atggtaagag catgaaagca   5220
tttatggagt ctccaaagca gatcttagac tcagcagcaa gtctaactgg cagcaagagg   5280
cagctgagaa ctcctaaggg aaagtctgaa gtccctgaag acctggccgg cttcatcgag   5340
ctcttccaga caccaagtca cactaaggaa tcaatgacta acgaaaaaac taccaaagta   5400
tcctacagag cttcacagcc agacctagtg gacaccccaa caagctccaa gccacagccc   5460
aagagaagtc tcaggaaagc agacactgaa gaagaatttt tagcatttag gaaacaaacg   5520
ccatcagcag gcaaagccat gcacacaccc aaaccagcag taggtgaaga gaaagacatc   5580
aacacgtttt tgggaactcc agtgcagaaa ctggaccagc caggaaattt acctggcagc   5640
aatagacggc tacaaactcg taaggaaaag gcccaggctc tagaagaact gactggcttc   5700
agagagcttt tccagacacc atgcactgat aaccccacga ctgatgagaa aactaccaaa   5760
aaaatactct gcaaatctcc gcaatcagac ccagcggaca ccccaacaaa cacaaagcaa   5820
cggcccaaga gaagcctcaa gaaagcagac gtagaggaag aatttttagc attcaggaaa   5880
ctaacaccat cagcaggcaa agccatgcac acgcctaaag cagcagtagg tgaagagaaa   5940
gacatcaaca catttgtggg gactccagtg gagaaactgg acctgctagg aaatttacct   6000
ggcagcaaga gacggccaca aactcctaaa gaaaaggcca aggctctaga agatctggct   6060
```

```
ggcttcaaag agctcttcca gacaccaggt cacactgagg aatcaatgac cgatgacaaa   6120
atcacagaag tatcctgcaa atctccacaa ccagacccag tcaaaacccc aacaagctcc   6180
aagcaacgac tcaagatatc cttggggaaa gtaggtgtga aagaagaggt cctaccagtc   6240
ggcaagctca cacagacgtc agggaagacc acacagacac acagagagac agcaggagat   6300
ggaaagagca tcaaagcgtt taaggaatct gcaaagcaga tgctggaccc agcaaactat   6360
ggaactggga tggagaggtg gccaagaaca cctaaggaag aggcccaatc actagaagac   6420
ctggccggct tcaaagagct cttccagaca ccagaccaca ctgaggaatc aacaactgat   6480
gacaaaacta ccaaaatagc ctgcaaatct ccaccaccag aatcaatgga cactccaaca   6540
agcacaagga ggcggcccaa aacacctttg ggaaaaggg atatagtgga agagctctca   6600
gccctgaagc agctcacaca gaccacacac acagacaaag taccaggaga tgaggataaa   6660
ggcatcaacg tgttcaggga aactgcaaaa cagaaactgg acccagcagc aagtgtaact   6720
ggtagcaaga ggcagccaag aactcctaag ggaaaagccc aacccctaga agacttggct   6780
ggcttgaaag agctcttcca gacaccaata tgcactgaca agcccacgac tcatgagaaa   6840
actaccaaaa tagcctgcag atctccacaa ccagacccag tgggtacccc aacaatcttc   6900
aagccacagt ccaagagaag tctcaggaaa gcagacgtag aggaagaatc cttagcactc   6960
aggaaacgaa caccatcagt agggaaagct atggacacac ccaaaccagc aggaggtgat   7020
gagaaagaca tgaaagcatt tatgggaact ccagtgcaga aattggacct gccaggaaat   7080
ttacctggca gcaaaagatg gccacaaact cctaaggaaa aggcccaggc tctagaagac   7140
ctggctggct tcaaagagct cttccagaca ccaggcactg acaagcccac gactgatgag   7200
aaaactacca aaatagcctg caaatctcca caaccagacc cagtggacac cccagcaagc   7260
acaaagcaac ggcccaagag aaacctcagg aaagcagacg tagaggaaga atttttagca   7320
ctcaggaaac gaacaccatc agcaggcaaa gccatggaca caccaaaacc agcagtaagt   7380
gatgagaaaa atatcaacac atttgtggaa actccagtgc agaaactgga cctgctagga   7440
aatttacctg gcagcaagag acagccacag actcctaagg aaaaggctga ggctctagag   7500
gacctggttg gcttcaaaga actcttccag acaccaggtc acactgagga atcaatgact   7560
gatgacaaaa tcacagaagt atcctgtaaa tctccacagc cagagtcatt caaaacctca   7620
agaagctcca agcaaaggct caagataccc ctggtgaaag tggacatgaa agaagagccc   7680
ctagcagtca gcaagctcac acggacatca ggggagacta cgcaaacaca cacagagcca   7740
acaggagata gtaagagcat caaagcgttt aaggagtctc caaagcagat cctggaccca   7800
gcagcaagtg taactggtag caggaggcag ctgagaactc gtaaggaaaa ggcccgtgct   7860
ctagaagacc tggttgactt caaagagctc ttctcagcac caggtcacac tgaagagtca   7920
atgactattg acaaaaacac aaaaattccc tgcaaatctc cccccaccaga actaacagac   7980
actgccacga gcacaaagag atgccccaag acacgtccca ggaaagaagt aaaagaggag   8040
ctctcagcag ttgagaggct cacgcaaaca tcagggcaaa gcacacacac acacaaagaa   8100
ccagcaagcg gtgatgaggg catcaaagta ttgaagcaac gtgcaaagaa gaaaccaaac   8160
ccagtagaag aggaacccag caggagaagg ccaagagcac ctaaggaaaa ggcccaaccc   8220
ctggaagacc tggccggctt cacagagctc tctgaaacat caggtcacac tcaggaatca   8280
ctgactgctg gcaaagccac taaaataccc tgcgaatctc cccactaga agtggtagac   8340
accacagcaa gcacaaagag gcatctcagg acacgtgtgc agaaggtaca agtaaaagaa   8400
```

-continued

```
gagccttcag cagtcaagtt cacacaaaca tcaggggaaa ccacggatgc agacaaagaa   8460
ccagcaggtg aagataaagg catcaaagca ttgaaggaat ctgcaaaaca gacaccggct   8520
ccagcagcaa gtgtaactgg cagcaggaga cggccaagag cacccaggga aagtgcccaa   8580
gccatagaag acctagctgg cttcaaagac ccagcagcag gtcacactga agaatcaatg   8640
actgatgaca aaaccactaa aataccctgc aaatcatcac cagaactaga agacaccgca   8700
acaagctcaa agagacggcc caggacacgt gcccagaaag tagaagtgaa ggaggagctg   8760
ttagcagttg gcaagctcac acaaacctca ggggagacca cgcacaccga caaagagccg   8820
gtaggtgagg gcaaaggcac gaaagcattt aagcaacctg caaagcggaa gctggacgca   8880
gaagatgtaa ttggcagcag gagacagcca agagcaccta aggaaaaggc ccaacccctg   8940
gaagatctgg ccagcttcca agagctctct caaacaccag gccacactga ggaactggca   9000
aatggtgctg ctgatagctt tacaagcgct ccaaagcaaa cacctgacag tggaaaacct   9060
ctaaaaatat ccagaagagt tcttcgggcc cctaaagtag aacccgtggg agacgtggta   9120
agcaccagag accctgtaaa atcacaaagc aaaagcaaca cttccctgcc cccactgccc   9180
ttcaagaggg gaggtggcaa agatggaagc gtcacgggaa ccaagaggct gcgctgcatg   9240
ccagcaccag aggaaattgt ggaggagctg ccagccagca agaagcagag ggttgctccc   9300
agggcaagag gcaaatcatc cgaacccgtg gtcatcatga agagaagttt gaggacttct   9360
gcaaaaagaa ttgaacctgc ggaagagctg aacagcaacg acatgaaaac caacaaagag   9420
gaacacaaat tacaagactc ggtccctgaa aataagggaa tatccctgcg ctccagacgc   9480
caaaataaga ctgaggcaga acagcaaata actgaggtct ttgtattagc agaaagaata   9540
gaaataaaca gaaatgaaaa gaagcccatg aagacctccc cagagatgga cattcagaat   9600
ccagatgatg gagcccggaa acccatacct agagacaaag tcactgagaa caaaaggtgc   9660
ttgaggtctg ctagacagaa tgagagctcc cagcctaagg tggcagagga gagcggaggg   9720
cagaagagtg cgaaggttct catgcagaat cagaaaggga aaggagaagc aggaaattca   9780
gactccatgt gcctgagatc aagaaagaca aaaagccagc ctgcagcaag cactttggag   9840
agcaaatctg tgcagagagt aacgcggagt gtcaagaggt gtgcagaaaa tccaaagaag   9900
gctgaggaca atgtgtgtgt caagaaaata agaaccagaa gtcataggga cagtgaagat   9960
atttgacaga aaaatcgaac tgggaaaaat ataataaagt tagttttgtg ataagttcta  10020
gtgcagtttt tgtcataaat tacaagtgaa ttctgtaagt aaggctgtca gtctgcttaa  10080
gggaagaaaa ctttggattt gctgggtctg aatcggcttc ataaactcca ctgggagcac  10140
tgctgggctc ctggactgag aatagttgaa caccgggggc tttgtgaagg agtctgggcc  10200
aaggtttgcc ctcagctttg cagaatgaag ccttgaggtc tgtcaccacc cacagccacc  10260
ctacagcagc cttaactgtg acacttgcca cactgtgtcg tcgtttgttt gcctatgtcc  10320
tccagggcac ggtggcagga acaactatcc tcgtctgtcc caacactgag caggcactcg  10380
gtaaacacga atgaatggat gagcgcacgg atgaatggag cttacaagat ctgtctttcc  10440
aatggccggg ggcatttggt ccccaaatta aggctattgg acatctgcac aggacagtcc  10500
tatttttgat gtcctttcct ttctgaaaat aaagttttgt gctttggaga atgactcgtg  10560
agcacatctt tagggaccaa gagtgacttt ctgtaaggag tgactcgtgg cttgccttgg  10620
tctcttggga atacttttct aactagggtt gctctcacct gagacattct ccacccgcgg  10680
aatctcaggg tcccaggctg tgggccatca cgacctcaaa ctggctccta atctccagct  10740
ttcctgtcat tgaaagcttc ggaagtttac tggctctgct cccgcctgtt ttctttctga  10800
```

ctctatctgg cagcccgatg ccacccagta caggaagtga caccagtact ctgtaaagca 10860
tcatcatcct tggagagact gagcactcag caccttcagc cacgatttca ggatcgcttc 10920
cttgtgagcc gctgcctccg aaatctcctt tgaagcccag acatctttct ccagcttcag 10980
acttgtagat ataactcgtt catcttcatt tactttccac tttgcccccct gtcctctctg 11040 tgttccccaa atcagagaat agcccgccat cccccaggtc acctgtctgg attcctcccc 11100
attcacccac cttgccaggt gcaggtgagg atggtgcacc agacagggta gctgtccccc 11160
aaaatgtgcc ctgtgcgggc agtgccctgt ctccacgttt gtttccccag tgtctggcgg 11220
ggagccaggt gacatcataa atacttgctg aatgaatgca gaaatcagcg gtactgactt 11280
gtactatatt ggctgccatg atagggttct cacagcgtca tccatgatcg taagggagaa 11340
tgacattctg cttgagggag ggaatagaaa ggggcaggga ggggacatct gagggcttca 11400
cagggctgca aagggtacag ggattgcacc agggcagaac aggggagggt gttcaaggaa 11460
gagtggctct tagcagaggc actttggaag gtgtgaggca taaatgcttc cttctacgta 11520
ggccaacctc aaaactttca gtaggaatgt tgctatgatc aagttgttct aacactttag 11580
acttagtagt aattatgaac ctcacataga aaaatttcat ccagccatat gcctgtggag 11640
tggaatattc tgtttagtag aaaaatcctt tagagttcag ctctaaccag aaatcttgct 11700
gaagtatgtc agcacctttt ctcaccctgg taagtacagt atttcaagag cacgctaagg 11760
gtggttttca ttttacaggg ctgttgatga tgggttaaaa atgttcattt aagggctacc 11820
cccgtgttta atagatgaac accacttcta cacaaccctc cttggtactg gggggaggggag 11880 agatctgaca aatactgccc attcccctag gctgactgga tttgagaaca aatacccacc 11940
catttccacc atggtatggt aacttctctg agcttcagtt tccaagtgaa tttccatgta 12000
ataggacatt cccattaaat acaagctgtt tttactttttt cgcctcccag ggcctgtggg 12060
atctggtccc ccagcctctc ttgggctttc ttacactaac tctgtaccta ccatctcctg 12120
cctcccttag gcaggcacct ccaaccacca cacactccct gctgttttcc ctgcctggaa 12180
ctttccctcc tgccccacca agatcatttc atccagtcct gagctcagct taagggaggc 12240
ttcttgcctg tgggttccct cacccccatg cctgtcctcc aggctggggc aggttcttag 12300
tttgcctgga attgttctgt acctctttgt agcacgtagt gttgtggaaa ctaagccact 12360
aattgagttt ctggctcccc tcctggggtt gtaagttttg ttcattcatg agggccgact 12420
gcatttcctg gttactctat cccagtgacc agccacagga gatgtccaat aaagtatgtg 12480
atgaaatggt cttaaaaaaa aaaaaaa 12507

<210> SEQ ID NO 28
<211> LENGTH: 2757
<212> TYPE: DNA
<213> ORGANISM: Homo sapiens

<400> SEQUENCE: 28
gacaagtact gagtgaactc aaaccctctg taaagtaaca gaagttagaa ggggaaatgt 60
cgcctctctg aagattaccc aaagaaaaag tgatttgtca ttgctttata gactgtaaga 120
agagaacatc tcagaagtgg agtcttaccc tgaaatcaaa ggatttaaag aaaaagtgga 180
atttttcttc agcaagctgt gaaactaaat ccacaacctt tggagaccca ggaacaccct 240
ccaatctctg tgtgttttgt aaacatcact ggagggtctt ctacgtgagc aattggattg 300
tcatcagccc tgcctgtttt gcacctggga agtgccctgg tcttacttgg gtccaaattg 360

-continued

```
ttggctttca cttttgaccc taagcatctg aagccatggg ccacacacgg aggcagggaa    420
catcaccatc caagtgtcca tacctcaatt tctttcagct cttggtgctg gctggtcttt    480
ctcacttctg ttcaggtgtt atccacgtga ccaaggaagt gaaagaagtg gcaacgctgt    540
cctgtggtca caatgtttct gttgaagagc tggcacaaac tcgcatctac tggcaaaagg    600
agaagaaaat ggtgctgact atgatgtctg ggacatgaa tatatggccc gagtacaaga    660
accggaccat ctttgatatc actaataacc tctccattgt gatcctggct ctgcgcccat    720
ctgacgaggg cacatacgag tgtgttgttc tgaagtatga aaaagacgct ttcaagcggg    780
aacacctggc tgaagtgacg ttatcagtca aagctgactt ccctacacct agtatatctg    840
actttgaaat tccaacttct aatattagaa ggataatttg ctcaacctct ggaggttttc    900
cagagcctca cctctcctgg ttggaaaatg gagaagaatt aaatgccatc aacacaacag    960
tttcccaaga tcctgaaact gagctctatg ctgttagcag caaactggat ttcaatatga   1020
caaccaacca cagcttcatg tgtctcatca agtatggaca tttaagagtg aatcagacct   1080
tcaactggaa tacaaccaag caagagcatt ttcctgataa cctgctccca tcctgggcca   1140
ttaccttaat ctcagtaaat ggaatttttg tgatatgctg cctgacctac tgctttgccc   1200
caagatgcag agagagaagg aggaatgaga gattgagaag ggaaagtgta cgccctgtat   1260
aacagtgtcc gcagaagcaa ggggctgaaa agatctgaag gtcccacctc catttgcaat   1320
tgacctcttc tgggaacttc ctcagatgga caagattacc ccaccttgcc ctttacgtat   1380
ctgctcttag gtgcttcttc acttcagttg ctttgcagga agtgtctaga ggaatatggt   1440
gggcacagaa gtagctctgg tgaccttgat caaggtgttt tgaaatgcag aattcttgag   1500
ttctggaagg gactttagag aataccagtg ttattaatga caaaggcact gaggcccagg   1560
gaggtgaccc gaattataaa ggccagcgcc agaacccaga tttcctaact ctggtgctct   1620
ttccctttat cagtttgact gtggcctgtt aactggtata tacatatata tgtcaggcaa   1680
agtgctgctg gaagtagaat ttgtccaata acaggtcaac ttcagagact atctgatttc   1740
ctaatgtcag agtagaagat tttatgctgc tgtttacaaa agcccaatgt aatgcatagg   1800
aagtatggca tgaacatctt taggagacta atggaaatat tattggtgtt tacccagtat   1860
tccatttttt tcattgtgtt ctctattgct gctctctcac tcccccatga ggtacagcag   1920
aaaggagaac tatccaaaac taatttcctc tgacatgtaa gacgaatgat ttaggtacgt   1980
caaagcagta gtcaaggagg aaagggatag tccaaagact taactggttc atattggact   2040
gataatctct ttaaatggct ttatgctagt ttgacctcat ttgtaaaata tttatgagaa   2100
agttctcatt taaaatgaga tcgttgttta cagtgtatgt actaagcagt aagctatctt   2160
caaatgtcta aggtagtaac tttccatagg gcctccttag atccctaaga tggctttttc   2220
tccttggtat ttctgggtct ttctgacatc agcagagaac tggaaagaca tagccaactg   2280
ctgttcatgt tactcatgac tcctttctct aaaactgcct tccacaattc actagaccag   2340
aagtggacgc aacttaagct gggataatca cattatcatc tgaaaatctg gagttgaaca   2400
gcaaaagaag acaacatttc tcaaatgcac atctcatggc agctaagcca catggctggg   2460
atttaaagcc tttagagcca gcccatggct ttagctacct cactatgctg cttcacaaac   2520
cttgctcctg tgtaaaacta tattctcagt gtagggcaga gaggtctaac accaacataa   2580
ggtactagca gtgtttcccg tattgacagg aatacttaac tcaataattc ttttcttttc   2640
catttagtaa cagttgtgat gactatgttt ctattctaag taattcctgt attctacagc   2700
agatactttg tcagcaatac taagggaaga aacaaagttg aaccgtttct ttaataa      2757
```

<210> SEQ ID NO 29
<211> LENGTH: 1240
<212> TYPE: DNA
<213> ORGANISM: Homo sapiens

<400> SEQUENCE: 29
cacattgttc tgatcatctg aagatcagct attagaagag aaagatcagt taagtccttt 60
ggacctgatc agcttgatac aagaactact gatttcaact tctttggctt aattctctcg 120
gaaacgatga aatatacaag ttatatcttg gcttttcagc tctgcatcgt tttgggttct 180
cttggctgtt actgccagga cccatatgta aaagaagcag aaaaccttaa gaaatatttt 240
aatgcaggtc attcagatgt agcggataat ggaactcttt tcttaggcat tttgaagaat 300
tggaaagagg agagtgacag aaaaataatg cagagccaaa ttgtctcctt ttacttcaaa 360
ctttttaaaa actttaaaga tgaccagagc atccaaaaga gtgtggagac catcaaggaa 420
gacatgaatg tcaagttttt caatagcaac aaaaagaaac gagatgactt cgaaaagctg 480
actaattatt cggtaactga cttgaatgtc caacgcaaag caatacatga actcatccaa 540
gtgatggctg aactgtcgcc agcagctaaa acagggaagc gaaaaaggag tcagatgctg 600
tttcgaggtc gaagagcatc ccagtaatgg ttgtcctgcc tgcaatattt gaattttaaa 660
tctaaatcta tttattaata tttaacatta tttatatggg gaatatattt ttagactcat 720
caatcaaata agtatttata atagcaactt ttgtgtaatg aaaatgaata tctattaata 780
tatgtattat ttataattcc tatatcctgt gactgtctca cttaatcctt tgttttctga 840
ctaattaggc aaggctatgt gattacaagg ctttatctca ggggccaact aggcagccaa 900
cctaagcaag atcccatggg ttgtgtgttt atttcacttg atgatacaat gaacacttat 960
aagtgaagtg atactatcca gttactgccg gtttgaaaat atgcctgcaa tctgagccag 1020
tgctttaatg gcatgtcaga cagaacttga atgtgtcagg tgaccctgat gaaaacatag 1080
catctcagga gatttcatgc ctggtgcttc caaatattgt tgacaactgt gactgtaccc 1140
aaatggaaag taactcattt gttaaaatta tcaatatcta atatatatga ataaagtgta 1200
agttcacaac aaaaaaaaaa aaaaaaaaaa aaaaaaaaaa 1240

<210> SEQ ID NO 30
<211> LENGTH: 1859
<212> TYPE: DNA
<213> ORGANISM: Homo sapiens

<400> SEQUENCE: 30
gcaggcacaa actcatccat ccccagttga ttggaagaaa caacgatgac tcctgggaag 60
acctcattgg tgtcactgct actgctgctg agcctggagg ccatagtgaa ggcaggaatc 120
acaatcccac gaaatccagg atgcccaaat tctgaggaca agaacttccc ccggactgtg 180
atggtcaacc tgaacatcca taaccggaat accaatacca atcccaaaag gtcctcagat 240
tactacaacc gatccacctc accttggaat ctccaccgca atgaggaccc tgagagatat 300
ccctctgtga tctgggaggc aaagtgccgc cacttgggct gcatcaacgc tgatgggaac 360
gtggactacc acatgaactc tgtccccatc cagcaagaga tcctggtcct gcgcagggag 420
cctccacact gccccaactc cttccggctg gagaagatac tggtgtccgt gggctgcacc 480
tgtgtcaccc cgattgtcca ccatgtggcc taagagctct ggggagccca cactccccaa 540
agcagttaga ctatggagag ccgacccagc ccctcaggaa ccctcatcct tcaaagacag 600
cctcatttcg gactaaactc attagagttc ttaaggcagt ttgtccaatt aaagcttcag 660
aggtaacact tggccaagat atgagatctg aattaccttt ccctctttcc aagaaggaag 720
gtttgactga gtaccaattt gcttcttgtt tactttttta agggctttaa gttatttatg 780
tatttaatat gccctgagat aactttgggg tataagattc cattttaatg aattacctac 840
tttattttgt ttgtcttttt aaagaagata agattctggg cttgggaatt ttattattta 900
aaaggtaaaa cctgtattta tttgagctat ttaaggatct atttatgttt aagtatttag 960
aaaaaggtga aaaagcacta ttatcagttc tgcctaggta aatgtaagat agaattaaat 1020
ggcagtgcaa aatttctgag tctttacaac atacggatat agtatttcct cctctttgtt 1080
tttaaaagtt ataacatggc tgaaaagaaa gattaaacct actttcatat gtattaattt 1140
aaattttgca atttgttgag gttttacaag agatacagca agtctaactc tctgttccat 1200
taaaccctta taataaaatc cttctgtaat aataaagttt caaaagaaaa tgtttatttg 1260
ttctcattaa atgtatttta gcaaactcag ctcttcccta ttgggaagag ttatgcaaat 1320
tctcctataa gcaaaacaaa gcatgtcttt gagtaacaat gacctggaaa tacccaaaat 1380
tccaagttct cgatttcaca tgccttcaag actgaacacc gactaaggtt ttcatactat 1440
tagccaatgc tgtagacaga agcattttga taggaataga gcaaataaga taatggccct 1500
gaggaatggc atgtcattat taaagatcat atggggaaaa tgaaaccctc cccaaaatac 1560
aagaagttct gggaggagac attgtcttca gactacaatg tccagtttct cccctagact 1620
caggcttcct ttggagatta aggcccctca gagatcaaca gaccaacatt tttctcttcc 1680
tcaagcaaca ctcctagggc ctggcttctg tctgatcaag gcaccacaca acccagaaag 1740
gagctgatgg ggcagaacga actttaagta tgagaaaagt tcagcccaag taaaataaaa 1800
actcaatcac attcaattcc agagtagttt caagtttcac atcgtaacca ttttcgccc 1859

<210> SEQ ID NO 31
<211> LENGTH: 3674
<212> TYPE: DNA
<213> ORGANISM: Homo sapiens

<400> SEQUENCE: 31
aagtttccaa gtggtcaact tgaccgatgc tttggcaatt gaaaaagggc agaaaggcgc 60
gggctagtgg gtggatgggg acaaagatct aagtcacctt cttccagcgt gtgagcctgg 120
gaggagggtg ggggtcctga ggagcaagag gtacgaggaa ggaaaaggag agggcttctg 180
ggttagtttc cacctcctgc tttccaactc acggcgcttt ccttccggaa aggacgctgg 240
attcagggcg cgccagtacg cgcagtagcg gcccgcgagt cggcaggtgg gtagccccgg 300
cgcgggagga aggggaagtt accttcccct cggaagaggg cgctggctcc cccatcctgc 360
ctttataata aggccaccgg aggagaggaa gcagccagct gccgtctgcg ctttgcaaag 420
catgcagtta ggggagcagc tcttggtgag ctcagtgaac ctgcctggcg cgcacttcta 480
cccgctggag agtgcgcgag gcggcagcgg cgggagcgct ggccacctcc ccagcgcggc 540
cccctctcct cagaagttgg acttagacaa agcgtccaag aagttttccg gcagtctctc 600
ctgcgaggcg gtgagcgggg agcccgcagc cgccagcgca ggggcccccg cggccatgct 660
tagtgacacc gacgccgggg acgcatttgc cagcgctgcg gcagtggcca agccggggcc 720
cccggacggc cgcaagggct ccccctgcgg ggaggaggag ctgccctccg ccgctgcagc 780
cgccgccgcc gccgccgccg cggctgcggc cactgcgcgc tactccatgg acagcctgag 840
ctccgagcgg tactacctcc agtcccccgg tcctcagggg tcggagctgg ctgcgccctg 900

-continued

```
ctcactcttc ccgtaccagg cggcggctgg ggcgccccac ggacctgtgt acccggctcc    960
taacggggcg cgctacccct acggctccat gctgcccccc ggcggcttcc ccgcggctgt   1020
gtgcccaccc gggagggcgc agttcggccc aggagccggt gcgggcagtg gcgcgggcgg   1080
tagcagcggc gggggcggcg gcccgggcac ctatcagtac agccaggggg ctccgctcta   1140
cgggccgtac cctggagccg cagcggcggg atcttgcgga ggactggggg gcctgggggt   1200
tccaggttct ggcttccgtg cccacgtcta cctgtgcaac cggcctctgt ggctcaaatt   1260
ccaccgccac caaactgaga tgatcattac gaaacagggc aggcgcatgt ttcctttctt   1320
gagcttcaac ataaacggac tcaatcccac tgcccactac aatgtgttcg tagaggtggt   1380
gctggcggac cccaaccact ggcgcttcca ggggggcaaa tgggtgacct gtggcaaagc   1440
cgacaataac atgcagggca acaaaatgta tgttcaccca gagtctccta atactggttc   1500
ccactggatg agacaggaga tttcattcgg gaaattaaaa ctcaccaata acaaaggcgc   1560
aaataacaac aacacccaga tgatagtctt acaatcctta cacaaatacc aaccccgact   1620
gcatattgtt gaagttacag aggatggcgt ggaggacttg aatgagccct caaagaccca   1680
gacttttacc ttctcagaaa cgcaattcat tgcagtgact gcctaccaaa acaccgatat   1740
tactcaacta aagattgatc ataacccctt tgcaaaaggc ttcagagaca actatgattc   1800
catgtacacc gcttcagaaa atgacaggtt aactccatct cccacggatt ctcctagatc   1860
ccatcagatt gtccctggag gtcggtacgg cgttcaatcc ttcttcccgg agccctttgt   1920
caacacttta cctcaagccc gctattataa tggcgagaga accgtgccac agaccaacgg   1980
cctcctttca ccccaacaga gcgaagaggt ggccaaccct ccccagcggt ggcttgtcac   2040
gcctgtccag caacctggga ccaacaaact agacatcagt tcctatgaat ctgaatatac   2100
ttctagcaca ttgctcccat atggcattaa atccttgccc cttcagacat cccatgccct   2160
ggggtattac ccagacccaa cctttcctgc aatggcaggg tggggaggtc gaggttctta   2220
ccagaggaag atggcagctg gactaccatg gacctccaga acaagcccca ctgtgttctc   2280
tgaagatcag ctctccaagg agaaagtgaa agaggaaatt ggctcttctt ggatagagac   2340
accccccttcc atcaaatctc tagattccaa tgattcagga gtatacacca gtgcttgtaa   2400
gcgaaggcgg ctgtctccta gcaactccag taatgaaaat tcaccctcca taaagtgtga   2460
ggacattaat gctgaagagt atagtaaaga cacctcaaaa ggcatgggag ggtattatgc   2520
tttttacaca actccctaaa gagttatttt aacctcaaaa attagctaac tttttgcaga   2580
tggacttggt ggtgtttttt gttgtcttct ttgcctaggt tgccaaaaag atgtttgcct   2640
tccaccttga tgcatcctgt tttgtgcaat tctctaaaag aaggtgccaa agctttttga   2700
ttgctgcagg taactgaaac aaacctagca tttttaaaaa ataagattaa tggaagactt   2760
taaggtattt taaaattcga agggtatcca aggttctgta tttatttatt ggggagacac   2820
taacccttca aagaagcagg ctgtgaacat tgggtgccca gtgctatcag atgagttaaa   2880
acctttgatt ctcatttcta tttgtaaatt cttaagcaaa tagaagccga gtgttaaggt   2940
gttttgcttc tgaaagaggg ctgtgccttc cgtttcagaa ggagacattt tgctgttaca   3000
ttctgccagg ggcaaaagat actaggccca ggagtcaaga aaagcttttg tgaaagtgat   3060
agtttcacct gactttgatt ccttaacccc cggcttttgg aacaagccat gtttgcccta   3120
gtccaggatt gcctcacttg agacttgcta ggcctctgct gtgtgctggg gtggccagtg   3180
ggactcagga gagagcaagc taaggagtca ccaaaaaaaa aaaaaaaaaa aagggagaat   3240
```

-continued

```
ttaaaagtgt acagttgtgt gtttagatac actatagaat aatgtggtat atattgtaca   3300

aatagtctac ataggtgtct gggataatgt aaaactggtg ctttggcttt gtaaagaatt   3360

tgcaaatcac ttaacagctg caggggcaag gggagagttt catcatcccc atgatatttg   3420

ggaatattct gtttacttct tagatagtta agaatgtatt cagctactat gtactaactt   3480

gaaccgtgtt taaggaaaac tcctatttca tcctcttctt gcgccatccc ctctccctaa   3540

cttggtaatg tgaagaaact aaaacctgat accacagctc ctataggcat tttagagatc   3600

ttggattttt atgtacagtc ttagtcattt ttaataaatg tggttcagta agggaacgga   3660

aaaaaaaaaa aaaa                                                     3674
```

<210> SEQ ID NO 32
<211> LENGTH: 984
<212> TYPE: DNA
<213> ORGANISM: Homo sapiens

<400> SEQUENCE: 32

```
ggggaacatg aagtcactga gcctgctcca cctctttcct ctcccaagag ctaaaagaga     60

gcaaggagga aacaacagca gctccaacca gggcagcctt cctgagaaga tgcaaccaat    120

cctgcttctg ctggccttcc tcctgctgcc cagggcagat gcaggggaga tcatcggggg    180

acatgaggcc aagccccact cccgccccta catggcttat cttatgatct gggatcagaa    240

gtctctgaag aggtgcggtg gcttcctgat acgagacgac ttcgtgctga cagctgctca    300

ctgttgggga agctccataa atgtcacctt gggggcccac aatatcaaag aacaggagcc    360

gacccagcag tttatccctg tgaaaagacc catcccccat ccagcctata atcctaagaa    420

cttctccaac gacatcatgc tactgcagct ggagagaaag gccaagcgga ccagagctgt    480

gcagcccctc aggctaccta gcaacaaggc ccaggtgaag ccagggcaga catgcagtgt    540

ggccggctgg gggcagacgg ccccccctggg aaaacactca cacacactac aagaggtgaa    600

gatgacagtg caggaagatc gaaagtgcga atctgactta cgccattatt acgacagtac    660

cattgagttg tgcgtggggg acccagagat taaaaagact tcctttaagg gggactctgg    720

aggccctctt gtgtgtaaca aggtggccca gggcattgtc tcctatggac gaaacaatgg    780

catgcctcca cgagcctgca ccaaagtctc aagctttgta cactggataa agaaaaccat    840

gaaacgctac taactacagg aagcaaacta agcccccgct gtaatgaaac accttctctg    900

gagccaagtc cagatttaca ctgggagagg tgccagcaac tgaataaata cctcttagct    960

gagtggaaaa aaaaaaaaaa aaaa                                           984
```

<210> SEQ ID NO 33
<211> LENGTH: 1229
<212> TYPE: DNA
<213> ORGANISM: Homo sapiens

<400> SEQUENCE: 33

```
ttcctttctc tctcagctct ccgtctctct ttctctctca gcctctttct ttctccctgt     60

ctcccccact gtcagcacct cttctgtgtg gtgagtggac cgcttacccc actaggtgaa    120

gatgtcagcc caggagagct gcctcagcct catcaagtcc tcggcagcct gatcttctgc    180

ttcggcatct ggatcctcat tgacaagacc agcttcgtgt cctttgtggg cttggccttc    240

gtgcctctgc agatctggtc caaagtcctg gccatctcag gaatcttcac catgggcatc    300

gccctcctgg gttgtgtggg ggccctcaag gagctccgct gcctcctggg cctgtatttt    360

gggatgctgc tgctcctgtt tgccacacag atcaccctgg gaatcctcat ctccactcag    420
```

-continued

```
cgggcccagc tggagcgaag cttgcgggac gtcgtagaga aaaccatcca aaagtacggc    480

accaaccccg aggagaccgc ggccgaggag agctgggact atgtgcagtt ccagctgcgc    540

tgctgcggct ggcactaccc gcaggactgg ttccaagtcc tcatcctgag aggtaacggg    600

tcggaggcgc accgcgtgcc ctgctcctgc tacaacttgt cggcgaccaa cgactccaca    660

atcctagata aggtgatctt gccccagctc agcaggcttg gacacctggc gcggtccaga    720

cacagtgcag acatctgcgc tgtccctgca gagagccaca tctaccgcga gggctgcgcg    780

cagggcctcc agaagtggct gcacaacaac cttatttcca tagtgggcat ttgcctgggc    840

gtcggcctac tcgagctcgg gttcatgacg ctctcgatat tcctgtgcag aaacctggac    900

cacgtctaca accggctcgc tcgataccgt taggccccgc cctccccaaa gtcccgcccc    960

gcccccgtca cgtgcgctgg gcacttccct gctgcctgta aatatttgtt taatccccag   1020

ttcgcctgga gccctccgcc ttcacattcc cctggggacc cacgtggctg cgtgcccctg   1080

ctgctgtcac ctctcccacg ggacctgggg ctttcgtcca cagcttcctg tccccatctg   1140

tcggcctacc accacccaca agattatttt tcacccaaac ctcaaataaa tcccctgcgt   1200

ttttggtaaa aaaaaaaaaa aaaaaaaaa                                     1229
```

<210> SEQ ID NO 34
<211> LENGTH: 3451
<212> TYPE: DNA
<213> ORGANISM: Homo sapiens

<400> SEQUENCE: 34

```
cttcagatag attatatctg gagtgaagaa tcctgccacc tatgtatctg gcatagtctc     60

atctggccag aagagctgag acatccgttc ccctacaaga aactctcccc gggtggaaca    120

agatggatta tcaagtgtca agtccaatct atgacatcaa ttattataca tcggagccct    180

gccaaaaaat caatgtgaag caaatcgcag cccgcctcct gcctccgctc tactcactgg    240

tgttcatctt tggttttgtg ggcaacatgc tggtcatcct catcctgata aactgcaaaa    300

ggctgaagag catgactgac atctacctgc tcaacctggc catctctgac ctgtttttcc    360

ttcttactgt ccccttctgg gctcactatg ctgccgccca gtgggacttt ggaaatacaa    420

tgtgtcaact cttgacaggg ctctatttta taggcttctt ctctggaatc ttcttcatca    480

tcctcctgac aatcgatagg tacctggctg tcgtccatgc tgtgtttgct ttaaaagcca    540

ggacggtcac ctttggggtg gtgacaagtg tgatcacttg ggtggtggct gtgtttgcgt    600

ctctcccagg aatcatcttt accagatctc aaaaagaagg tcttcattac acctgcagct    660

ctcattttcc atacagtcag tatcaattct ggaagaattt ccagacatta aagatagtca    720

tcttggggct ggtcctgccg ctgcttgtca tggtcatctg ctactcggga atcctaaaaa    780

ctctgcttcg gtgtcgaaat gagaagaaga ggcacagggc tgtgaggctt atcttcacca    840

tcatgattgt ttattttctc ttctgggctc cctacaacat tgtccttctc ctgaacacct    900

tccaggaatt ctttggcctg aataattgca gtagctctaa caggttggac caagctatgc    960

aggtgacaga gactcttggg atgacgcact gctgcatcaa ccccatcatc tatgcctttg   1020

tcggggagaa gttcagaaac tacctcttag tcttcttcca aaagcacatt gccaaacgct   1080

tctgcaaatg ctgttctatt ttccagcaag aggctcccga gcgagcaagc tcagtttaca   1140

cccgatccac tggggagcag gaaatatctg tgggcttgtg acacggactc aagtgggctg   1200

gtgacccagt cagagttgtg cacatggctt agttttcata cacagcctgg gctgggggtg   1260
```

gggtgggaga ggtctttttt aaaaggaagt tactgttata gagggtctaa gattcatcca 1320
tttatttggc atctgtttaa agtagattag atcttttaag cccatcaatt atagaaagcc 1380
aaatcaaaat atgttgatga aaaatagcaa ccttttttatc tcccctcac atgcatcaag 1440 ttattgacaa actctccctt cactccgaaa gttccttatg tatatttaaa agaaagcctc 1500
agagaattgc tgattcttga gtttagtgat ctgaacagaa ataccaaaat tatttcagaa 1560
atgtacaact ttttacctag tacaaggcaa catataggtt gtaaatgtgt ttaaaacagg 1620
tctttgtctt gctatgggga gaaaagacat gaatatgatt agtaaagaaa tgacactttt 1680
catgtgtgat ttcccctcca aggtatggtt aataagtttc actgacttag aaccaggcga 1740
gagacttgtg gcctgggaga gctggggaag cttcttaaat gagaaggaat ttgagttgga 1800
tcatctattg ctggcaaaga cagaagcctc actgcaagca ctgcatgggc aagcttggct 1860
gtagaaggag acagagctgg ttgggaagac atggggagga aggacaaggc tagatcatga 1920
agaaccttga cggcattgct ccgtctaagt catgagctga gcagggagat cctggttggt 1980
gttgcagaag gtttactctg tggccaaagg agggtcagga aggatgagca tttagggcaa 2040
ggagaccacc aacagccctc aggtcagggt gaggatggcc tctgctaagc tcaaggcgtg 2100
aggatgggaa ggagggaggt attcgtaagg atgggaagga gggaggtatt cgtgcagcat 2160
atgaggatgc agagtcagca gaactggggt ggatttgggt tggaagtgag ggtcagagag 2220
gagtcagaga gaatccctag tcttcaagca gattggagaa acccttgaaa agacatcaag 2280
cacagaagga ggaggaggag gtttaggtca agaagaagat ggattggtgt aaaaggatgg 2340
gtctggtttg cagagcttga acacagtctc acccagactc caggctgtct ttcactgaat 2400
gcttctgact tcatagattt ccttcccatc ccagctgaaa tactgagggg tctccaggag 2460
gagactagat ttatgaatac acgaggtatg aggtctagga acatacttca gctcacacat 2520
gagatctagg tgaggattga ttacctagta gtcatttcat gggttgttgg gaggattcta 2580
tgaggcaacc acaggcagca tttagcacat actacacatt caataagcat caaactctta 2640
gttactcatt cagggatagc actgagcaaa gcattgagca aaggggtccc atagaggtga 2700
gggaagcctg aaaaactaag atgctgcctg cccagtgcac acaagtgtag gtatcatttt 2760
ctgcatttaa ccgtcaatag gcaaaggggg gaagggacat attcatttgg aaataagctg 2820
ccttgagcct taaaacccac aaaagtacaa tttaccagcc tccgtatttc agactgaatg 2880
ggggtggggg gggcgcctta ggtacttatt ccagatgcct tctccagaca aaccagaagc 2940
aacagaaaaa atcgtctctc cctcccttg aaatgaatat accccttagt gtttgggtat 3000
attcatttca aagggagaga gagaggtttt tttctgttct gtctcatatg attgtgcaca 3060
tacttgagac tgttttgaat ttgggggatg gctaaaacca tcatagtaca ggtaaggtga 3120
gggaatagta agtggtgaga actactcagg gaatgaaggt gtcagaataa taagaggtgc 3180
tactgacttt ctcagcctct gaatatgaac ggtgagcatt gtggctgtca gcaggaagca 3240
acgaagggaa atgtctttcc ttttgctctt aagttgtgga gagtgcaaca gtagcatagg 3300
accctaccct ctgggccaag tcaaagacat tctgacatct tagtatttgc atattcttat 3360
gtatgtgaaa gttacaaatt gcttgaaaga aaatatgcat ctaataaaaa acaccttcta 3420
aaataaaaaa aaaaaaaaaa aaaaaaaaaa a 3451

<210> SEQ ID NO 35
<211> LENGTH: 1676
<212> TYPE: DNA
<213> ORGANISM: Homo sapiens

<400> SEQUENCE: 35

```
agactcaaca agagctccag caaagacttt cactgtagct tgacttgacc tgagattaac     60
tagggaatct tgagaataaa gatgagctct gaaaattgtt tcgtagcaga gaacagctct    120
ttgcatccgg agagtggaca agaaaatgat gccaccagtc cccatttctc aacacgtcat    180
gaagggtcct tccaagttcc tgtcctgtgt gctgtaatga atgtggtctt catcaccatt    240
ttaatcatag ctctcattgc cttatcagtg ggccaataca attgtccagg ccaatacaca    300
ttctcaatgc catcagacag ccatgtttct tcatgctctg aggactgggt tggctaccag    360
aggaaatgct actttatttc tactgtgaag aggagctgga cttcagccca aaatgcttgt    420
tctgaacatg gtgctactct tgctgtcatt gattctgaaa aggacatgaa ctttctaaaa    480
cgatacgcag gtagagagga acactgggtt ggactgaaaa aggaacctgg tcacccatgg    540
aagtggtcaa atggcaaaga atttaacaac tggttcaacg ttacagggtc tgacaagtgt    600
gtttttctga aaaacacaga ggtcagcagc atggaatgtg agaagaattt atactggata    660
tgtaacaaac cttacaaata ataaggaaac atgttcactt attgactatt atagaatgga    720
actcaaggaa atctgtgtca gtggatgctg ctctgtggtc cgaagtcttc catagagact    780
ttgtgaaaaa aaattttata gtgtcttggg aatttttcttc caaacagaac tatggaaaaa   840
aaggaagaaa ttccaggaaa atctgcactg tgggctttta ttgccatgag ctagaagcat    900
cacaggttga ccaataacca tgcccaagaa tgagaagaat gactatgcaa cctttggatg    960
cactttatat tattttgaat ccagaaataa tgaaataact aggcgtggac ttactattta   1020
ttgctgaatg actaccaaca gtgagagccc ttcatgcatt tgcactattg gaaggagtta   1080
gatgttggta ctagatactg aatgtaaaca aaggaattat ggctggtaac ataggttttt   1140
agtctaattg aatcccttaa actcagggag catttataaa tggacaaatg cttatgaaac   1200
taagatttgt aatatttctc tctttttaga gaaatttgcc aatttacttt gttatttttc   1260
cccaaaaaga atgggatgat catgtattta tttttttact tcctcagctg tagacaggtc   1320
cttttcgatg gtacatattt ctttgccttt ataatctttt atacagtgtc ttacagagaa   1380
aagacataag caaagactat gaggaatatt tgcaagacat agaatagtgt tggaaaatgt   1440
gcaatatgtg atgtggcaaa tctctattag gaaatattct gtaatcttca gacctagaat   1500
aatactagtc ttataatagg tttgtgactt tcctaaatca attctattac gtgcaatact   1560
tcaatacttc atttaaaata tttttatgtg caataaaatg tatttgtttg tattttgtgt   1620
tcagtacaat tataagctgt ttttatatat gtgaaataaa agtagaataa acacaa       1676
```

<210> SEQ ID NO 36
<211> LENGTH: 20
<212> TYPE: DNA
<213> ORGANISM: Artificial Sequence
<220> FEATURE:
<223> OTHER INFORMATION: CCL5-Forward primer

<400> SEQUENCE: 36

```
acacacttgg cggttctttc                                                 20
```

<210> SEQ ID NO 37
<211> LENGTH: 20
<212> TYPE: DNA
<213> ORGANISM: Artificial Sequence
<220> FEATURE:
<223> OTHER INFORMATION: CCL5-Reverse primer

<400> SEQUENCE: 37
cctgctgctt tgcctacatt 20

<210> SEQ ID NO 38
<211> LENGTH: 20
<212> TYPE: DNA
<213> ORGANISM: Artificial Sequence
<220> FEATURE:
<223> OTHER INFORMATION: CXCL16-Forward primer

<400> SEQUENCE: 38
ctacacgagg ttccagctcc 20

<210> SEQ ID NO 39
<211> LENGTH: 20
<212> TYPE: DNA
<213> ORGANISM: Artificial Sequence
<220> FEATURE:
<223> OTHER INFORMATION: CXCL16-Reverse primer

<400> SEQUENCE: 39
caatccccga gtaagcatgt 20

<210> SEQ ID NO 40
<211> LENGTH: 20
<212> TYPE: DNA
<213> ORGANISM: Artificial Sequence
<220> FEATURE:
<223> OTHER INFORMATION: GAPDH-Forward primer

<400> SEQUENCE: 40
accacagtcc atgccatcac 20

<210> SEQ ID NO 41
<211> LENGTH: 20
<212> TYPE: DNA
<213> ORGANISM: Artificial Sequence
<220> FEATURE:
<223> OTHER INFORMATION: GAPDH-Reverse primer

<400> SEQUENCE: 41
tccaccaccc tgttgctgta 20

<210> SEQ ID NO 42
<211> LENGTH: 3134
<212> TYPE: DNA
<213> ORGANISM: Homo sapiens

<400> SEQUENCE: 42
gtttggggcc ggcccaggcc tagggtgtgg aggagccttg ccatcgggct tcctgtctct 60
cttcatttaa gcacgactct gcagaaggaa caaagcaccc tccccactgg gctcctggtt 120
gcagagctcc aagtcctcac acagatacgc ctgtttgaga agcagcgggc aagaaagacg 180
caagcccaga ggccctgcca tttctgtggg ctcaggtccc tactggctca ggcccctgcc 240
tccctcggca aggccacaat gaaccgggga gtccctttta ggcacttgct tctggtgctg 300
caactggcgc tcctcccagc agccactcag ggaaagaaag tggtgctggg caaaaaaggg 360
gatacagtgg aactgacctg tacagcttcc cagaagaaga gcatacaatt ccactggaaa 420
aactccaacc agataaagat tctgggaaat cagggctcct tcttaactaa aggtccatcc 480
aagctgaatg atcgcgctga ctcaagaaga agcctttggg accaaggaaa ctttcccctg 540
atcatcaaga atcttaagat agaagactca gatacttaca tctgtgaagt ggaggaccag 600

```
aaggaggagg tgcaattgct agtgttcgga ttgactgcca actctgacac ccacctgctt    660
caggggcaga gcctgaccct gaccttggag agcccccctg gtagtagccc ctcagtgcaa    720
tgtaggagtc caaggggtaa aaacatacag ggggggaaga ccctctccgt gtctcagctg    780
gagctccagg atagtggcac ctggacatgc actgtcttgc agaaccagaa gaaggtggag    840
ttcaaaatag acatcgtggt gctagctttc cagaaggcct ccagcatagt ctataagaaa    900
gagggggaac aggtggagtt ctccttccca ctcgccttta cagttgaaaa gctgacgggc    960
agtggcgagc tgtggtggca ggcggagagg gcttcctcct ccaagtcttg gatcaccttt   1020
gacctgaaga acaaggaagt gtctgtaaaa cgggttaccc aggaccctaa gctccagatg   1080
ggcaagaagc tcccgctcca cctcaccctg ccccaggcct tgcctcagta tgctggctct   1140
ggaaacctca ccctggccct tgaagcgaaa acaggaaagt tgcatcagga agtgaacctg   1200
gtggtgatga gagccactca gctccagaaa aatttgacct gtgaggtgtg gggacccacc   1260
tcccctaagc tgatgctgag tttgaaactg gagaacaagg aggcaaaggt ctcgaagcgg   1320
gagaaggcgg tgtgggtgct gaaccctgag gcggggatgt ggcagtgtct gctgagtgac   1380
tcgggacagg tcctgctgga atccaacatc aaggttctgc ccacatggtc caccccggtg   1440
cagccaatgg ccctgattgt gctgggggc gtcgccggcc tcctgctttt cattgggcta   1500
ggcatcttct tctgtgtcag gtgccggcac cgaaggcgcc aagcagagcg gatgtctcag   1560
atcaagagac tcctcagtga gaagaagacc tgccagtgtc ctcaccggtt tcagaagaca   1620
tgtagcccca tttgaggcac gaggccaggc agatcccact tgcagcctcc ccaggtgtct   1680
gccccgcgtt tcctgcctgc ggaccagatg aatgtagcag atcccaggcc tctggcctcc   1740
tgttcgcctc ctctacaatt tgccattgtt tctcctgggt taggccccgg cttcactggt   1800
tgagtgttgc tctctagttt ccagaggctt aatcacaccg tcctccacgc catttccttt   1860
tccttcaagc ctagcccttc tctcattatt tctctctgac cctctcccca ctgctcattt   1920
ggatcccagg ggagtgttca gggccagccc tggctggcat ggagggtgag gctgggtgtc   1980
tggaagcatg gagcatggga ctgttctttt acaagacagg accctgggac cacagagggc   2040
aggaacttgc acaaaatcac acagccaagc cagtcaagga tggatgcaga tccagaggtt   2100
tctggcagcc agtacctcct gccccatgct gcccgcttct caccctatgt gggtgggacc   2160
acagactcac atcctgacct tgcacaaaca gcccctctgg acacagcccc atgtacacgg   2220
cctcaaggga tgtctcacat cctctgtcta tttgagactt agaaaaatcc tacaaggctg   2280
gcagtgacag aactaagatg atcatctcca gtttatagac cagaaccaga gctcagagag   2340
gctagatgat tgattaccaa gtgccggact agcaagtgct ggagtcggga ctaacccagg   2400
tcccttgtcc caagttccac tgctgcctct tgaatgcagg gacaaatgcc acacggctct   2460
caccagtggc tagtggtggg tactcaatgt gtacttttgg gttcacagaa gcacagcacc   2520
catgggaagg gtccatctca gagaatttac gagcagggat gaaggcctcc ctgtctaaaa   2580
tccctccttc atcccccgct ggtggcagaa tctgttacca gaggacaaag cctttggctc   2640
ttctaatcag agcgcaagct gggagcacag gcactgcagg agagaatgcc cagtgaccag   2700
tcactgaccc tgtgcagaac ctcctggaag cgagctttgc tgggagaggg ggtagctagc   2760
ctgagaggga accctctaag ggacctcaaa ggtgattgtg ccaggctctg cgcctgcccc   2820
acaccctccc ttaccctcct ccagaccatt caggacacag ggaaatcagg gttacaaatc   2880
ttcttgatcc acttctctca ggatcccctc tcttcctacc cttcctcacc acttccctca   2940
```

-continued

| | |
|---|---|
| gtcccaactc cttttcccta tttccttctc ctcctgtctt taaagcctgc ctcttccagg | 3000 |
| aagacccccc tattgctgct ggggctcccc atttgcttac tttgcatttg tgcccactct | 3060 |
| ccacccctgc tcccctgagc tgaaataaaa atacaataaa cttactataa agatgcaaaa | 3120 |
| aaaaaaaaaa aaaa | 3134 |

METHOD FOR CLASSIFYING CANCER PATIENTS INTO APPROPRIATE HEPATOCELLULAR CARCINOMA TREATMENT GROUPS AND COMPOUNDS FOR TREATING THE PATIENT

CROSS REFERENCE TO RELATED APPLICATIONS

This application claims the priority to Singapore application No. 10201709924T, filed 30 Nov. 2017, the contents of which are incorporated herein by reference.

SEQUENCE LISTING

A sequence listing under 37 CFR 1.821 as an ASCII text file is submitted herewith, the content of which is incorporated by reference in its entirety. The ASCII text file is entitled "YSA1PN080JGC_Sequence_Listing" with a date of creation of 23 Nov. 2017 and a size of 128,513 bytes.

FIELD OF INVENTION

The present invention relates to systems and methods for classifying cancer patients into treatment groups to prognosticate and to predict response to specific cancer treatments, specifically radiation therapy and in particular selective internal radiation therapy (SIRT) treatment alone or in combination with other therapies including immunotherapy.

BACKGROUND TO THE INVENTION

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

In 2015 cancer caused 15.7% of human deaths. A large portion of these fatalities include cancers that were diagnosed late and were at a stage that they could not be resected and/or had developed a hyper-vascularized mass around the cancer. A hyper-vascularized mass around a cancer receives its blood supply predominantly through newly formed branches of existing arteries such as the hepatic artery in the case of Hepatocellular carcinoma (HCC). A common treatment for hyper-vascularised cancers is to embolize the newly formed branch. Selective internal radiation therapy (SIRT) (also called radioembolization (RE) is one form of therapy whereby radioactive coated microspheres are delivered directly into the hyper-vascularised cancer via transarterial catheter under radiologic guidance.

This precise mode of delivery spares the non-malignant organs as radiation therapy is only delivered through the branches supplying to the tumors and the radiation from the microspheres destroys the tumor cells within a limited area of emission while sparing the healthy tissues.

Hepatocellular carcinoma (HCC) is a highly malignant disease, and the second most common cause of cancer-associated deaths worldwide (Ferlay, et al. Int J Cancer 136, E359-386 (2015).). The most effective therapeutic options for HCC are tumor resection or liver transplantation, but these are limited to early stage disease (Bruix, and Sherman, Hepatology (Baltimore, Md.) 53, 1020-1022 (2011).). The majority of the patients who have locally advanced disease are treated with loco-regional therapies such as transarterial chemoembolization or Yttrium-90 (Y90) radioembolization (RE), also-known-as selective internal radiation therapy (SIRT) (Raza, and Sood, World Journal of Gastroenterology: WJG 20, 4115-4127 (2014).).

The liver is generally sustained as an immunosuppressive microenvironment. The main reason the liver has evolved in this way is that blood from the arterial circulation and the intestines enter the liver, where toxins and gut-derived microbial products are captured and eliminated. To prevent aberrant immunity in response to continual pathogen exposure, the liver has a unique system of immune regulation. Hepatocytes contribute to the liver's inherent tolerogenicity by priming naïve T cells in the absence of co-stimulation, resulting in defective cytotoxicity and clonal deletion. This suggests that immunotherapy particularly intrahepatic T cell priming would not be useful in treating HCC. Further, the liver processes toxins and as such is generally less susceptible to chemotherapeutic agents.

Yttrium-90 (Y90)-radioembolization (RE) significantly regresses locally advanced hepatocellular carcinoma (HCC) and delays disease progression. Despite its effectiveness, the immunological impact of Y90-RE, which elicits a sustained therapeutic response, is not well understood. Y90-RE has been shown to elicit a disease-control by tumor-downstaging and delayed disease progression (Kallini, et al. Advances in Therapy 33, 699-714 (2016).). The half-life of the Y90-isotope is ~64.2 hours, but maximal clinical response, i.e. tumor regression and decrease in serum alfa-feto protein, is only seen 3-to-6-months after treatment (Salem, et al. Gastroenterology 138, 52-64 (2010).). The mechanisms that underlie this delayed, yet long-lasting anti-tumor effect remain elusive.

There is a need to understand who will respond to treatments to ameliorate at least one of the problems mentioned above.

SUMMARY OF THE INVENTION

It is an object of the present invention to provide systems and methods for classifying cancer patients into treatment groups to prognosticate and to predict response to specific cancer treatments, specifically whether radiation therapy will be an appropriate cancer treatment, in particular selective internal radiation therapy (SIRT) treatment alone or in combination with other therapies including immunotherapy.

Accordingly, an aspect of the invention provides an in vitro method for the prognosis of response to treatment for a patient suffering from cancer, the method comprising:

measuring expression of at least one immune marker in a leukocyte sample taken from patient with cancer;

classifying the patient sample into (i) sustained responders (SR) to selective internal radiation therapy (SIRT) or (ii) transient/non-responders (TR/NR) to (SIRT) based on the expression of the at least one immune marker in relation to a predetermined value.

Another aspect of the invention provides a system for prognosticating a response to treatment for a patient suffering from cancer, the system comprising:

a processing unit operable to: obtain a dataset of immune marker expression profiles in a leukocyte sample taken from the patient with cancer; sort the dataset based on a probability that an immune marker expression of a plurality of cells in the leukocyte sample will correspond to patients with cancer that respond to selective internal radiation therapy (SIRT) or not respond to or only transiently respond to SIRT; and allocate a probability score to the sample taken from the patient with cancer that the patient will (i) respond to SIRT or (ii) not respond or only transiently respond to SIRT treatment, wherein the probability score of the sample is obtained from the majority of the plurality of cells having the immune marker expression corresponding to patients with cancer that respond to SIRT or corresponding to patients with cancer that do not respond or transiently respond to SIRT.

Another aspect of the invention provides use of a composition comprising a SIRT and an immunotherapy in the manufacture of a medicament for use in the treatment of cancer in a patient prognosticated as a sustained responders (SR) to selective internal radiation therapy (SIRT), preferably hepatocellular carcinoma.

Another aspect of the invention provides a method of treating a patient with cancer that is prognosticated as a sustained responders (SR) to selective internal radiation therapy (SIRT) comprising administering a therapeutically effective dose of a composition comprising a SIRT and an immunotherapy to the patient.

Another aspect of the invention provides a composition comprising a selective internal radiation therapy (SIRT) and an immunotherapy for use in the treatment of cancer in a patient prognosticated as a sustained responder (SR) to SIRT.

Other aspects of the invention will become apparent to those of ordinary skill in the art upon review of the following description of specific embodiments of the invention in conjunction with the accompanying figures.

BRIEF DESCRIPTION OF THE DRAWINGS

The present invention will now be described, by way of example only, with reference to the following accompanying drawings.

DETAILED DESCRIPTION OF THE INVENTION

Figure 1:
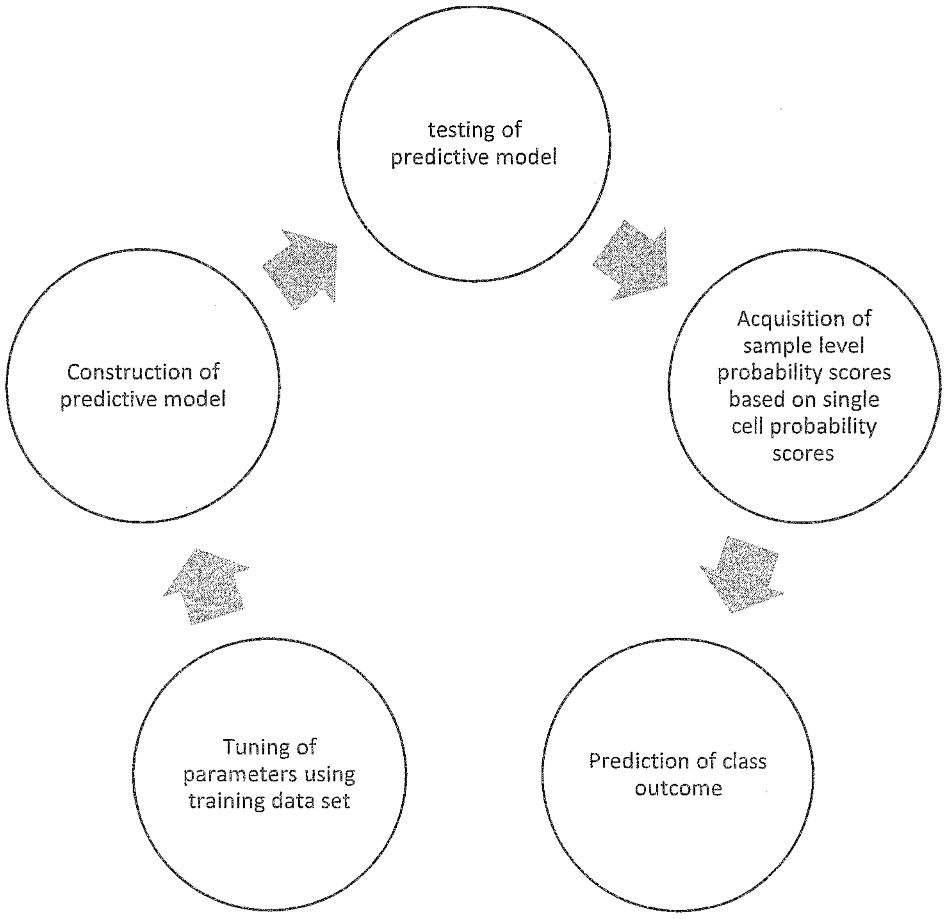
FIG. 1: Flow of model for prediction of sustained response in HCC patients after Y90 radioembolization. Single cell CyTOF data with 37 markers were used to obtain a final prediction class status for each individual patient as a responder or non-responder.

Unless defined otherwise, all technical and scientific terms used herein have the same meaning as is commonly understood by a skilled person to which the subject matter herein belongs. As used herein, the following definitions are supplied in order to facilitate the understanding of the present invention.

Throughout this document, unless otherwise indicated to the contrary, the terms "comprising", "consisting of", "having" and the like, are to be construed as non-exhaustive, or in other words, as meaning "including, but not limited to".

Furthermore, throughout the specification, unless the context requires otherwise, the word "include" or variations such as "includes" or "including" will be understood to imply the inclusion of a stated integer or group of integers but not the exclusion of any other integer or group of integers.

As used in the specification and the appended claims, the singular form "a", and "the" include plural references unless the context clearly dictates otherwise.

The immune profile of surgically resected HCC, which has been downstaged by Y90-RE were analysed. Using time-of-flight mass-cytometry (CyTOF) for high-dimensional, in-depth immunophenotyping key anti-tumour immune responses induced by the Y90-RE have been identified that may underlie the clinical response. Next-generation sequencing (NGS) of tumour tissues from patients after Y90-RE identified activation of multiple immune-subsets and a potential pathway that induces the recruitment of activated CD8+ T cells. The immune profiles of the peripheral-blood-mononuclear-cells (PBMCs) from patients before and at various time points after Y90-RE were also examined and key immune-subsets were identified, including CD8+ T cells and CD4+ T cells expressing the checkpoint receptors PD-1 and Tim-3 and homing receptors CCR5 and CXCR6 in those who responded to Y90-RE. In addition, a prediction model was built using the immune profile of pre-therapy PBMCs to identify potential sustained responders to Y90-RE.

Accordingly, an aspect of the invention provides an in vitro method for the prognosis of response to treatment for a patient suffering from cancer, the method comprising: measuring expression of at least one immune marker in a leukocyte sample taken from patient with cancer; classifying the patient sample into (i) sustained responder (SR) to selective internal radiation therapy (SIRT) or (ii) transient/non-responders (TR/NR) to SIRT based on the expression of the at least one immune marker in relation to a predetermined value.

As used herein the term 'prognoses', 'prognosis', 'prognosed' 'prognosticate', 'prognosticated', or 'prognosing' relates to providing a forecast or prediction of the likely outcome of a cancer after treatment with selective internal radiation therapy (SIRT). SIRT is a form of radiation therapy used in interventional radiology to treat cancer. It is generally for selected patients with surgically unresectable cancers. The treatment involves injecting tiny glass or resin microspheres containing radioactive material preferably yttrium 90 isotope (Y-90) into the arteries that supply the tumour. Because this treatment combines radiotherapy with embolization, it is also called radioembolization. The forecast or prediction of the likely outcome of a cancer after treatment with selective internal radiation therapy (SIRT) may be the predicted outcome of either a sustainable responder (SR) to selective internal radiation therapy (SIRT) or transient/non-responders (TR/NR) to SIRT over a term of 1 month, or 3 months, or 6 months or 12 months or 24 months In various embodiments the forecast or prediction of the likely outcome of a cancer after treatment with selective internal radiation therapy (SIRT) may be based on Response Evaluation Criteria in Solid Tumours (RECIST) 1.1 guidelines (Eisenhauer, et al. Eur J Cancer 45, 228-247 (2009).) wherein sustained responders (SRs) were defined as patients with a likely outcome of no progressive disease (non-PD) by 6 months (180 days) after Y90 RE; while the non-responders (NRs) were defined as patients with a likely outcome of progressive disease (PD) even at 3 months; or transient-responders (TRs) with a likely outcome of a an initial response (non-PD) at 3 months but progressed (PD) by 6 months after Y90 RE.

As used herein a patient suffering from cancer refers to a subject diagnosed with an unresectable cancer, and/or a hyper-vascularized cancer. In various embodiments the cancer may be one of the following unresectable and/or hyper-vascularized cancers: hepatic cell carcinoma (HCC); liver cancer; colorectal cancer; neuroendocrine tumour; HCC patients who are currently ineligible for liver transplant; metastatic liver cancer; metastatic colorectal cancer; metastatic neuroendocrine tumour; a Cancer where a hyper-vascularized mass has developed around the cancer or any other cancer wherein the patient has a life expectancy of at least 3 months.

As used herein the term ‘classifying’, ‘classified’, or ‘classification’, refers to separating a patient population into subpopulations according to specified criteria or a process of determining or arranging patients into a particular group depending on the immune marker profile of a sample taken from the patient or a process or sorting a patient as having a particular prognosis such as a sustainable responder (SR) to selective internal radiation therapy (SIRT) or transient/non-responders (TR/NR) to SIRT. In various embodiments the patient may be classified for different treatment protocols such as treatment with SIRT alone or treatment with SIRT in combination with immunotherapy whereby patients classified as a sustainable responder (SR) to selective internal radiation therapy (SIRT) will be treated with SIRT alone or SIRT in combination with immunotherapy.

In various embodiments the expression of at least one immune marker is measured using mass spectrometry by time of flight (CyTOF) or Next-generation sequencing (NGS), or quantitative polymerase chain reaction (qPCR) or any other method known in the art to measure expression levels of an immune marker. In various embodiments at least one immune marker is selected from PD-1 (SEQ ID NO.9), Tim-3 (SEQ ID NO.21), CXCR6 (SEQ ID NO.12), or combinations thereof, co-expression of PD-1 (SEQ ID NO.9) or Tim-3 (SEQ ID NO.21) with CCR5 (SEQ ID NO.34). In various embodiments the at least one immune marker comprises PD-1 (SEQ ID NO.9). In various embodiments the at least one immune marker comprises Tim-3 (SEQ ID NO.21). In various embodiments the at least one immune marker comprises CXCR6 (SEQ ID NO.12). In various embodiments the at least one immune marker comprises co-expression of PD-1 (SEQ ID NO.9) with CCR5 (SEQ ID NO.34). In various embodiments the at least one immune marker comprises co-expression of Tim-3 (SEQ ID NO.21) with CCR5 (SEQ ID NO.34). In various embodiments the at least one immune marker comprises co-expression of PD-1 (SEQ ID NO.9) with CXCR6 (SEQ ID NO.12). In various embodiments the at least one immune marker comprises co-expression of Tim-3 (SEQ ID NO.21) with CXCR6 (SEQ ID NO.12). In various embodiments the at least one immune marker is any one of PD-1 (SEQ ID NO.9), Tim-3 (SEQ ID NO.21), CCR5 (SEQ ID NO.34) or CXCR6 (SEQ ID NO.12) co-expression on a CD8+ T-cell or a CD4 T-cell.

In various embodiments prior to measuring expression of the at least one immune marker a prediction model is created comprising:

Measuring expression of a plurality of immune markers in a sample taken from a plurality of patients with cancer;

Evaluating a clinical response of the patients with cancer to treatment with (SIRT) at 3 and/or 6 months after treatment wherein the clinical response is selected from (SR), and (TR/NR);

Determining if there is a correlation between each immune marker and either the clinical response (SR), or the clinical response (TR/NR);

determining the probability of each immune marker one by one to positively affect the accuracy of the clinical response;

allocating a probability score to each sample based on the number of immune markers that positively affects the accuracy of the clinical response; and allocating the same probability score for each immune marker present in a leukocyte sample taken from a new patient with cancer to classify the new patient into predicted SR or predicted TR/NR.

In various embodiments the plurality of immune markers are any combination of two or more immune markers listed in table 3, including CD14 (SEQ ID NO.1); CD3 (SEQ ID NO.2); CD19 (SEQ ID NO.3); CD45RO (SEQ ID NO.4); HLA-DR (SEQ ID NO.5); CD8 (SEQ ID NO.6); T-bet (SEQ ID NO.7); CD28 (SEQ ID NO.8); PD-1 (SEQ ID NO.9); CD154 (SEQ ID NO.10); CD103 (SEQ ID NO.11); CXCR6 (SEQ ID NO.12); TNF-α (SEQ ID NO.13), CD25 (SEQ ID NO.14); CD27 (SEQ ID NO.15); CD152 (SEQ ID NO.16); PD-L1 (SEQ ID NO.17); CD244 (SEQ ID NO.18); IL-10 (SEQ ID NO.19); LAG-3 (SEQ ID NO.20); TIM-3 (SEQ ID NO.21); CCR7 (SEQ ID NO.22); CD56 (SEQ ID NO.23); CXCR3 (SEQ ID NO.24); GITR (SEQ ID NO.25); FoxP3 (SEQ ID NO.26); K167 (SEQ ID NO.27); CD80 (SEQ ID NO.28); IFN-γ (SEQ ID NO.29); IL-17A (SEQ ID NO.30); EOMES (SEQ ID NO.31); Granzyme B (SEQ ID NO.32); CD37 (SEQ ID NO.33); CCRS (SEQ ID NO.34); CD4 (SEQ ID NO. 42); or CD69 (SEQ ID NO.35). In various embodiments the plurality of immune markers are any combination of three or more immune markers listed in table 3; or four or more immune markers listed in table 3; or five or more immune markers listed in table 3; or six or more immune markers listed in table 3; or seven or more immune markers listed in table 3; or eight or more immune markers listed in table 3; or nine or more immune markers listed in table 3; or ten or more immune markers listed in table 3; or eleven or more immune markers listed in table 3; or twelve or more immune markers listed in table 3; or thirteen or more immune markers listed in table 3; or fourteen or more immune markers listed in table 3; or fifteen or more immune markers listed in table 3; or sixteen or more immune markers listed in table 3 including CD14; CD3; CD19; CD45RO; HLA-DR; CD8; T-bet; CD28; PD-1; CD4; CD154; CD103; CXCR6; CD25; CD27; CD152; PD-L1; CD244; IL-10, LAG-3; TIM-3; CCR7; CD56; CXCR3; GITR; FoxP3; K167; CD80; IL-17A; EOMES; Granzyme B; CD37; CCRS; or CD69. The expression of a plurality of immune markers in a sample taken from a plurality of patients with cancer are taken before the patients with cancer are treated with SIRS.

In various embodiments the plurality of patients with cancer may include 3 to 1000 patients, 3 to 500 patients; 3 to 200 patients; 3 to 100 patients; 3 to 90 patients; 3 to 80 patients; 3 to 70 patients; 3 to 60 patients; 3 to 50 patients; 3 to 40 patients; 3 to 30 patients; 3 to 20 patients; 3 to 10 patients, or any number of patients more than 2 that is suitable to create a prediction model that is at least as accurate as the classification of the patient samples based on the expression of the at least one immune marker in relation to the predetermined value to predict whether the patient will respond to treatment with (SIRT) mentioned above.

In various embodiments the evaluation of the clinical response of the patients with cancer to treatment with (SIRT) is based on the Response Evaluation Criteria in Solid Tumours (RECIST) 1.1 guidelines (Eisenhauer, et al. Eur J Cancer 45, 228-247 (2009).) wherein sustained responders (SRs) were defined as patients with a likely outcome of no progressive disease (non-PD) by 6 months (180 days) after Y90 RE; while the non-responders (NRs) were defined as patients with a likely outcome of a minimal response of stable disease (SD) even at 3 months or transient-responders (TRs) with a likely outcome of a an initial response at 3 months but progressed by 6 months after Y90 RE.

In various embodiments the determination of a correlation between each immune marker and either the clinical response (SR), or the clinical response (TR/NR); the determination of the probability of each immune marker to positively affect the accuracy of the clinical response and the allocation of a probability score to each sample based on the number of immune markers that positively affects the accuracy of the clinical response is accomplished using a machine leaning algorithm such as a random forest prediction model random forest. Other similar weighted neighbourhood schemes may also be used. In various embodiments the random forest comprises models built from a training set mathematically expressed as:

$$\{x_i,y_i\}^n i=1 \tag{1}$$

Wherein x refers to an immune marker, y refers to a clinical response, i refers to a number of cells and n refers to the number of trees.

This makes predictions ŷ for new points x' by looking at the "neighbourhood" of the point, formalized by a weight function W mathematically expressed as:

$$\hat{y}=\Sigma_{i=1}{}^n W(x_i,x')y_i$$

Here, W ($x_i$, x') is the non-negative weight of the i'th training point relative to the new point x' in the same tree. For any particular x', the weights for points $x_i$, must sum to one. Weight functions are given as follows:

In k-NN, the weights are $$W(x_i, x') = \frac{1}{k}$$

if $x_i$ is one of the k points closest to x', and zero otherwise.

In a tree, $$W(x_i, x') = \frac{1}{k'},$$

if $x_i$ is one of the k' points in the same leaf as x', and zero otherwise.

Since a forest averages the predictions of a set of m trees with individual weight functions $W_j$, its predictions are $$\hat{y} = \frac{1}{m}\sum\nolimits_{j+1}^{m} \sum\nolimits_{i=1}^{n} W_j(x_i, x')y_i = \sum\nolimits_{i+1}^{n}\left(\frac{1}{m}\sum\nolimits_{j+1}^{m} W_j(x_i, x')y_i\right.$$

This shows that the whole forest is again a weighted neighbourhood scheme, with weights that average those of the individual trees. The neighbours of x' in this interpretation are the points $X_i$ sharing the same leaf in any tree j. In this way, the neighbourhood of x' depends in a complex way on the structure of the trees, and thus on the structure of the training set. The shape of the neighbourhood used by a random forest adapts to the local importance of each feature wherein m refers to the number of random variables. In various embodiments n is 10 and m is 2000.

In various embodiments the determination of the probability of each immune marker to positively affect the accuracy of the clinical response is at a cellular level that determines the probability that an immune marker expressed in relation to an individual cell will have a sustained response to SIRT or not. In various embodiments single-cell expression data of about 10,000 single cells with a plurality of immune markers from each patient from randomly selected cancer patients may be used. In various embodiments single-cell expression data is downsampled to about 10,000 single cells to improve the accuracy of the single cell level.

Figure 2:
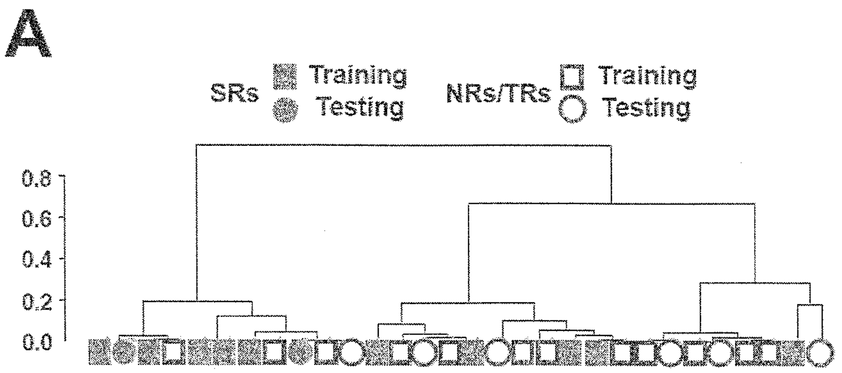
FIG. 2: Prediction model for sustained response to Y90-RE using random forest prediction method. A. Dendrogram showing distance between samples in the training cohort n=22 and testing cohort n=8 based on the random forest prediction model. B. Accuracy curve based on mtry (number of random variables) and ntree (number of trees) for the training model using random forest prediction method. The most accurate parameters selected was mtry=10 and ntree=2000 with an accuracy of 76.8% C. A depiction of how the clinical outcomes are predicted D. Receiver operating characteristic (ROC) curve from Random Forests prediction method to predict sustained response after Y90-RE in the training cohort n=22 and validation/testing cohort n=8. AUC=area under the curve.
Figure 2:
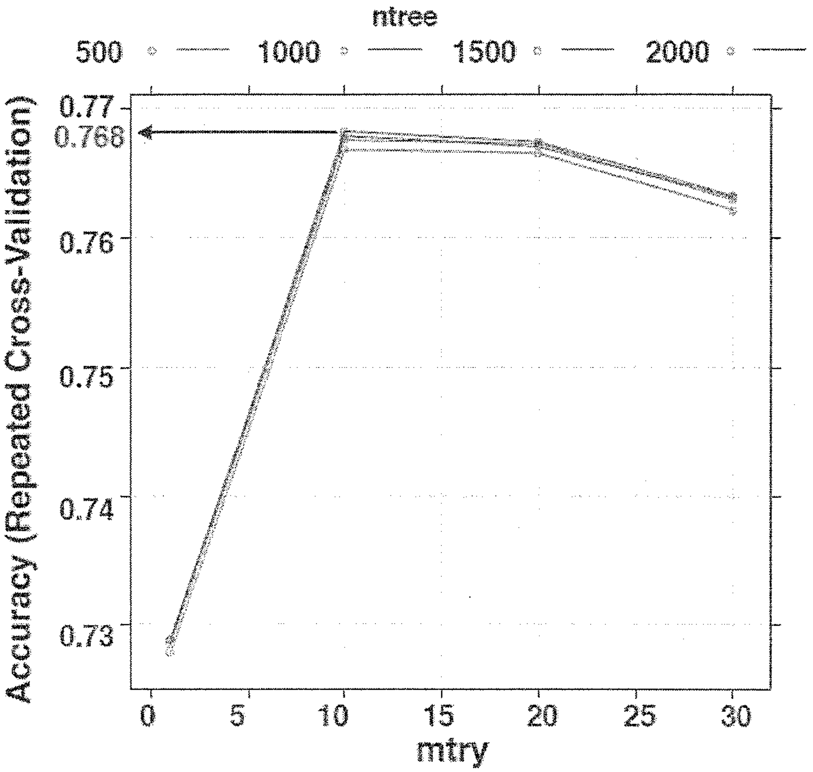
Figure 2:
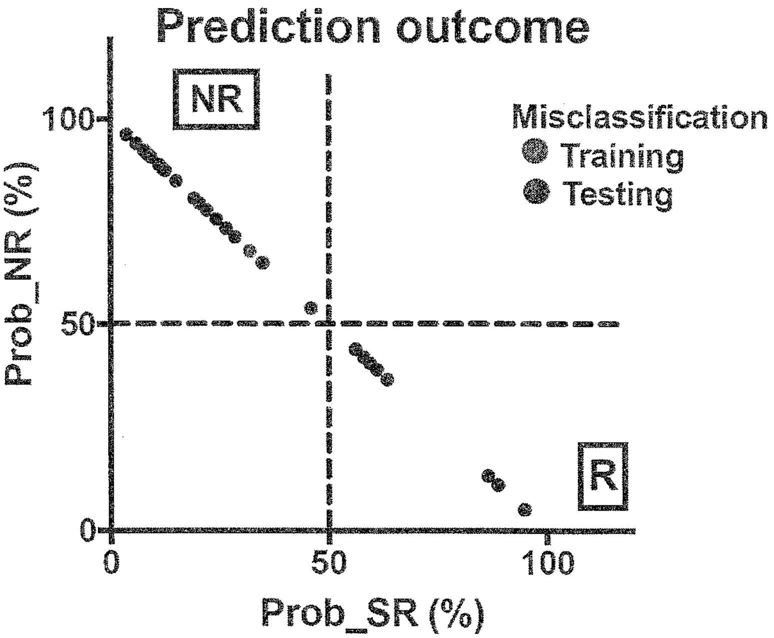
Figure 2:
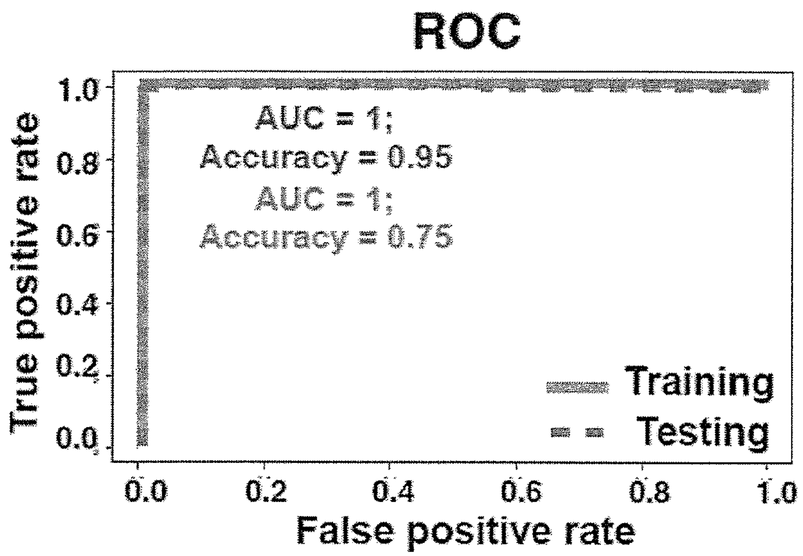

In various embodiments the allocation of a probability score to each sample based on the number of immune markers that positively affects the accuracy of the clinical response is at a sample level that compares the neighbouring cell expression profiles in each sample and allocates the probability score to each sample based on the number of immune markers that positively affects the accuracy of the clinical response. In various embodiments for each of the samples, a percentage of cells being classified as SR or NR is computed and used as a voting system for probability scores, where ≥50% as SR classifies the samples in SR group while <50% as SR classifies them in NR group (FIG. 2C). This final step of voting system generates highly accurate prediction outcomes. The single cell training model and sample based voting system, provides highly accurate prediction of response to SIRT Y90 RE than any other clinical parameters.

In various embodiments the new patient or new patients then become a test set. The new patient may be one or more new patients or any number of new patients. In various embodiments the new patient has not been treated with SIRT when the sample is taken.

In various embodiments the method further comprises comparing the predicted SR or predicted TR/NR with the classification of the patient samples based on the expression of the at least one immune marker in relation to the predetermined value to predict whether the patient will respond to treatment with (SIRT).

The comparison of the testing set of new patients and the classification of the patient samples based on the expression of the at least one immune marker in relation to the predetermined value to predict whether the patient will respond to treatment with (SIRT) allows for checking the accuracy of the prediction to ensure the new patient receives the most appropriate treatment, whereby patients predicted to be a sustainable responder (SR) to selective internal radiation therapy (SIRT) will be treated with SIRT alone or with SIRT in combination with immunotherapy. Similarly, patients predicted to be transient/non responders (TR/NR) will not be treated with SIRT and would instead be treated with TACE, Sorafenib or immunotherapy alone.

In various embodiments the immune marker allocated with a higher probability to positively affect the accuracy of the clinical response comprises the at least one immune marker.

In various embodiments at least one immune marker is selected from PD-1, Tim-3, CXCR6, or combinations thereof, co-expression of PD-1 or Tim-3 with CCR5. In various embodiments the at least one immune marker comprises PD-1. In various embodiments the at least one immune marker comprises Tim-3. In various embodiments the at least one immune marker comprises CXCR6. In various embodiments the at least one immune marker comprises co-expression of PD-1 with CCR5. In various embodiments the at least one immune marker comprises co-expression of Tim-3 with CCR5. In various embodiments the at least one immune marker comprises co-expression of PD-1 with CXCR6. In various embodiments the at least one immune marker comprises co-expression of Tim-3 with CXCR6. In various embodiments the at least one immune marker is any one of PD-1, Tim-3, CCR5 or CXCR6 co-expression on a CD8+ T-cell.

In various embodiments the leukocyte sample comprises a tumour infiltrating leukocyte sample. In various other embodiments the leukocyte sample comprises a peripheral blood mononuclear cell (PBMC) sample. In various embodiments the leukocyte sample comprises a T-cell expressing CD 8. In various embodiments the leukocyte sample comprises a T-cell expressing CD 4. In various embodiments the sample is analysed using mass spectrometry by time of flight (CyTOF)

In various embodiments the cancer is hepatocellular carcinoma.

In various embodiments the leukocyte sample taken from patient with cancer, including a test patient with cancer predicted or classified as sustainable responder (SR) is identified as requiring treatment with SIRT alone or a combination of SIRT and an immunotherapy.

SIRT and Immunotherapy like other therapies have side effects and add to the cost of any treatment. Therefore the advantage of first predicting if a patient with cancer will respond to SIRT is that only patients with cancer that will have a susatained response to the SIRT treatment will be given SIRT alone or SIRT with the additional immunotherapy. Similarly, patients predicted to be transient/non responders (TR/NR) will not be treated with SIRT and would instead be treated with TACE, Sorafenib or immunotherapy alone.

As used herein the term 'immunotherapy' may refer to active, passive or a hybrid of active and passive immunotherapy. Active immunotherapy directs the immune system to attack tumour cells and may involve the removal of immune cells from the blood or from a tumor. Those specific for the tumor are cultured and returned to the patient where they attack the tumor; alternatively, immune cells can be genetically engineered to express a tumor-specific receptor, cultured and returned to the patient. In various embodiments this may include Adoptive T-cell therapy. Passive immunotherapies enhance existing anti-tumor responses and include the use of monoclonal antibodies, lymphocytes or cytokines. In various embodiments the immunotherapy may comprise antibodies that inhibit tyrosine kinase; programmed cell death 1 receptor (PD-1); Hepatitis A virus cellular receptor 2 (HAVCR2), also known as T-cell immunoglobulin and mucin-domain containing-3 (Tim-3); vascular endothelial growth factor; (VEGF); epidermal growth factor receptor (EGFR); cytotoxic T-lymphocyte-associated protein 4 (CTLA-4) or Lymphocyte-activation gene 3 (Lag-3). Suitable antibodies may be selected from sunitinib; erlotinib; ipilimumab; nivolumab; pembrolizamab and bevacizumab. In various embodiments the immunotherapy may comprise cytokines or chemokines for example interferons such as TNFα or interleukins such as IL-2. In various embodiments the immunotherapy may comprise combinations of any of the above listed immunotherapies.

Another aspect of the invention provides a system for prognosing a response to treatment for a patient suffering from cancer, the system comprising:

a processing unit operable to: obtain a dataset of immune marker expression profiles in a leukocyte sample taken from the patient with cancer; sort the dataset based on a probability that an immune marker expression of a plurality of cells in the leukocyte sample will correspond to patients with cancer that respond to selective internal radiation therapy (SIRT) or not respond to or only transiently respond to SIRT; and allocate a probability score to the sample taken from the patient with cancer that the patient will (i) respond to SIRT or (ii) not respond or only transiently respond to SIRT treatment, wherein the probability score of the sample is obtained from the majority of the plurality of cells having the immune marker expression correspond to patients with cancer that respond to SIRT or correspond to patients with cancer that do not respond or transiently respond to SIRT.

The processing unit may be any known processing unit able to obtain, sort and allocate the dataset as described herein.

In various embodiments the system further comprising a device for measuring expression of immune markers in a leukocyte sample taken from the patient with cancer.

In various embodiments the processing unit forms part of the device for measuring expression of immune markers in a leukocyte sample taken from the patient with cancer.

In various embodiments the device is a cytometer. In various embodiments the cytometer is a mass cytometer suitable for combined plasma mass spectrometry and time of flight mass spectrometry. In this approach, antibodies are conjugated with isotopically pure elements, and these antibodies are used to label both ubiquitous and targeted immune markers such as leukocyte proteins. Cells are nebulized and sent through an argon plasma, which ionizes the metal-conjugated antibodies. The metal signals are then analyzed by a time-of-flight mass spectrometer. In various other embodiments the cytometer may be a flow cytometer that uses conjugated fluorophores rather than isotopes or any other cytometer known in the art to defect and/or measure expression of immune markers in a leukocyte.

In various embodiments the device is a next generation sequencer such as pyrosequencers, Hi-Seq genome sequencers (illumina), massively parallel signature sequencer, or any other high-throughput sequencing device or system known in the art to defect and/or measure mRNA expression of immune markers in a leukocyte. In various embodiments the device is a thermocycler. In various embodiments the thermocycler can be used for measuring quantitative Polymerase Chain Reaction (qPCR) or real time qPCR (RT qPCR). In various embodiments the device is any device or system known in the art to defect and/or measure mRNA expression of immune markers in a leukocyte.

Another aspect of the invention provides a composition comprising a selective internal radiation therapy (SIRT) and an immunotherapy for use in the treatment of cancer in a patient prognosticated as a sustained responder (SR) to SIRT.

A SIRT may comprise tiny glass or resin microspheres containing radioactive material. In various embodiments the SIRT is yttrium 90 isotope (Y-90). In various embodiments the immunotherapy may include Adoptive T-cell therapy. In various embodiments the immunotherapy may include T-cells engineered to be directed against tumour antigens. In various embodiments the immunotherapy may comprise antibodies that inhibit tyrosine kinase; programmed cell death 1 receptor (PD-1); Hepatitis A virus cellular receptor 2 (HAVCR2), also known as T-cell immunoglobulin and mucin-domain containing-3 (Tim-3); vascular endothelial growth factor; (VEGF); epidermal growth factor receptor (EGFR); cytotoxic T-lymphocyte-associated protein 4 (CTLA-4) or Lymphocyte-activation gene 3 (Lag-3). Suitable antibodies may be selected from sunitinib; erlotinib; ipilimumab; nivolumab; pembrolizamab and bevacizumab. In various embodiments the immunotherapy may comprise cytokines or chemokines for example interferons such as TNFα or interleukins such as IL-2. In various embodiments the immunotherapy may comprise combinations of any of the above listed immunotherapies.

In various embodiments the immunotherapy may be included on the microspheres together with the yttrium 90 isotope (Y-90). In various other embodiments the immunotherapy may be provided separately from the microspheres with the yttrium 90 isotope (Y-90).

In various embodiments the composition is suitable for use in the treatment of cancer. In various embodiments the cancer is hepatocellular carcinoma.

Another aspect of the invention provides use of a composition comprising a selective internal radiation therapy (SIRT) and an immunotherapy in the manufacture of a medicament for use in the treatment of cancer in a patient prognosticated as a sustained responder (SR) to SIRT, preferably hepatocellular carcinoma. Wherein the composition comprising a SIRT and an immunotherapy is as described above herein.

Another aspect of the invention provides a method of treating a patient with cancer that is prognosed as a sustained responder (SR) to selective internal radiation therapy (SIRT) comprising administering a therapeutically effective dose of a composition comprising a SIRT or a SIRT and an immunotherapy to the patient. Wherein the composition comprising a SIRT and an immunotherapy is as described above herein. Similarly, a method of treating a patient with cancer that is prognosed as a transient/non-responder (TR/NR) to selective internal radiation therapy (SIRT) comprises administering other therapies rather than SIRT such as TACE or Sorafenib or immunotherapy to the patient.

In various embodiments the patient with cancer comprises a patient with hepatocellular carcinoma.

In various embodiments the immunotherapy may be administered together with the SIRT.

In various other embodiments the immunotherapy may be administered separately from the SIRT.

EXAMPLES

Time-of-flight mass cytometry and next-generation sequencing (NGS) were used to analyze the immune landscapes of tumor-infiltrating leukocytes (TILs), tumor tissues and peripheral blood mononuclear cells (PBMCs) at different time-points before and after Y90-RE.

TILs isolated after Y90-RE exhibited markers indicative of local immune activation, including high expression of granzyme B (GB) and infiltration of CD8+ T cells, CD56+ NK cells and CD8+CD56+ NKT cells. NGS confirmed the upregulation of genes involved in innate and adaptive immune activation in Y90-RE-treated tumors. Chemotactic pathways involving CCL5 and CXCL16 correlated with the recruitment of activated GB+CD8+ T cells to the Y90-RE-treated tumors. When comparing PBMCs before and after Y90-RE, an increase in TNFα was observed on both the CD8+ and CD4+ T cells as well as an increase in percentage of antigen presenting cells after Y90-RE, implying a systemic immune activation. A high percentage of PD-1+/Tim-3+CD8+ T cells co-expressing the homing receptors CCR5 and CXCR6 denoted Y90-RE responders. A prediction model was also built to identify sustained responders to Y90-RE based on the immune profiles from pre-treatment PBMCs.

High-dimensional analysis of tumor and systemic immune landscapes identified local and systemic immune activation that may explain the sustained response to Y90-RE. Potential biomarkers associated with a positive clinical response were identified and a prediction model was built to identify sustained responders prior to treatment.

Patients and Sample Processing

Tumour tissues and blood samples were obtained from a total of 41 patients with HCC from the National Cancer Center Singapore and Singapore General Hospital who were treated with or without prior Y90 RE therapy. Among which, n=14 underwent surgical resection for HCC and tumor-Infiltrating leukocytes (TILs) were isolated from the resected HCC tissue of 14 patients (Table 1) by enzymatic digestion.

TABLE 1

Clinical information for resected HCC from Y90 RE versus treatment naive patients, n = 12

| No. | Post Y90 RE | Resection* | No. | Treatment Naive | Viral Status | TNM Stage | Grade | Sex | CyTOF | NGS | qPCR |
|---|---|---|---|---|---|---|---|---|---|---|---|
| 1 | HEP157 | 190 | 8 | HEP174 | Hep B | 1 | II | M | + | + | + |
| 2 | HEP165 | 148 | 9 | HEP261 | Hep C | 2 | II | M | + | | + |
| 3 | HEP210 | 232 | 10 | HEP300 | Hep B | 1 | III | M | + | + | + |
| 4 | HEP242 | 182 | 11 | HEP304 | Hep B | 1 | II | F | + | + | + |
| 5 | HEP279 | 89 | 12 | HEP303 | Hep B | 3a | III | M | + | + | +* |

TABLE 1-continued

Clinical information for resected HCC from Y90 RE versus treatment naive patients, n = 12

| No. | Post Y90 RE | Resection* | No. | Treatment Naive | Viral Status | TNM Stage | Grade | Sex | CyTOF | NGS | qPCR |
|---|---|---|---|---|---|---|---|---|---|---|---|
| 6 | HEP279 | 300 | 13 | HEP200 | NIL | 1 | III | M | + | | +* |
| 7 | HEP286 | 261 | 14 | HEP125 | Hep B | 1 | II | M | + | | |
| | Average | 202 | | | | | | | | | |

FootNote:
n = 7 Post Y90 RE versus n = 7 treatment-naive HCC tumors as controls (Ctl) with matched viral status, TNM Stage, Grade and Sex.
*number of days post Y90 RE when resection was performed
+ indicated the pair of samples taken for either CyTOF, NGS or qPCR experiments.
*Two tumor specimens were collected and analysed from HEP279 and HEP285 Y90 RE-treated tumours.

Peripheral blood mononuclear cells (PBMCs) were isolated from blood taken before (pre) and at various time points (1, 3 and 6 months) after Y90 RE from another cohort of 31 patients (Table 2 included 4 HCC patients who were subsequently resected after Y90 RE and their TILs were also analysed and included in Table 1) using conventional Ficoll (GE Healthcare, UK) isolation methods according to manufacturer's instructions.

TABLE 2

Clinical and samples collection information for HCC patients treated with Y90 RE

| No. | Pre | 1 mo | 3 mo | 6 mo | TIL | 3 m RECIST | 6 m RECIST | Tumor multiplicity | Location of progression | Response status |
|---|---|---|---|---|---|---|---|---|---|---|
| 1 | + | + | | | | PD | PD | Multifocal | Non target (distant) | NR |
| 2 | + | + | | | | PD | PD | 1 | Non target (distant) | NR |
| 3 | + | | + | + | | SD | PD | Multifocal | Target | TR |
| 4 | + | | + | | | PD | PD | Multifocal | Non target (distant) | NR |
| 5 | + | | + | + | | PD | PD | Multifocal | Non target (distant) | NR |
| 6 | + | + | | | | PD | PD | 1 | Non target (distant) | NR |
| 7 | + | + | + | + | | SD | PD | Multifocal | Non target (liver) | TR |
| 8 | + | + | + | | | PD | PD | 1 | Target | NR |
| 9 | + | + | + | | | SD | PD | Multifocal | Non target (distant) | TR |
| 10 | + | | + | | + | SD | PD | Multifocal | Non target (liver) | TR |
| 11 | + | | | | | PD | PD | Multifocal | Target | NR |
| 12 | + | | | | | PD | PD | Multifocal | Non target (distant) | NR |
| 13 | + | + | | | | PD | PD | Multifocal | Non target (distant) | NR |
| 14 | + | + | | | | PD | PD | Multifocal | Non target (distant) | NR |
| 15 | + | + | + | + | | PD | PD | Multifocal | Non target (distant) | NR |
| 16 | + | | | | | PD | PD | Multifocal | Non target (distant) | NR |
| 29 | + | | | + | | SD | PD | 1 | — | TR |
| 17 | + | | + | | | PD | PD | Multifocal | Non target (distant) | NR |
| 18 | + | + | | | | PR | PR | 1 | — | SR |
| 19 | + | | + | + | | PR | PR | 1 | — | SR |
| 20 | + | + | + | | | SD | SD | Multifocal | — | SR |
| 21 | + | + | | + | | SD | SD | 1 | — | SR |
| 22 | + | + | + | + | | PR | PR | 1 | — | SR |
| 23 | + | + | | | | PR | PR | Multifocal | — | SR |
| 24 | | + | | | | SD | SD | 1 | — | SR |
| 25 | + | | + | + | + | PR | PR | Multifocal | — | SR |
| 26 | + | | + | + | + | PR | PR | 1 | — | SR |
| 27 | + | | + | | | SD | SD | 1 | — | SR |

TABLE 2-continued

Clinical and samples collection information for HCC patients treated with Y90 RE

| No. | Pre | 1 mo | 3 mo | 6 mo | TIL | 3 m RECIST | 6 m RECIST | Tumor multiplicity | Location of progression | Response status |
|---|---|---|---|---|---|---|---|---|---|---|
| 28 | + | | + | | + | PR | PR | 1 | — | SR |
| 30 | + | + | + | | | PR | PR | 1 | — | SR |
| 31 | + | + | | | | SD | SD | Multifocal | — | SR |

Footnote:
+ Samples used in CyTOF
1 mo, 37 to 53 days; 3 mo, 75-146 days and 6 mo, 157 to 233 days
RECIST 1.1 criteria:
CR, complete response is characterised by "disappearance of all target lesions", PR, partial response is defined as "30% decrease in the sum of diameters of target lesions," PD, progressive disease is defined as "20% increase in the sum of diameters of target lesions" and SD, stable disease is described as "neither sufficient shrinkage to qualify for PR nor sufficient increase to qualify for PD" (24).
Location of progression: target means progression at lesion treated with Y90; non-target means progression at lesions not treated with Y90 either within the liver (Liver); for lesions outside of liver such as lungs (Distant).
Response status: NR = non-responders, patients who are already PD at 3m; TR = transient-responders, patients who are SD, PR or CR (non-PD) at 3m but PD at 6m; and SR = sustained responders, patients who are non-PD at 6m.

Samples used for various analyses are denoted in Tables 1 and 2.

The Response Evaluation Criteria in Solid Tumors (RECIST) 1.1 guidelines (Eisenhauer, et al. Eur J Cancer 45, 228-247 (2009).) was used to evaluate tumour response. Sustained responders (SRs) were defined as patients without any progressive disease (non-PD) by 6 months (180 days) after Y90 RE; while the non-responders (NRs) never had a minimal response of stable disease (SD) even at 3 months; or transient-responders (TRs) who had an initial response at 3 months but progressed by 6 months after Y90 RE (Table 2). This study was approved by the Singapore Health Services—Central Institutional Review Board and all patients provided informed consent.

Time-of-Flight Mass Cytometry (CyTOF)

TILs and PBMCs were analysed with 37 metal-conjugated antibodies (Table 3) using CyTOF as previously described (Chew et al. Proc Natl Acad Sci USA 114, E5900-E5909 (2017)). Briefly, immune cells were stained with cisplatin viability stain (DVS Sciences, USA) and anti-human CD45 leukocyte marker conjugated with lanthanide metal-89, 115 and 172 respectively—a triple-barcode system as previously described (Lai, et al. Cytometry A 87, 369-374 (2015)). The barcoded immune cells were combined and then stained with antibodies targeting surface markers. Cells were fixed with 1.6% paraformaldehyde and permeabilized in 100% methanol to permit intracellular antibody staining. Finally, a DNA intercalater (DVS Sciences, USA) was added for cellular visualization before analysis on a Helios mass cytometer (Fludigm, USA).

TABLE 3

Antibodies used for CyTOF staining

| Isotopes | Antibodies | Clone | Vendor |
|---|---|---|---|
| 89 | CD45 (Barcode 1) | HI30 | Fluidigm |
| 112/114 | CD14 | TüK4 | Life technologies |
| 115 | CD45 (Barcode 2) | HI30 | Biolegend |
| 139 | CD3 | UCHT1 | Biolegend |
| 141 | CD19 | HIB19 | Biolegend |
| 142 | CD45RO | UCHL1 | Biolegend |
| 143 | HLA-DR | L243 | Biolegend |
| 144 | CD8 | SK1 | Biolegend |
| 145 | T-bet | 4B10 | Biolegend |
| 146 | CD28 | CD28.2 | Biolegend |
| 147 | PD-1 | EH12.2H7 | Biolegend |
| 148 | CD4 | SK3 | Biolegend |
| 149 | CD154 | 24-31 | Biolegend |
| 150 | CD103 | B-Ly7 | Ebioscience |

TABLE 3-continued

Antibodies used for CyTOF staining

| Isotopes | Antibodies | Clone | Vendor |
|---|---|---|---|
| 151 | CXCR6 | K041E5 | Biolegend |
| 152 | TNF-α | Mab11 | Biolegend |
| 153 | CD25 | 2A3 | BD bioscience |
| 154 | CD27 | O323 | Biolegend |
| 155 | CD152 | BN13 | BD bioscience |
| 156 | PD-L1 | 29E.2A3 | Biolegend |
| 157 | CD244 | CL7 | Biolegend |
| 158 | IL-10 | JES3-9D7 | Biolegend |
| 159 | LAG-3 | 17B4 | Abcam |
| 160 | TIM-3 | F38-2E2 | Biolegend |
| 161 | CCR7 | G043H7 | Biolegend |
| 162 | CD56 | NCAM16.2 | BD bioscience |
| 163 | CXCR3 | G025H7 | Biolegend |
| 164 | GITR | 621 | Biolegend |
| 165 | FoxP3 | PCH101 | Ebioscience |
| 166 | Ki67 | 20Raj1 | Ebioscience |
| 167 | CD80 | 2D10 | Biolegend |
| 168 | INF-γ | B27 | Biolegend |
| 169 | IL-17A | BL168 | Biolegend |
| 170 | EOMES | 21Mags8 | Ebioscience |
| 171 | CD45RA | JS-83 | Ebioscience |
| 172 | CD45 (Barcode 3) | HI30 | Biolegend |
| 173 | Granzyme B | CLB-GB11 | Abcam |
| 174 | CD137 | 4B4-1 | Biolegend |
| 175 | CCR5 | T21/8 | Biolegend |
| 176 | CD69 | FN50 | Biolegend |
| 191/193 | Ir intercalator | | Fluidigm |

The Helios-generated output files were normalized using EQTM Four Element Calibration Beads (Cat #201078, Fluidigm) according to manufacturer's instructions (Finck, et al. Cytometry A 83, 483-494 (2013).) and de-barcoded manually by Boolean Gating strategy in FlowJo (version 10.2; FlowJo LLC, USA). Each sample was down-sampled to 10,000 live immune cells and equal number of samples were selected for each group before analysis using an in-house enhanced Automatic Classification of Cellular Expression by Nonlinear Stochastic Embedding (ACCENSE) software based on the combination of Barnes-Hut SNE non-linear dimension reduction algorithm and a k-means clustering algorithm (Shekhar, et al. Proc Natl Acad Sci USA 111, 202-207 (2014)). Cellular and nodal views of 2D t-Distributed Stochastic Neighbour Embedding (t-SNE) maps and density plots for the expression of individual markers in each node were generated simultaneously. Nodes that were significantly enriched ($P<0.05$) in either group were identified by paired or unpaired Mann-Whitney U test. All data were validated independently using FlowJo. Both 2D and 3D heat maps were plotted based on all significant nodes using R script for data visualization.

Next-Generation Sequencing (NGS)

Tumour tissue from each patient was preserved in RNA Later (Thermo Fisher Scientific, USA) and stored at −80° C. until further processing. RNA was isolated using the mirVana miRNA Isolation Kit (Thermo Fisher Scientific) and cDNA was generated with the SMART-Seq® v4 Ultra™ Low Input RNA Kit for Sequencing (Clontech, USA), according to manufacturers' protocols. Illumina-ready cDNA libraries were generated from amplified cDNA using the Nextera XT DNA Library Prep Kit (Illumina, USA) and multiplexed for 2+ 101 bp-sequencing. NGS was performed externally at the Genome Institute of Singapore on a HiSeq High output platform.

Raw-sequencing reads were mapped via Hierarchical Indexing for Spliced Alignment of Transcripts (HISTAT) with reference to the Human Assembly GRCh38. p7. from Ensembl. Read alignments were then sorted using SAMtools and the raw gene counts were extracted with high-throughput sequencing data (HTSeq). The R package EdgeR tool was used for differential gene expression analysis between two sample groups. The empirical Bayes quasi-likelihood F-test was used in the Generalised Linear Model pipeline for gene-wise statistical analysis (Lund, et al. Stat Appl Genet Mol Biol 11, (2012)). Genes with a fold-change >2 and P<0.01 were selected. The data were then visualized in heat maps using R-Script and biological function analysis on enriched genes in post Y90 RE tumours was performed using the DAVID6.7 Functional Annotation Tool based on P<0.01 and benjamini <0.05 selection criteria. Additional functional pathway analysis of enriched genes was carried out using the Reactome Pathway Database (Croft, et al. Nucleic Acids Res 39, D691-697 (2011)).

Quantitative Polymerase Chain Reaction (q PCR)

RNA from tumour tissues was isolated as described above and cDNA conversion was performed using SuperScript IV Reverse Transcriptase (Thermo Fisher Scientific, USA) according to the manufacturer's instructions. Primer sequences for target genes are provided in Table 4. qPCR was performed using LightCycler®480 SYBR Green I Master (Roche, Switzerland) and data were collected using a LightCycler®480 II (Roche). Technical triplicates were performed and results were normalized against GAPDH expression to obtain an average of relative gene expression.

TABLE 4

Primer sequence for target genes

| Targets | SEQ ID NO. | Primer Sequence in 5'-3' orientation |
|---|---|---|
| CCL5-Forward | 36 | ACACACTTGGCGGTTCTTTC |
| CCL5-Reverse | 37 | CCTGCTGCTTTGCCTACATT |
| CXCL16-Forward | 38 | CTACACGAGGTTCCAGCTCC |
| CXCL16-Reverse | 39 | CAATCCCCGAGTAAGCATGT |
| GAPDH-Forward | 40 | ACCACAGTCCATGCCATCAC |
| GAPDH-Reverse | 41 | TCCACCACCCTGTTGCTGTA |

Prediction Modelling Algorithm

Random Forest algorithm (Breiman, Machine Learning 45, 5-32 (2001)) was used for building the model to predict the clinical response to Y90 RE. Single-cell CyTOF data (10,000 single cells with 37 markers expressions) from each patient from n=22 randomly selected patients was used for algorithm tuning and training and then tested on an independent validation or testing cohort of n=8 patients (FIG. 1). Caret (K. M, Journal of Statistical Software 28, (2008)) and Ranger (Wright, Journal of Statistical Software 77, (2017).) packages in R were used in the tuning and training of the random forest based on two parameters: mtry, the number of random variables in each tree, and ntree, the number of trees, for optimal accuracy (mtry=10 and ntree=2000 which provided maximum accuracy of 76.8% was chosen to tune the model—FIG. 2). For each of the samples, percentage of cells being classified as SR or NR was computed and used as a voting system for probability scores, where 50% as SR classified the samples in SR group while <50% as SR classified them in NR group. The results were compared with actual clinical outcomes and true- and false positive rates were plotted on a Receiver-Operating Characteristic (ROC) curve.

Figure 3:
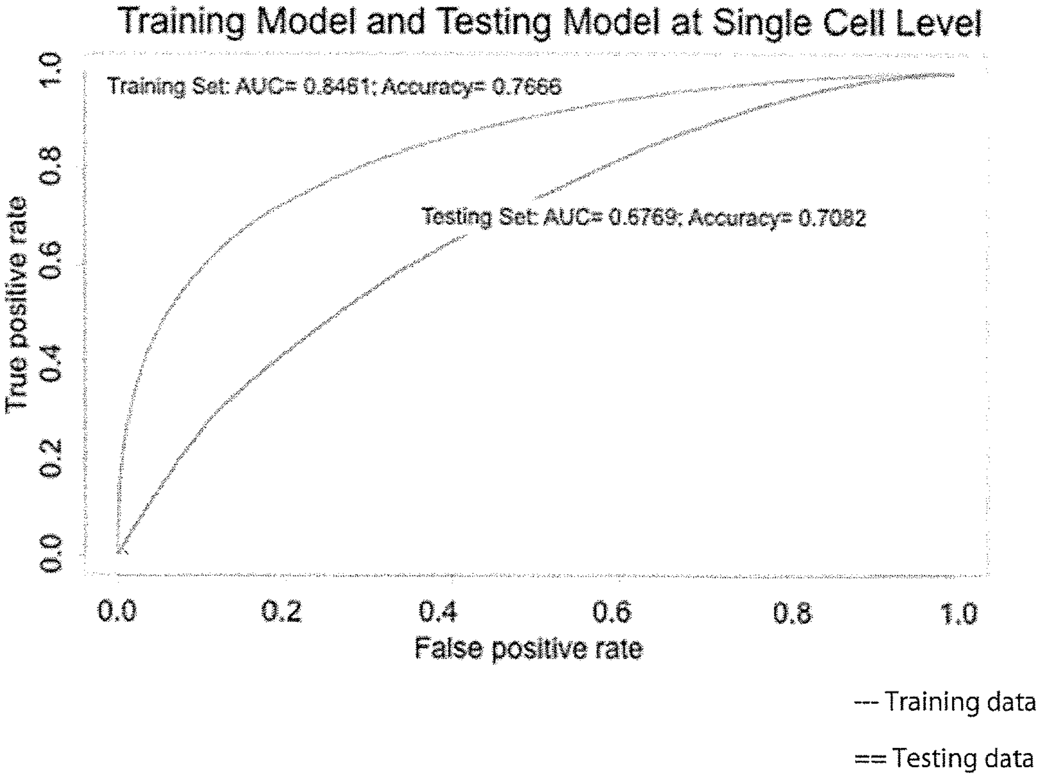
FIG. 3: ROC curve of training set model and testing set model at single cell level, using the final predictive model from random forest prediction modeling. Training set n=22: AUC=0.8461 and accuracy=0.7686; Testing set n=8: AUC=0.6769 and accuracy=0.7082 AUC=area under the curve.

Accuracy obtained for training and testing data at single cell level are 0.7686 and 0.7082 respectively (FIG. 3), with Area under the Curve (AUC) values of 0.846 and 0.677 respectively. For the training data, this means that there is 84.6% more likely that the training model will rank a randomly chosen positive R class single cell data higher than a randomly chosen negative class NR single cell data and 76.9% of the single cell data in the training dataset are correctly classified, as reference to the actual clinical outcomes demonstrate. In the testing data set, 70.8% of the single cell data are correctly classified. Sample level probability scores are then acquired using the simple cell level probability scores (FIG. 1, Tables 5 and 6). For each of the samples in the training or testing/validation cohort, number of cells being classified as class SR and class NR are computed. Percentages of cells being classified as class SR and class NR for each sample are computed (FIG. 1, Tables 5 and 6) and are used as a voting system to be treated as probability scores for class SR and class NR at whole sample level. In this final step, in order for a sample to be classified as class SR, the probability score of positive class SR for a sample data has to be equal to or greater than 50%, without which the sample will be classified as class NR. This final step of voting system generates highly accurate prediction outcomes, which gave an accuracy of 0.955 for the training data set and 0.750 for the testing data set. Both of the training and testing data sets obtained AUC value of 1 under the ROC curve (FIG. 2D). This means that, 95.5% of the training set samples are correctly classified, and there is 100% probability that the training model will rank a randomly chosen positive responder SR class sample higher than a randomly chosen negative class NR sample. This has the clear advantage that there is a high chance that all the NR class will be treated with the relevant composition comprising a SIRT and an immunotherapy and even where an SR is predicted to be an NR where treatment with SIRT alone would be sufficient the combined treatment of a composition comprising a SIRT and an immunotherapy should still result in a response. The dendrogram showing distance between samples in both training and testing/validation cohort is depicted in FIG. 2A. Median expression values for individual markers are used.

TABLE 5

| Prediction outcome for training cohort n = 22 | | | | | | |
|---|---|---|---|---|---|---|
| Pat ID | No of cells predicted as SR | No of cells predicted as NR | Prob_SR (%) | Prob_NR (%) | Pre-dicted | Ac-tual |
| HEP011 | 1502 | 8498 | 15.02 | 84.98 | NR | NR |
| HEP053 | 2214 | 7786 | 22.14 | 77.86 | NR | NR |
| HEP056 | 8892 | 1108 | 88.92 | 11.08 | SR | SR |
| HEP099 | 920 | 9080 | 9.2 | 90.8 | NR | NR |
| HEP128 | 6103 | 3897 | 61.03 | 38.97 | R | R |
| HEP131 | 9488 | 512 | 94.88 | 5.12 | R | R |
| HEP147 | 8671 | 1329 | 86.71 | 13.29 | R | R |
| HEP161 | 373 | 9627 | 3.73 | 96.27 | NR | NR |
| HEP167 | 2051 | 7949 | 20.51 | 79.49 | NR | NR |
| HEP188 | 589 | 9411 | 5.89 | 94.11 | NR | NR |
| HEP201 | 6335 | 3665 | 63.35 | 36.65 | R | R |
| HEP205 | 2437 | 7563 | 24.37 | 75.63 | NR | NR |
| HEP210 | 5944 | 4056 | 59.44 | 40.56 | R | R |
| HEP242 | 5606 | 4394 | 56.06 | 43.94 | R | R |
| HEP258 | 2659 | 7341 | 25.59 | 73.41 | NR | NR |
| HEP279 | 1197 | 8803 | 11.97 | 88.03 | NR | NR |
| HEP281 | 3211 | 6789 | 32.11 | 67.89 | NR | R |
| HEP286 | 5150 | 4028 | 56.11 | 43.89 | R | R |
| HEP291 | 855 | 9145 | 8.55 | 91.45 | NR | NR |
| HEP292 | 755 | 9245 | 7.55 | 92.45 | NR | NR |
| HEP298 | 5550 | 4023 | 57.98 | 42.02 | R | R |
| HEP313 | 1256 | 8744 | 12.56 | 87.44 | NR | NR |

TABLE 6

| Prediction outcome for testing cohort n = 8 | | | | | | |
|---|---|---|---|---|---|---|
| Pat ID | No of cells predicted as SR | No of cells predicted as NR | Prob_SR (%) | Prob_NR (%) | Pre-dicted | Ac-tual |
| HEP022 | 1103 | 8897 | 11.03 | 88.97 | NR | NR |
| HEP023 | 2873 | 7127 | 28.73 | 71.27 | NR | NR |
| HEP266 | 808 | 9192 | 8.08 | 91.92 | NR | NR |
| HEP272 | 3500 | 6500 | 35 | 65 | NR | NR |
| HEP278 | 1241 | 8759 | 12.41 | 87.59 | NR | NR |
| HEP294 | 1930 | 8070 | 19.3 | 80.7 | NR | NR |
| HEP179 | 4604 | 5396 | 46.04 | 53.96 | NR | SR |
| HEP316 | 3506 | 6494 | 35.06 | 64.94 | NR | SR |

The single cell training model and sample based voting system, provides highly accurate prediction of response to SIRT Y90 RE than any other clinical parameters.

Figure 4:
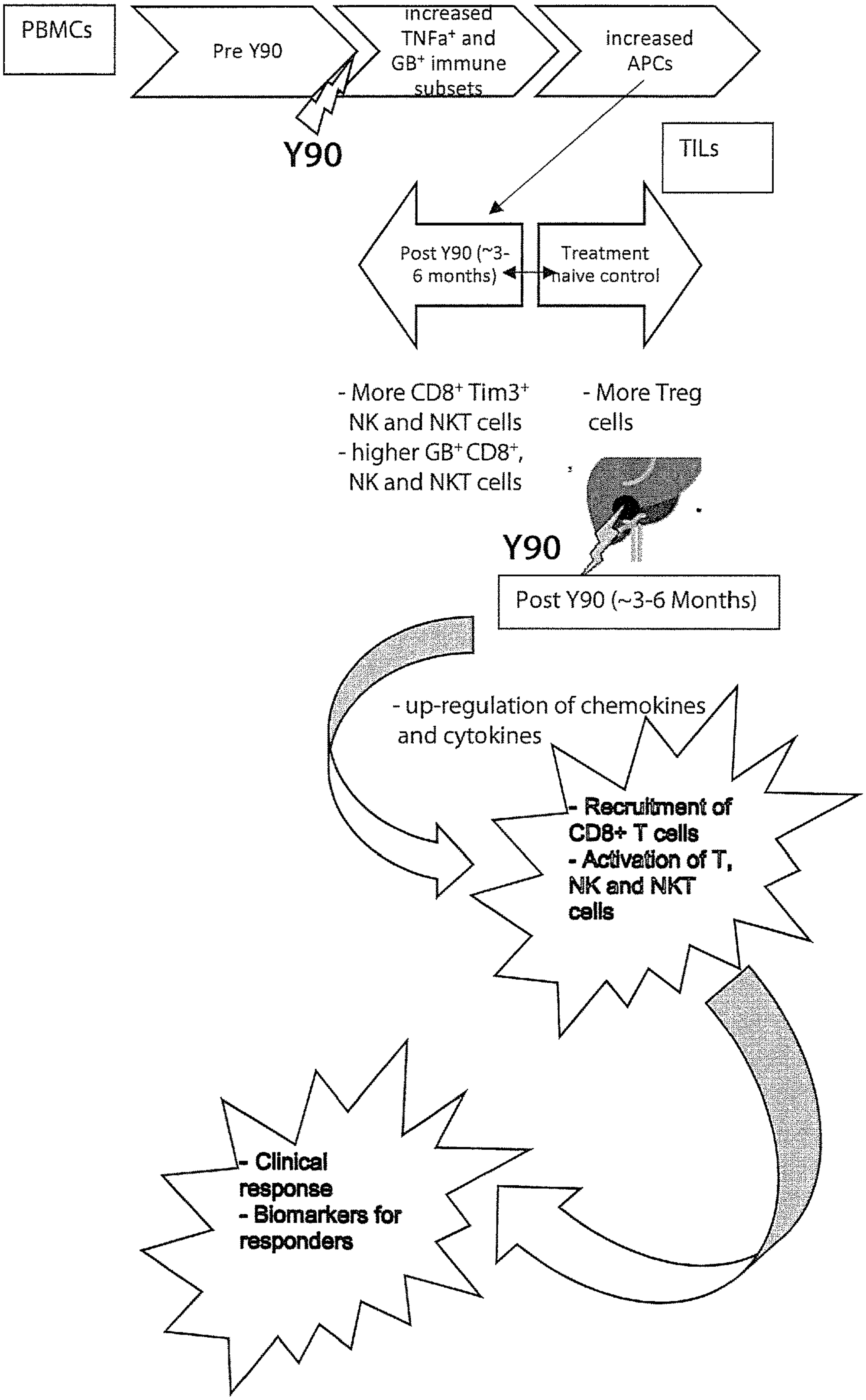
FIG. 4: Prediction model for sustained response to Y90-RE showing a series of immune responses induced by Y90-RE in tumor infiltrating lymphocytes (TILs) and PBMCs. In TILs from Y90-RE treated tumors (resections were performed between 3 to 6 months after Y90-RE upon successful downstaging), an increase in infiltration of GB-expressing CD8+, natural killer (NK) cells and NKT cells was observed after Y90-RE versus more TREG in the treatment-naïve control tumors. Y90-RE-induced upregulation of chemokines within tumor microenvironment is hypothesized to link to CD8+ T cells recruitment and activation. In PBMCs on the other hand, at 1 month (1 mo) and 3 months (3 mo) post-Y90-RE, immune activation of TNFα-expressing and granzyme B (GB)-expressing immune subsets and antigen-presenting cells (APCs) was observed.

Prediction Model for Sustained Response based on the Immune Profiles of pre-Y90 PBMCs Based on the differences in immune markers expression from the peripheral blood, the patients who demonstrated sustained response from the patients who showed no or transient response to Y90-RE were segregated. Next, a prediction model was built using Random Forests for predicting sustained response based on single-cell immune profiles (CyTOF data from 10,000 single cells with 37 markers expressions) of pre-Y90 PBMCs (FIG. 2A). The prediction model was selected based on the parameters: mtry (number of random variables) and ntree (number of trees) that provided the optimal accuracy (mtry=10 and ntree=2000 provided maximum accuracy of 76.8%, FIG. 2B). A high accuracy of 95.5% was found when cross-validating this model in the training cohort (n=22) and accuracy of 75.0% when independently tested in a testing cohort (n=8) (FIG. 2D and table 5 and 6). Taken together, this in-depth immunophenotyping approach has demonstrated the nature of the immune response after Y90-RE at the local and systemic level. Potential systemic biomarkers have been identified that classify and predict HCC patients who showed sustained response to Y90-RE (FIG. 4).

Multivariate Analysis of Variance

In order to consider other clinical parameters potentially influencing the clinical outcome or response to Y90-RE, multivariate analysis of variance was performed to analyze the relationships between the actual clinical response with the prediction model described herein as well as other clinical parameters which may influence outcome/response. For Multivariate Analysis of Variance (Manova—Xu and Cui. Bioinformatics 2008; 24:1056-62), the F-value and p-value were calculated based on Pillai-Bartlett trace statistic (Muller and New. J Comput Graph Stat 1998; 7:131-7) These parameters include: Stage, tumor multiplicity, tumor size, portal vein tumor thrombus (PVTT), alpha-fetoprotein (AFP) level, Hepatitis status and pre or post therapy prior or after Y90-RE (Table 7).

TABLE 7

| Clinical and samples collection information for HCC patients treated with Y90-RE-1 | | | | | | | | | | |
|---|---|---|---|---|---|---|---|---|---|---|
| No. | Pat ID | Pre | 1 mo | 3 mo | 6 mo | TIL | 3 m RECIST 1.1 | 6 m RECIST 1.1 | Location of progressi | Response status |
| 1 | HEP011 | X | X | | | | PD | PD | Non target (Distant) | NR |
| 2 | HEP023 | X | X | | | | PD | PD | Non target (Distant) | NR |
| 3 | HEP053 | X | | X | X | | SD | PD | Target | TR |
| 4 | HEP099 | X | | X | | | PD | PD | Non target (Distant) | NR |
| 5 | HEP167 | X | | X | X | | PD | PD | Non target (Distant) | NR |
| 6 | HEP205 | X | X | | | | PD | PD | Non target (Distant) | NR |
| 7 | HEP278 | X | X | X | X | | SD | PD | Non target (fiver) | TR |
| 8 | HEP272 | X | X | X | | | PD | PD | Target | NR |
| 9 | HEP022 | X | X | X | | | SD | PD | Non target (Distant) | TR |
| 10 | HEP279 | X | | X | | X | SD | PD | Non target (liver) | TR |

TABLE 7-continued

Clinical and samples collection information for HCC patients treated with Y90-RE-1

| | | | | | | | | | | |
|---|---|---|---|---|---|---|---|---|---|---|
| 11 | HEP161 | X | | | | | PD | PD | Target | NR |
| 12 | HEP188 | X | | | | | PD | PD | Non target (Distant) | NR |
| 13 | HEP258 | X | X | | | | PD | PD | Non target (Distant) | NR |
| 14 | HEP286 | X | X | | | | PD | PD | Non target (Distant) | NR |
| 15 | HEP291 | X | X | X | X | | PD | PD | Non target (Distant) | NR |
| 16 | HEP292 | X | | | | | PD | PD | Non target (Distant) | NR |
| 17 | HEP294 | X | | | X | | SD | PD | Non target (liver) | TR |
| 18 | HEP313 | X | | X | | | PD | PD | Non target (Distant) | NR |
| 19 | HEP128 | X | X | | | | PR | PR | — | SR |
| 20 | HEP131 | X | | X | X | | PR | PR | — | SR |
| 21 | HEP147 | X | X | X | | | SD | SD | — | SR |
| 22 | HEP056 | X | X | | X | | SD | SD | — | SR |
| 23 | HEP179 | X | X | X | X | | PR | PR | — | SR |
| 24 | HEP201 | X | X | | | | PR | PR | — | SR |
| 25 | HEP132 | | X | | | | SD | SD | — | SR |
| 26 | HEP210 | X | | X | X | X | PR | PR | — | SR |
| 27 | HEP242 | X | | X | X | X | PR | PR | — | SR |
| 20 | HEP281 | X | | X | | | SD | SD | — | SR |
| 29 | HEP286 | X | | X | | X | PR | PR | — | SR |
| 30 | HEP298 | X | X | X | | | PR | PR | — | SR |
| 31 | HEP316 | X | X | | | | SD | SD | — | SR |

| No. | Tumor multiplicit | Tumor size (cm) | Stage (TNM) | PVTT | AFP level (μg/ml) | Hepatitis status | Pre tx | Post tx |
|---|---|---|---|---|---|---|---|---|
| 1 | Multifocal | 3.2 | IVB | No | 16841.0 | B | Yes | No |
| 2 | 1 | 9.1 | IIIB | Yes | 2047.0 | B | Yes | No |
| 3 | Multifocal | 1.7 | IIIB | Yes | 210.0 | B | Yes | Yes |
| 4 | Multifocal | 2.2 | IIIB | Yes | 402.0 | C | Yes | Yes |
| 5 | Multifocal | 7.2 | IIIB | Yes | 171.0 | Non | Yes | Yes |
| 6 | 1 | 10.0 | IIIA | No | 6.3 | B | No | No |
| 7 | Multifocal | 3.0 | II | No | 15.9 | Non | No | Yes |
| 8 | 1 | 16.0 | I | No | 2.3 | Non | No | No |
| 9 | Multifocal | 2.5 | II | Yes | 252.0 | B | Yes | Yes |
| 10 | Multifocal | 8.4 | IIIA | No | 202.0 | B | No | Yes |
| 11 | Multifocal | 3.7 | IIIb | Yes | 499.0 | Non | No | Yes |
| 12 | Multifocal | 10.6 | IIIB | Yes | 62.4 | Non | No | Yes |
| 13 | Multifocal | 2.7 | IIIB | Yes | 60500.0 | C | Yes | No |
| 14 | Multifocal | 8.3 | IIIA | No | 122.0 | B | No | No |
| 15 | Multifocal | 6.2 | IIIB | Yes | 3.7 | B | No | Yes |
| 16 | Multifocal | 5.7 | IIIB | No | 17818.0 | Non | Yes | No |
| 17 | 1 | 9.9 | I | No | 521.0 | B | Yes | Yes |
| 18 | Multifocal | 10.0 | IIIA | No | 4281.0 | Non | Yes | Yes |
| 19 | 1 | 10.3 | II | Yes | 97.5 | B | Yes | Yes |
| 20 | 1 | 5.5 | I | Yes | 9.9 | B | No | Yes |
| 21 | Multifocal | 9.8 | IIIA | Yes | 67.7 | Non | No | No |
| 22 | 1 | 10.0 | I | No | 4718.0 | C | Yes | Yes |
| 23 | 1 | 5.1 | IIIB | Yes | 149.0 | Non | Yes | Yes |
| 24 | Multifocal | 3.9 | II | Yes | 165.0 | C | Yes | No |
| 25 | 1 | 12.6 | I | No | 3.9 | Non | Yes | No |
| 26 | Multifocal | 6.4 | I | No | 38.0 | B | No | Yes |
| 27 | 1 | 11.1 | I | No | 14.4 | B | No | Yes |
| 20 | 1 | 6.0 | I | No | 6.4 | C | No | No |
| 29 | 1 | 6.7 | I | No | 90.2 | B | No | Yes |
| 30 | 1 | 6.4 | I | No | 3.2 | Non | No | No |
| 31 | Multifocal | 7.0 | IIIA | No | 4.0 | C | Yes | No |

As shown in Table 8, the prediction model described herein was superior in predictive power (p=1.006e-07) compared to stage (p=0.0012); or tumor multiplicity (p=0.014) or any of the other parameters which do not have significant predictive power. This indicated that the immune status of pre-Y90-RE PBMC could serve as a better biomarker than other clinical parameters in predicting sustained response to Y90-RE. Accordingly the prediction model described herein is highly superior.

TABLE 8

Multivariate Analysis of Variance (Manova)

| Variables | F value | p value |
|---|---|---|
| Prediction Model | 50.4000 | $1.006e^{-07}$*** |
| Tumor multiplicity | 6.8923 | 0.01387* |
| Tumor Size | 0.2748 | 0.6042 |
| Stage | 13.0980 | 0.001155** |
| AFP Level | 1.5452 | 0.2242 |
| PVTT | 0.1888 | 0.6673 |
| Hepatitis Status | 0.0265 | 0.8718 |
| Pre-Y90-RE tx | 0.5283 | 0.4734 |
| Post-Y90-RE tx | 0.0216 | 0.8842 |

F-value = value calculated From F-statistic
p value =
p < 0.001***
p < 0.01 **
p < 0.05 *

Statistical Analyses

For CyTOF data, non-parametric paired or unpaired Mann-Whitney U tests were used to identify differential nodes between the two groups. A paired or unpaired Student's t-test or Mann-Whitney U-test and Pearson's correlation test GraphPad Prism V.6.0f) was used to analyse the FlowJo and qPCR data, as indicated.

General Response to Y90-RE Treatment

The data obtained from analysing resected tumour tissue and PBMCs from patients with HCC, provide strong evidence that Y90-RE induces both a localized and systemic immune response that involves T cell, NK cell and NKT cell activation, antigen presentation and immune-cell motility. Systemic immune subsets unique to patients who demonstrated sustained-response to Y90-RE included, exhaustion markers (PD-1 and Tim-3)-expressing CD8+ T cells and CD4+ T cells and homing receptors (CCR5 and CXCR6)-expressing CD8+ T cells and CD8+Tim3+ T cells. A chemotaxis pathway triggered by Y90-RE for activated GB+CD8+ T cells via CCL5 and CXCL16 was also discovered. Importantly, the current study provided a prediction model for sustained clinical response based on the immune profiles of the pre-Y90-RE PBMCs.

In-depth immunophenotyping of TILs showed marked immune activation in the local tumour microenvironment, such as an increase in activated or GB-expressing-CD8+ T cells, -CD56+ NK cells and -CD8+CD56+ NKT cells and reduced TREG cells post-Y90-RE. Analysis of NGS data from tumour tissues also provided compelling evidence for enhanced T cell, NK cell and NKT cell activation. For instance, in patients that received Y90-RE, an induction of CD28 co-stimulatory and CD28-dependent Vav1 and Akt pathways was observed, which have been previously shown to positively regulate T-cell activation and proliferation (Charvet, The Journal of Immunology 177, 5024-5031 (2006)). The CyTOF and NGS analyses also identified an enhanced innate immune response as a result of Y90-RE that involved NK cells and NKT cells activation.

Y90-RE Activates the Local Immune Response

Figure 5:
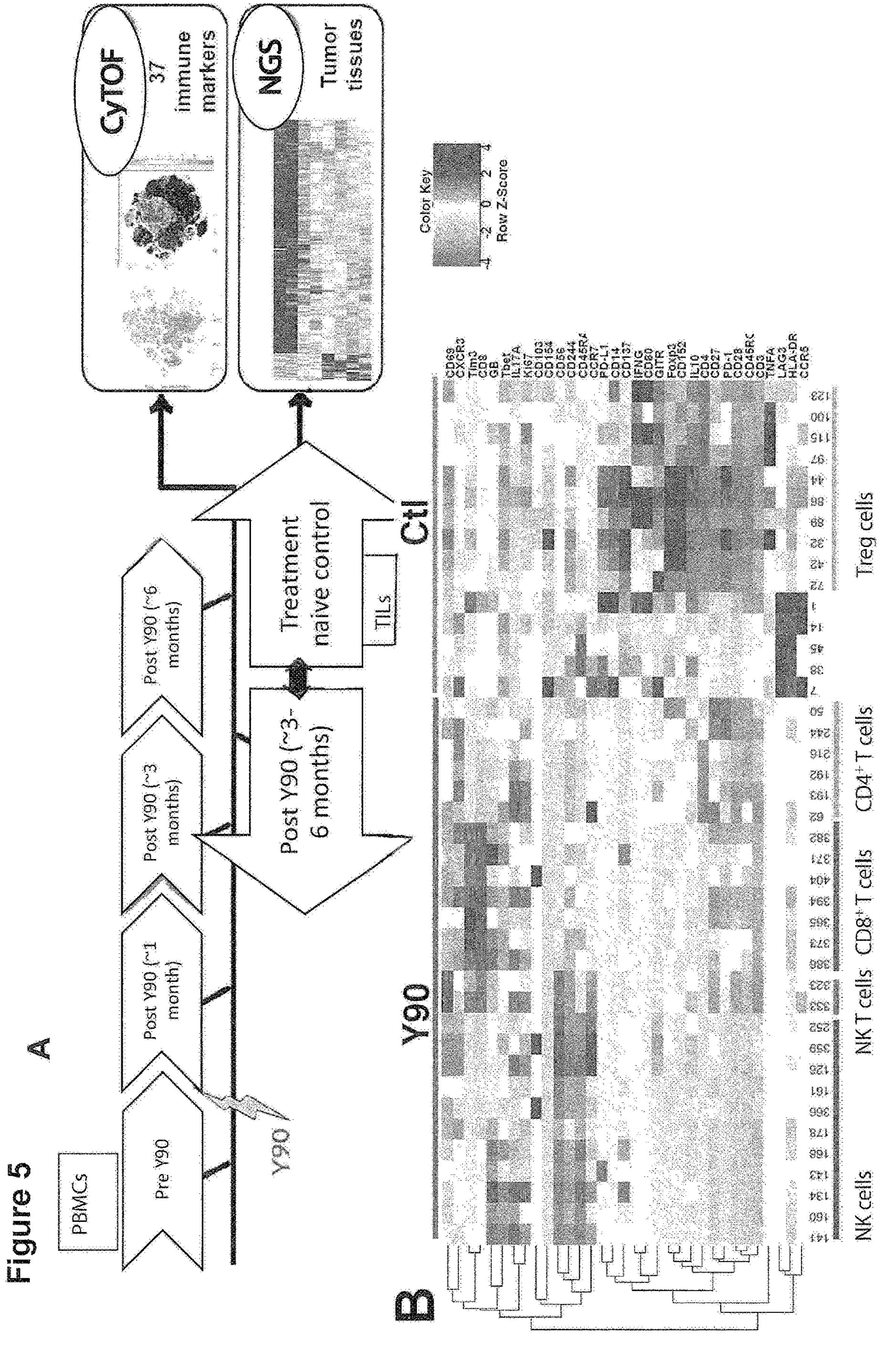
FIG. 5: Immune profiles of tumor infiltrating leukocytes (TILs) isolated from Y90-RE-treated and treatment-naive tumors A. Samples collection and analysis pipeline. PBMCs were collected before (Pre Y90) and at various time points after Y90-RE (Post Y90) (n=31 patients). TILs were collected from resected HCC tumors from post Y90-RE (downstaged upon therapy) or treatment-naive patients, Ctl (n=7 for each group). CyTOF was used to analyze both the PBMCs and TILs and NGS was performed on tumor tissues from post-Y90-RE and treatment naive patients (n=4 for each group). B. 2D heat map showing the differential expression of immune markers by nodes enriched in TILs isolated from post Y90-RE (upper left bar) or treatment naive (Ctl; upper right bar) HCC tumors. Enriched immune subsets in TILs from post Y90-RE were CD56+ natural killer (NK) cells, CD8+CD56+ NKT cells, CD8+Tim3+ T and CD4+CD45RO+ T cells while regulatory T, Treg cells were enriched in TILs from Ctl HCC (grey scale-coded lines). n=7 each group.

An in-depth analysis pipeline based on CyTOF and NGS was designed to survey the immune phenotypes of TILs, tumour tissues and PBMCs obtained from patients with HCC before and after undergoing Y90-RE (FIG. 5A). In order to understand the nature of the local immune response, TILs were isolated from patients after Y90-RE or from patients who were treatment-naive (with matched clinical parameters, as control, Ctl, Table 1). TILs were analysed using CyTOF (Table 3) and the differentially expressed nodes/immune-subsets from post-Y90-RE versus Ctl tumors were identified (FIG. 5B).

Figure 6:
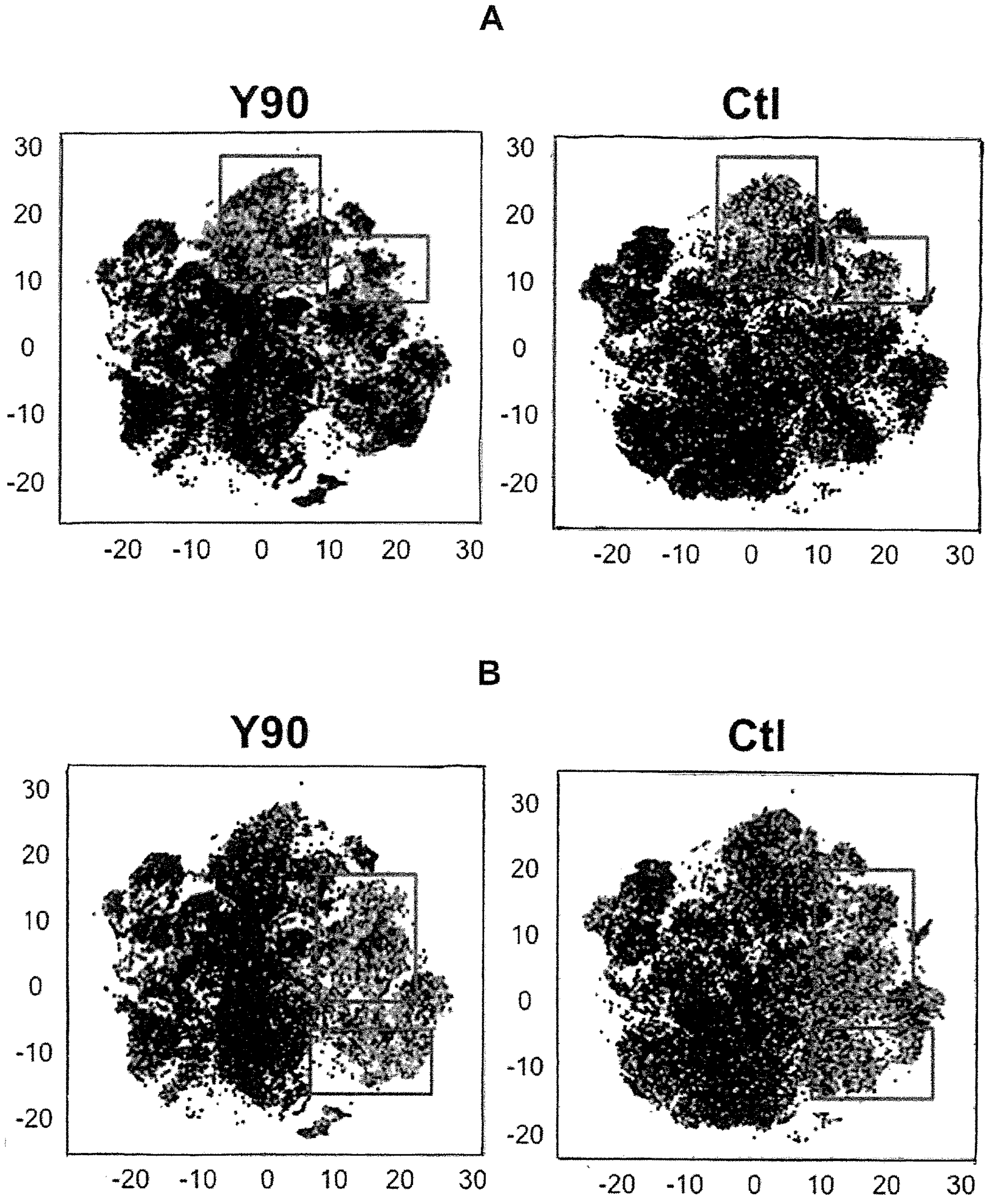
FIG. 6. 2D representation of A granzyme B (GB) and B Tim-3 expression on TILs isolated from post-Y90-RE (Y90) and Ctl HCC tumors. Images were generated using inhouse enhanced ACCENSE software.
Figure 7:
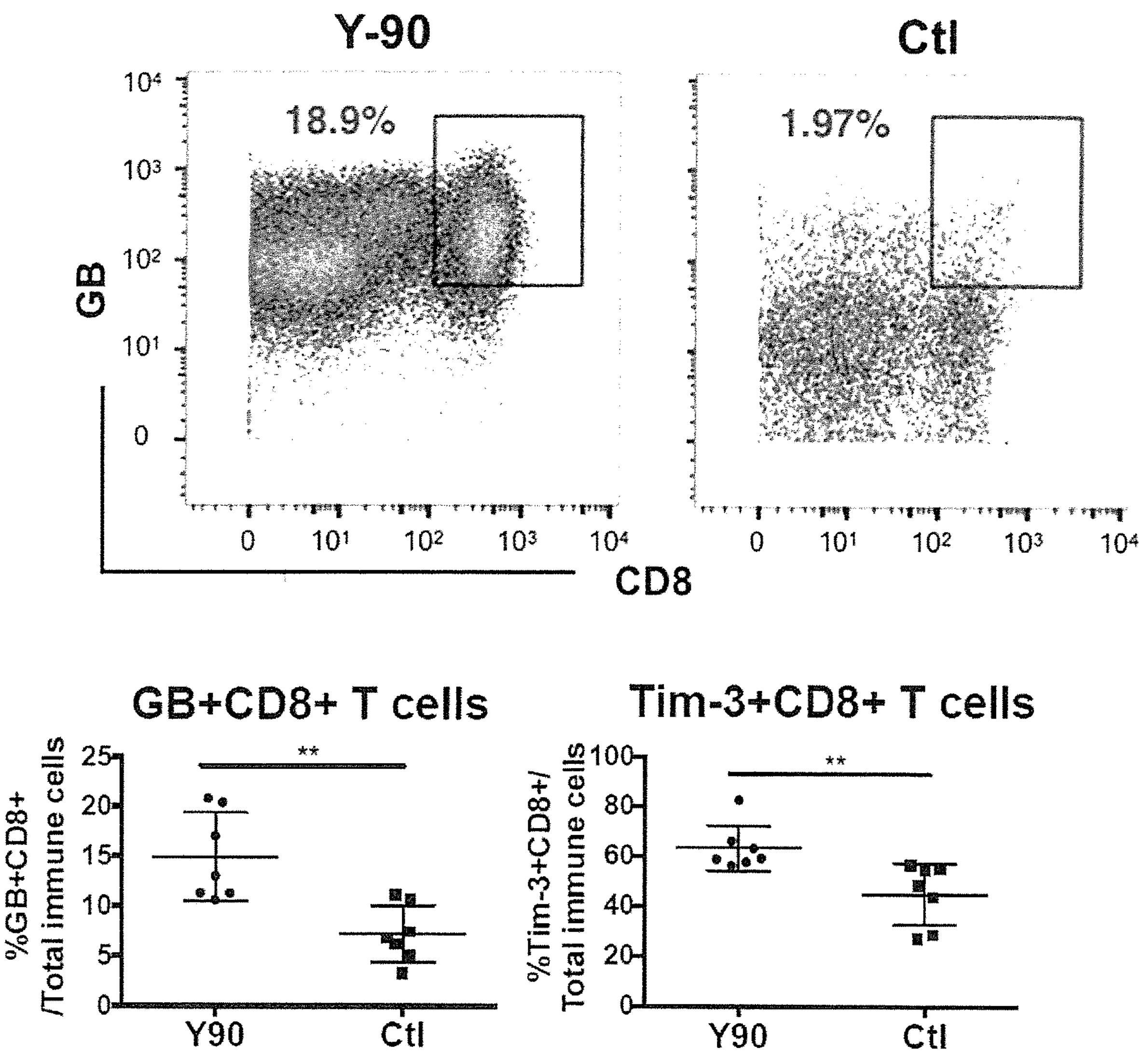
FIG. 7. Representative plots showing the gating of GB on CD8+ T cells from post-Y90-RE (Y90) or Ctl TILs (Top panel). Percentage of GB+CD8+ and Tim-3+CD8+ T cells from post-Y90-RE and Ctl TILs (bottom panel).
Figure 8:
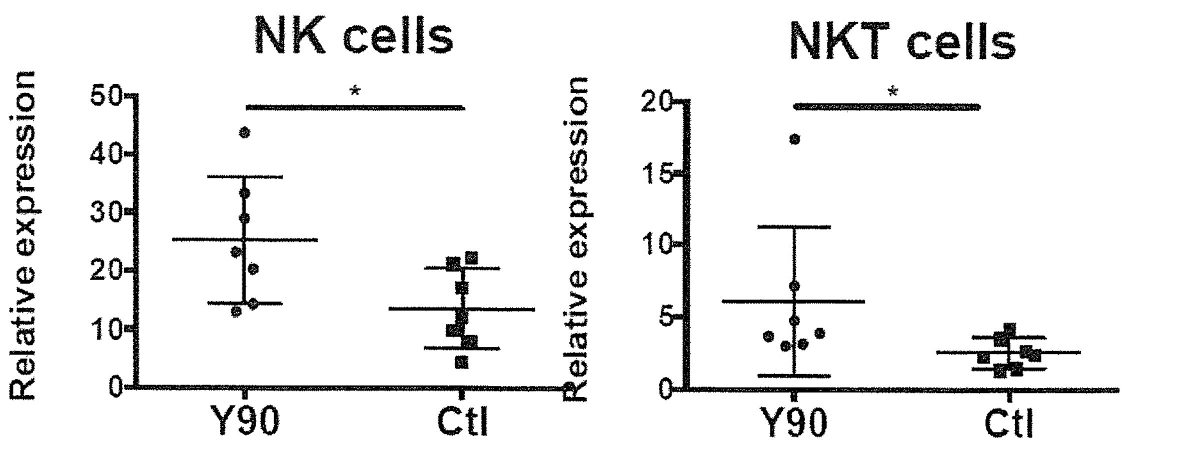
FIG. 8. Percentage of CD56+ NK cells, CD8+CD56+ NKT cells, GB+CD56+ NK cells and GB+CD8+CD56+ NKT cells from post-Y90-RE (Y90) and Ctl TILs. Graphical data represent the means±standard deviations and were analyzed by unpaired Student's t-test. *$P<0.05$ and **$P<0.01$.
Figure 8:
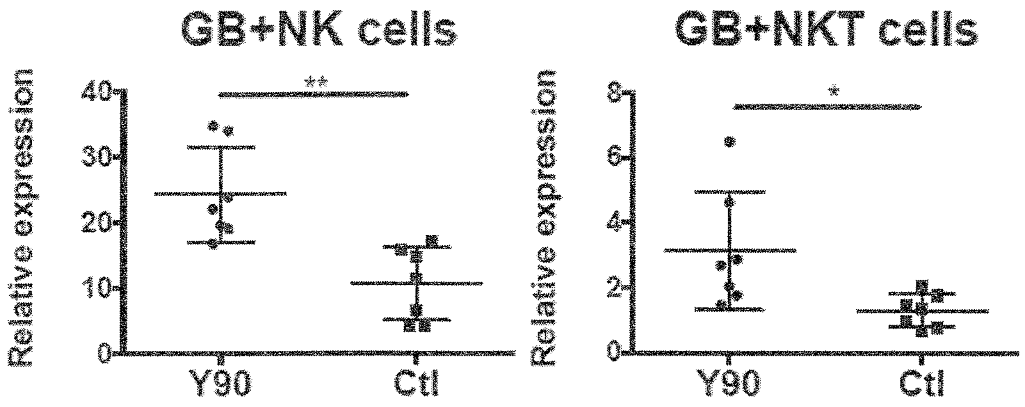
Figure 9:
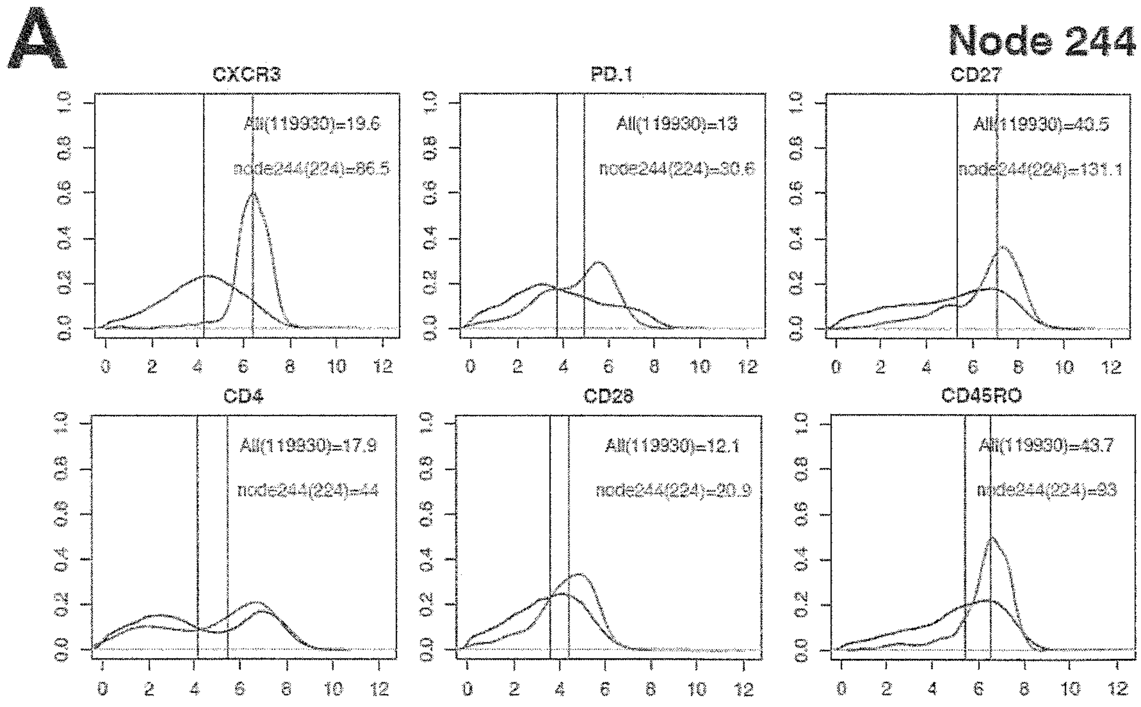
FIG. 9: Immune profiles of TILs from post-Y90 RE or treatment naive tumors. A density plots showing CXCR3 and CD45RO expression from representative nodes, NODE 244 representing CD4+ population that was enriched in TILs from post Y90 RE tumors. Grey plots show expression profiles from the selected node and black plots show expression profiles of all the nodes. Grey and black lines represent the average expression level of each marker. B graphs show percentages of CXCR3+CD4+CD45RO+ T cells in TILs from post Y90 RE (Y90) and treatment naïve (Ctl) tumors. Graphs represent the means±SDs and were analyzed by unpaired Student's t-test. *$p<0.05$.
Figure 9:
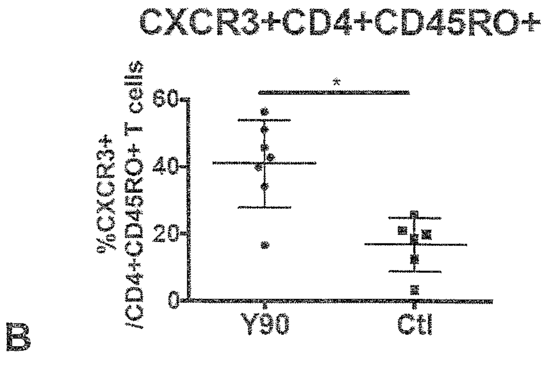
Figure 10:
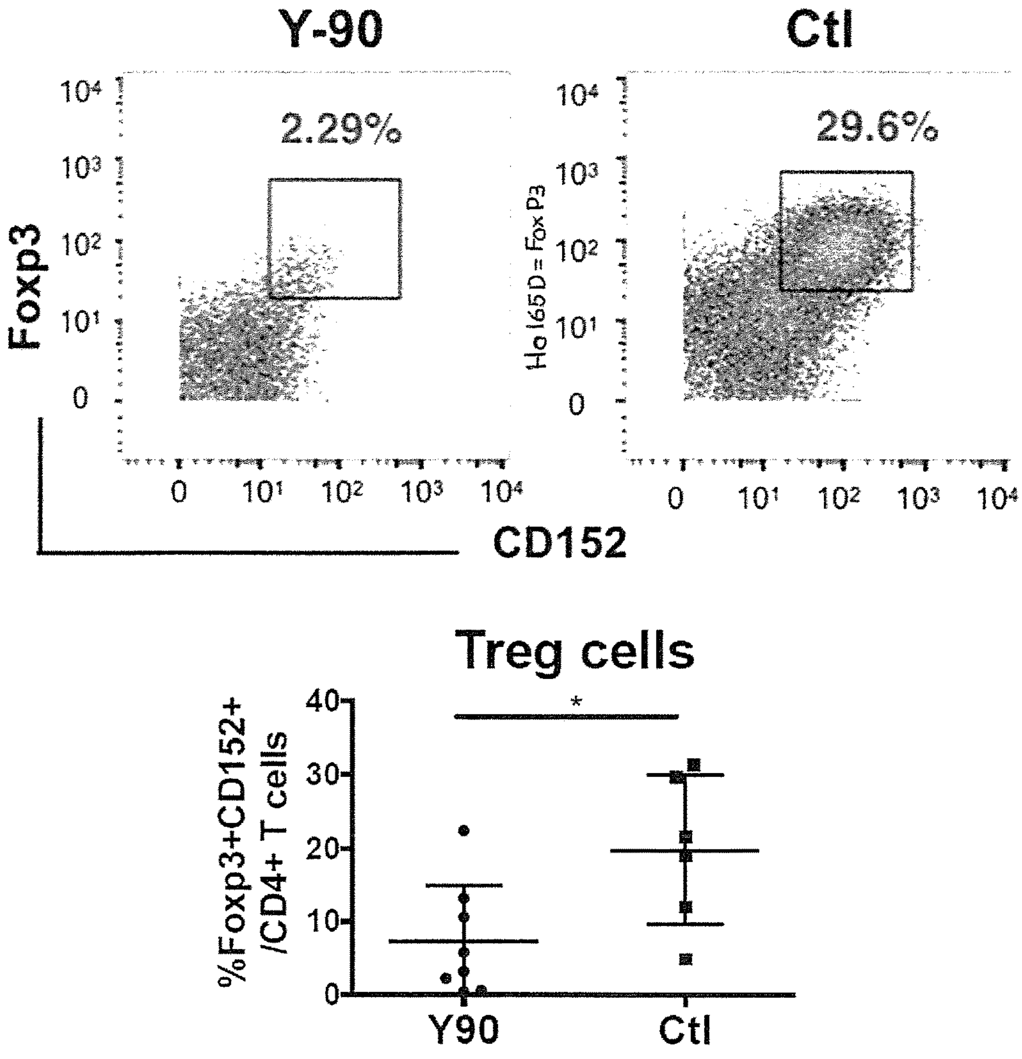
FIG. 10: Immune profiles of TILs from post-Y90 RE or treatment naive tumors. Representative plots showing the gating of Foxp3+CD152+ Treg cells on pre-gated CD4+ T cells from post Y90 RE (Y90) and treatment naive (Ctl) TILs. Right, graphs shows percentage of Treg cells. Data show means±SDs and were analyzed by unpaired Student's t-test. *$p<0.05$.

An enrichment of specific CD56+ NK cells, CD8+CD56+ NKT cells, CD8+ T cells and CD4+ T cell subsets in TILs isolated from post-Y90-RE tumours was observed (FIG. 5B). The expression of two immune markers, granzyme B (GB) and Tim-3, was higher in TILs from post-Y90-RE versus Control (Ctl) tumours (FIGS. 6A & B). Indeed, a higher percentage of GB+CD8+ T cells and Tim-3+CD8+ T cells were detected in post-Y90-RE TILs as confirmed using FlowJo manual gating (FIG. 7). An overall enrichment of CD56+ NK cells and CD8+CD56+ NKT cells, which expressed significantly more GB than the Ctl TILs, was also observed in post-Y90-RE TILs (FIG. 8). In addition, a higher percentage of CD4+CD45RO+ T cells that expressed CXCR3 in post Y90-RE-TILs was observed (FIG. 5B and FIG. 9). Conversely, Ctl TILs showed a higher percentage of Foxp3+CD152+CD4+ TREG cells (FIG. 5B and FIG. 10) as compared to Y90-RE TILs. Taken together, these data show that the immune microenvironment of post-Y90-RE tumours was infiltrated by multiple activated immune subsets and was less immunosuppressive compared to the TREG cells-enriched Ctl tumours.

Immune Activation Pathways are Induced in the Tumor Tissue Following Treatment with Y90-RE NGS was performed on the resected tumour tissues collected from HCC patients downstaged after Y90-RE comparing to patients who did not receive any prior treatment as Ctl (Table 1). Overall, it was observed that multiple differentially expressed genes, with 88% of highly expressed genes in post-Y90-RE compared to Ctl tumours. Functional analysis using DAVID pathway analysis tool found that most of these enriched genes were related to innate or adaptive immune responses. Conversely, the genes enriched in Ctl tumours were not related to immune pathways.

Further data analysis of these post Y90-RE-enriched genes using the Reactome database identified pathways including the antigen presentation of MHC class II molecule; T-cell activation pathways, that were related to the CD28 co-stimulatory and CD28-dependent Vav1 and Akt pathways. Comparing post-Y90-RE versus Ctl tumours, upregulation of the NK cell activation pathway via CD244 and CD48 was also detected, as well as enrichment of LFA-1 and ICAM-1 binding, which is required for the development and recruitment of NKT cells to the liver. Taken together, these findings complement the observations by CyTOF of an enhanced activation and recruitment of T- NK- and NKT-cells into post-Y90-RE tumours.

Y90-RE Induces Chemotaxis of CD8+ T Cells to the Tumor Microenvironment

Figure 11:
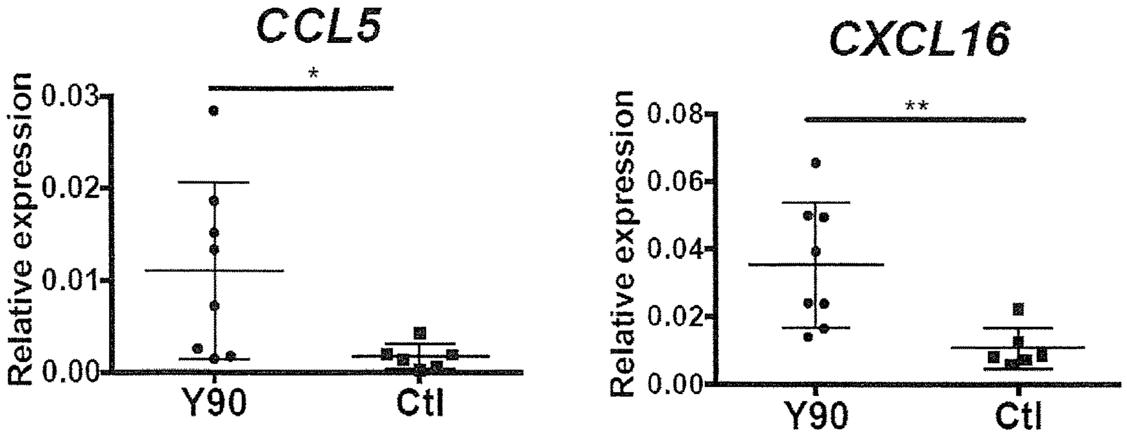
FIG. 11: Chemotatic pathways involving CCL5 and CXCL16 induced by Y90-RE. A. RNA expression of CCL5 and CXCL16 in Y90-treated (n=8) versus Ctl (n=6) tumor tissues by quantitative PCR analysis. B Correlation between RNA expression of CCL5 and CXCL16 and the percentage of tumor-infiltrating GB+CD8+-activated T cells (n=14). Graphical data represent the means±standard deviations. P values and correlation coefficients (r) were calculated using the Pearson's correlation test. *P<0.05 and **P<0.01.
Figure 11:
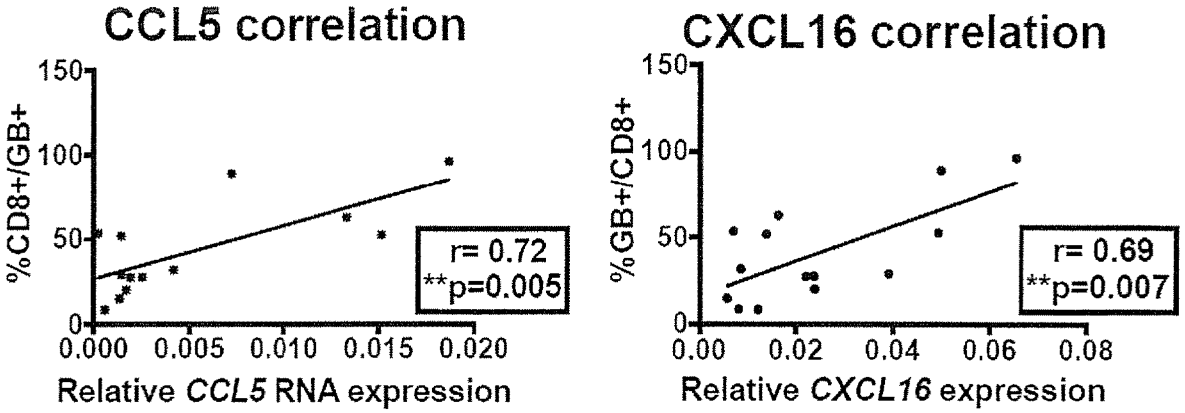

Reactome analysis on post-Y90-RE-enriched genes also indicated an increase in chemotactic activity involving the up-regulation of CXCL16 and CCL5 (FIG. 11). Given this result, it was hypothesized that a chemotaxis pathway may be induced by Y90-RE.

qPCR was then performed on tumour samples (Table 1) obtained from the same patients to validate the NGS results, which indeed showed an increase in CCL5 and CXCL16 expression—two chemokines that bind CCR5 and CXCR6, respectively (FIG. 11A). In order to confirm their chemotactic effect for activated T cells, the RNA expression of CCL5 and CXCL16 was correlated with the immune subsets found in TILs and confirmed that CCL5 and CXCL16 were positively correlated with percentage of activated GB+CD8+ T cells (FIG. 11B). These findings demonstrated the ability of Y90-RE to shape the microenvironment of HCC tumours, not only by inducing tumour-cell death but T-cell recruitment and activation following therapy.

Early and Late Immune Responses are Induced by Y90 Radioembolization

In order to capture the Y90-RE-induced systemic immune response, PBMCs from another 31 HCC patients were collected before and at various time points (1, 3 and 6-months) after Y90-RE (Table 2).

The 31 patients who received Y90-RE were segregated into two groups—Sustained responders (SRs) and non- or transient-responders (NRs/TRs) (Table 2; SRs are patients without progressive disease at any site (Non-PD) at 6 months after Y90 RE; NRs are patients who did not show even stable disease (SD) at 3 months and TRs are patients who showed initial response at 3 months but progressed by 6 months) and performed paired-wise time-points CyTOF analyses specifically on the SRs (FIG. 4). Initial indications of immune activation were represented by an increase in TNFα expression on CD8+Tim3+ and CD4+ T cells 1-month after Y90-RE, specifically in the SRs (FIG. 12A and FIG. 12B). Notably, TNFα expression on these T-cell subsets was significantly higher in SRs versus NRs/TRs at 1- and 3-months after therapy (FIG. 12A and FIG. 12B).

The same comparisons were made between 3-months and pre-Y90-RE and a significantly higher proportion of CD14+ HLADR+ antigen presenting cells (APCs) was observed 3-months after therapy specifically in SRs (FIG. 12C and FIG. 12D). GB+CD56+NK cells were also significantly enhanced at 3-months but this elevation was only specific to SRs at 1-month post-Y90-RE (FIG. 12E). A less distinct difference in immune-cell subsets was identified when comparing PBMCs at 6-months with pre-Y90-RE except APCs (FIG. 12C).

Prediction of Response to Y90_RE Treatment

Figure 12:
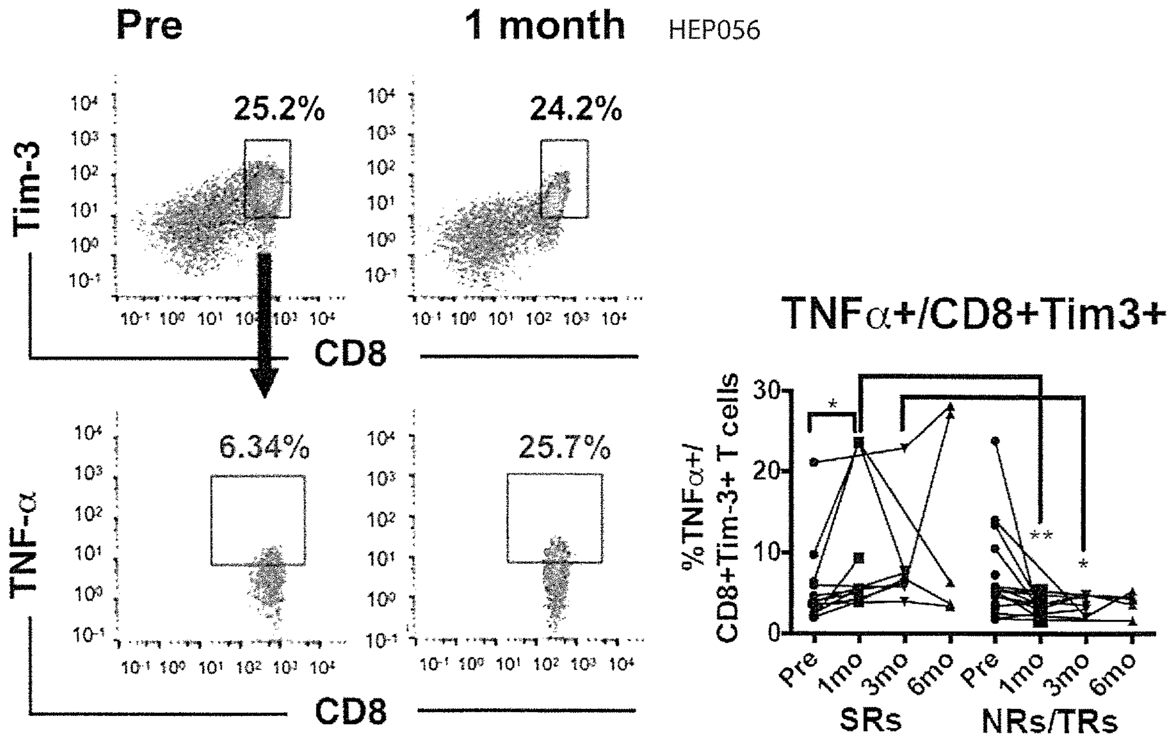
FIG. 12: Immune profiles of PBMCs from responders versus non responders to Y90 RE linked to clinical response detected in peripheral blood mononuclear cells (PBMCs) at 1 month and 3 months post-Y90-RE. A Representative plots showing the gating of CD8+Tim3+ T cells (upper panels) and TNF-α expression gated on these CD8+Tim3+ T cells (lower panels) from PBMCs isolated before (Pre) and 1-month (1 mo) after Y90-RE. Right panel shows the percentage of TNF-α expressing CD8+Tim-3+ T cells in sustained-responders (SRs) or non-responders (NRs) and transient-responders (TRs) to Y90-RE before (Pre) and after (1-6 mo) therapy. B. Representative plots showing the gating on TNF-α expressing CD4+ T cells from PBMCs isolated before (Pre) or 1-month (1 mo) after Y90 therapy. Right panels show the percentage of TNF-α expressing CD4+ T cells. C. Representative plots showing the gating on CD14+ HLA-DR+ cells from PBMCs isolated before (Pre) and 3-months (3 mo) after Y90-RE. Right panel shows the percentage of CD14+HLADR+ antigen-presenting cells in SRs and NRs/TRs to Y90-RE before (Pre) and after (1 mo-6 mo) therapy. Graphical data represent the means±standard deviation. Data were were analyzed by paired Student's t-test (for pre versus 1 mo or 3 mo) or unpaired Student's t-test (for 3 mo SRs versus NRs/TRs). * P<0.05. **P<0.01. D. Density plots showing CD14 and HLA-DR expression from representative nodes, NODE 293 represents APCs enriched in TILs from post Y90 RE tumors. Red plot shows expression profile from the selected node and black shows that of all the nodes. Red and black lines represent the average expression levels of each marker. E. Representative plots show the gating of GB+CD56+ NK cells from pre- and 3 mo post Y90 RE. Right, graphs show percentages of GB+CD56+ NK cells pre and at various time points post-Y90 RE in sustained-responders (SRs) and non- or transient responders (NRs/TRs). Data shows means±SDs and were analyzed by unpaired Student's t-test. *p<0.05.
Figure 12:
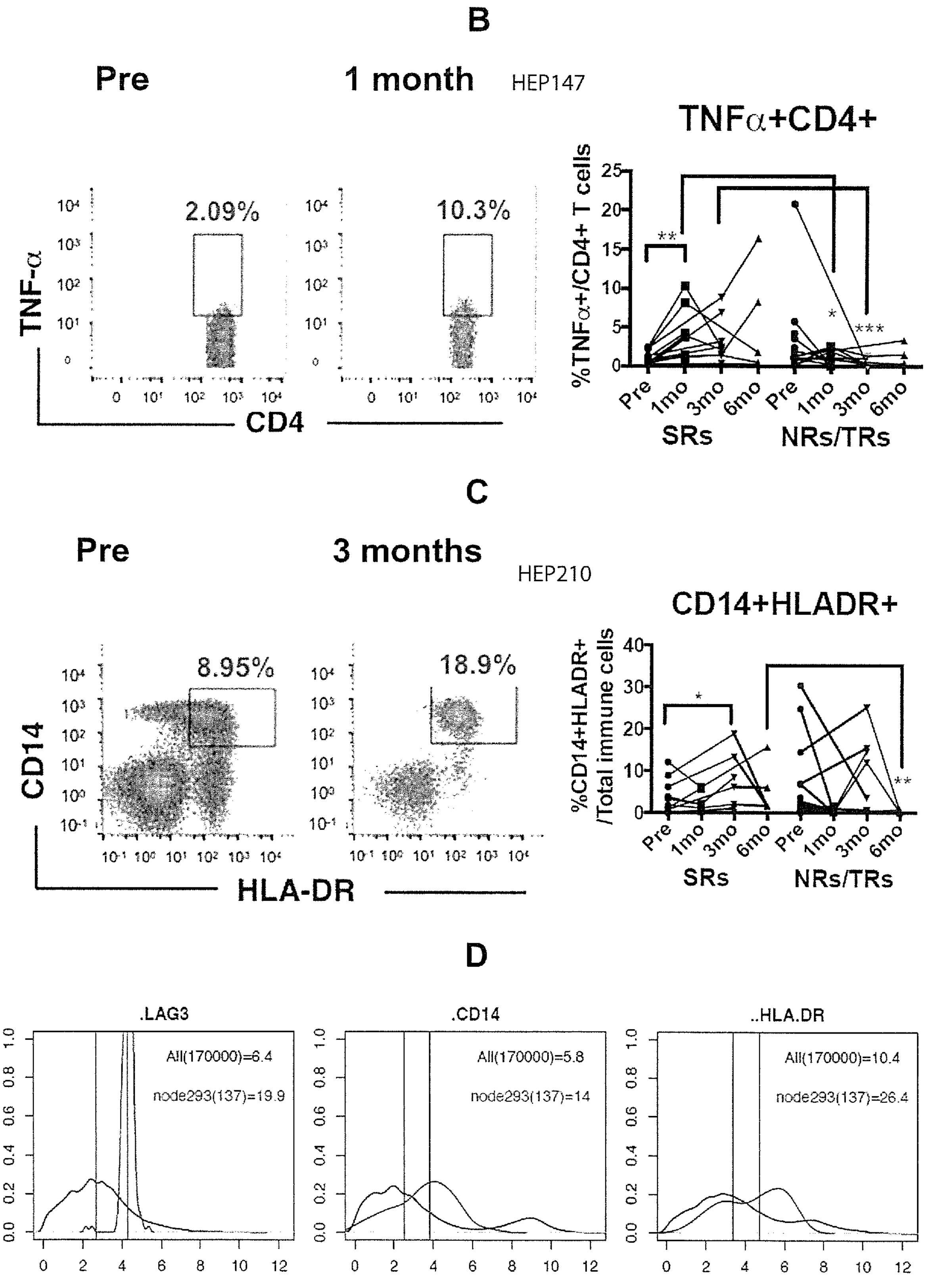
Figure 12:
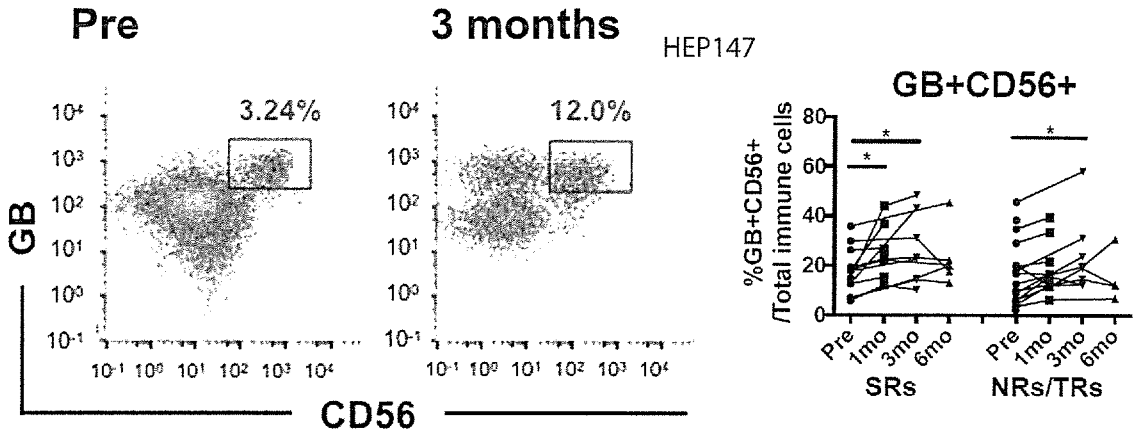

Analysis of PBMCs before and after Y90-RE by CyTOF allowed us to capture the systemic immune response triggered by the therapy and identify potential biomarkers to predict clinical outcome. The immune response that was first detected at 1-month post-Y90-RE was an increase in cytokine TNFα expression on CD8+ and CD4+ T cells, followed by increased APCs 3-months post-Y90-RE (FIG. 12). The high percentages of systemic CD8+ T cells and CD4+ CD45RO+ T cells that expressed PD-1 and Tim-3 before Y90-RE denoted the patients who went on to elicit a sustained response after therapy with an increase in time-to-tumour-progression of ≥6 months. The same immune subset, CD8+Tim-3+ T cells, was also one of the key subsets enriched in TILs in tumours from post-Y90-RE (FIG. 7).

Tim-3 is a marker of immune-cell exhaustion and is associated with the progression of various cancers, including HCC (Li, et al. Hepatology 56, 1342-1351 (2012)). Co-expression of PD-1 and Tim-3 can enhance T cell impairment and is also associated with tumour progression (Fourcade et al. J Exp Med 207, 2175-2186 (2010)). However, Tim-3 expression is also an indication of prior T cell activation (Hastings et al. Eur J Immunol 39, 2492-2501 (2009)), and indeed, the co-expression of Tim-3 and PD-1 on CD8+ T cells may indicate a prior immune response mounted towards tumour antigens. Another indication of heightened T cell activation was the co-expression of pro-inflammatory GB and TNFα on TILs or PBMCs in patients after Y90-RE (FIG. 7 and FIG. 12A). Targeting both Tim-3 and PD-1 pathways can reverse T cell exhaustion and restore anti-tumour immune responses in murine cancer models (Sakuishi, et al. J Exp Med 207, 2187-2194 (2010)). Given these data, it is postulate that sequential therapy involving Y90-RE followed by immunotherapy using check-point inhibitors against the PD-1/PD-L1 or Tim-3 pathways, particularly in the sustained-responders, may enhance the clinical response in HCC.

Figure 13:
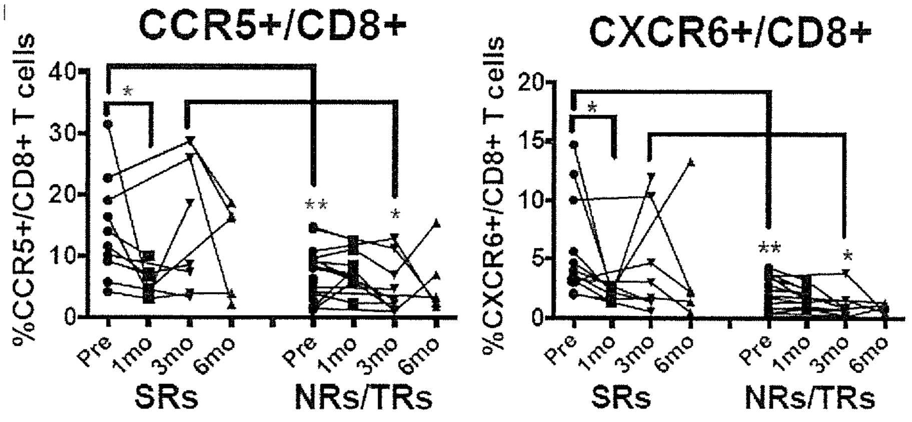
FIG. 13: Distinct immune subsets in sustained-responders (SRs) versus non-responders (NRs)/transient-responders (TRs) to Y90-RE. A Graphs show percentages of CXCR6+ or CCR5+ CD8+ T cells and CXCR6+ or CCR5+ CD8+ Tim-3 T cells in PBMCs isolated from SRs or NRs/TRs patients before (Pre) and at various time points (1, 3 and 6 mo) after Y90-RE. Graphical data represent the means±standard deviation and were analyzed by unpaired Student's t-test. *P<0.05 and **P<0.01. B 2D cellular illustration of PD-1 and Tim-3 on PBMCs isolated before (Pre) and at 3-months (3 mo) after Y90-RE from SRs or NRs/TRs patients. Images were generated using ACCENSE software.
Figure 13:
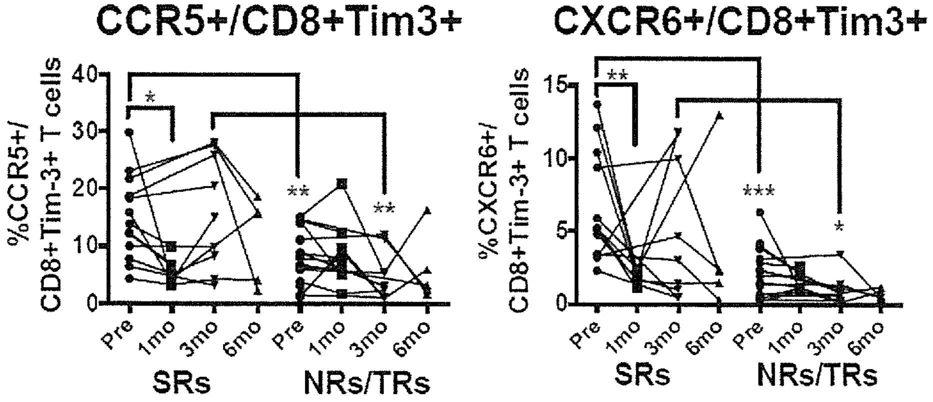

The co-expression of Tim-3 with the homing receptors CCR5 and CXCR6 on CD8+ T cells indicated their ability to home towards CCL5 and CXCL16 chemokines. The data demonstrated that CCR5+CD8+ and CXCR6+CD8+ or CCR5+/CXCR6+Tim-3+CD8+ T cells are other biomarkers of responders to Y90-RE (FIG. 13A).

Interestingly, NGS and qPCR indicated an up-regulation of CCL5 and CXCL16 in tumour microenvironment of post-Y90-RE (FIG. 11). These results imply that Y90-RE-induced chemokine expression is required for the recruitment of cytotoxic CD8+ T cells to tumour sites via CCL5 and CXCL16 pathways, and that this effect leads to a clinical response to Y90-RE (FIG. 11B).

Deep immunophenotyping and transcriptomic analysis demonstrated robust immune activation locally within the tumour microenvironment and systemically in the peripheral blood of HCC patients who showed sustained-response to Y90-RE. By this approach the immune activation was captured and predictive biomarkers were identified for sustained clinical response in the peripheral blood that may guide treatment choices for HCC patients.

Higher Expression of PD-1 and Tim-3 Identifies and Predicts Sustained Response to Y90_RE The systemic immune profiles of SRs versus NRs/TRs were compared at pre- and 3-months after Y90-RE. Distinct CD4+ T cells and CD8+ T-cell specific to SRs were observed. PD-1 and Tim-3 showed higher expression in SRs both pre- and 3-months after Y90-RE (FIG. 13B).

Figure 14:
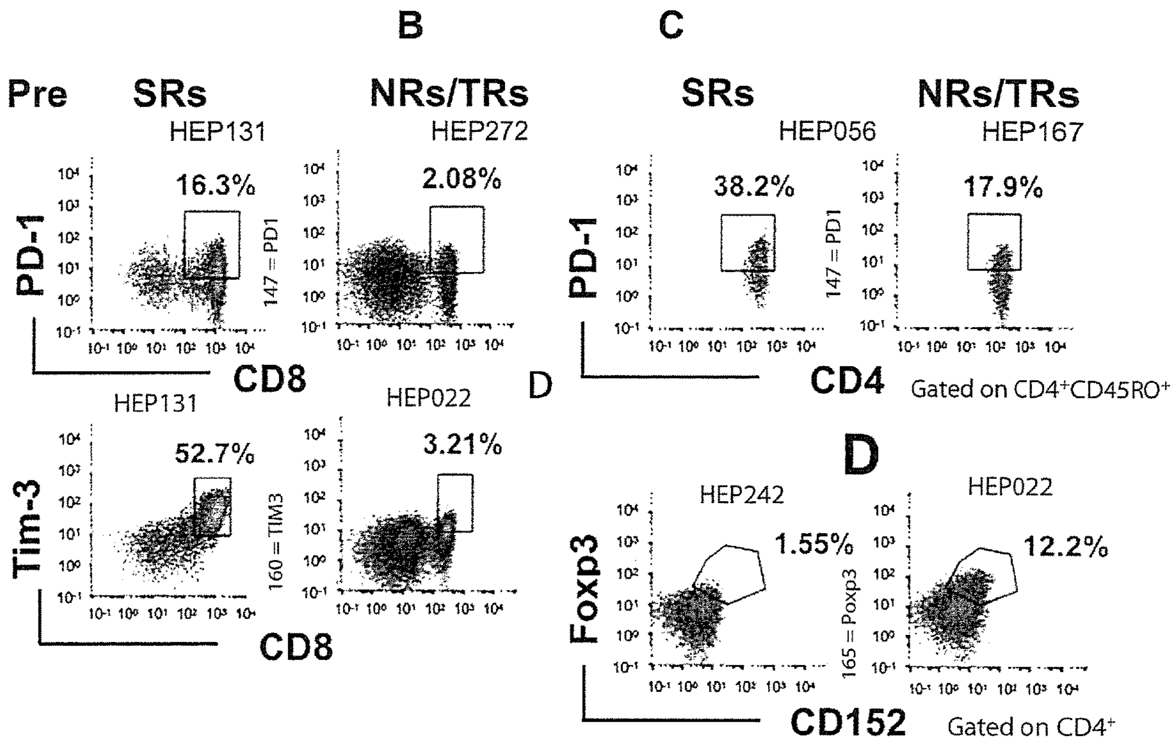
FIG. 14: Distinct immune subsets in sustained-responders (SRs) versus non-responders (NRs)/transient-responders (TRs) to Y90-RE. A Graphs show the percentages of the immune subsets: PD-1+CD8+ T cells, Tim3+CD8+ T cells, PD-1+CD45RO+CD4+ T cells and Foxp3+CD152+ Treg from SRs and NRs/TRs at various time points (1, 3 and 6 mo) after Y90-RE. B Representative plots showing percentages of PD-1+CD8+ T cells and Tim3+CD8+ T cells C. Representative plots showing percentages of PD1+CD4+ T cells (pre gated on CD4+CD45RO+ T cells), D Representative plots showing percentages of Foxp3+CD152+ Treg cells (pre gated on CD4+ T cells) B-D Immune subsets from pre-Y90 RE PBMCs in sustained responders (SRs) versus non or transient responders (NRs/TRs).

Validated by FlowJo manual gating, the higher percentages of PD-1- and Tim-3-expressing CD8+ T cells were shown in SRs at both time points (FIG. 14A and FIG. 14B). A higher percentage of PD-1+CD4+CD45RO+ T cells in SRs before and 3-months after therapy was also observed (FIG. 13A and FIG. 14C). Of note, Tim-3+CD8+ T cells remained higher in SRs up to 6-months after Y90-RE (FIG. 14A).

This apparent higher expression of exhaustion markers may indicate a higher level of T-cell activation that is specific to SRs both prior to and 3 or 6-months after the therapy. This may mediate in part the subsequent sustained response to Y90-RE. In contrast, the immune subsets enriched in the NRs/TRs at pre- or 3 months post-Y90-RE included CD4+Foxp3+CD152+ Treg (FIG. 14B and FIG. 14D); CD4+CD45RO+ T cells that do not express PD-1 and CD8+ T cells that do not express PD-1 or Tim-3.

T Cells from Sustained Responders of Y90-RE Express Specific Homing Receptors

Distinct differences in chemokine-receptor expression, namely CCR5 and CXCR6, were observed when comparing SRs with NRs/TRs pre- and 3-months post-Y90-RE (FIG.

Figure 15:
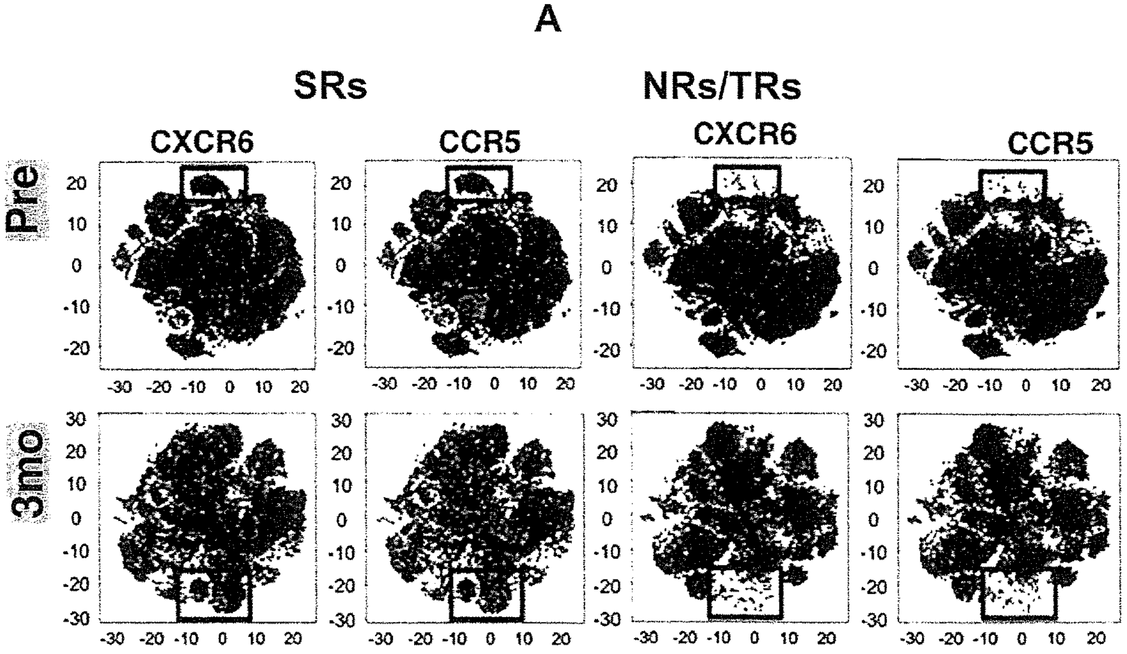
FIG. 15: Distinct immune subsets in sustained-responders (SRs) versus non-responders (NRs)/transient-responders (TRs) to Y90-RE. A 2D cellular illustration of CXCR6 and CCR5 on PBMCs isolated before (Pre) and 3-months (3 mo) after Y90-RE from SRs and NRs/TRs patients. Images were generated using ACCENSE software. B Representative plots showing percentages of CCR5+ or CXCR6+ CD8+ T cells. Immune subsets from pre-Y90 RE PBMCs in sustained responders (SRs) versus non- or transient responders (NRs/TRs).
Figure 15:
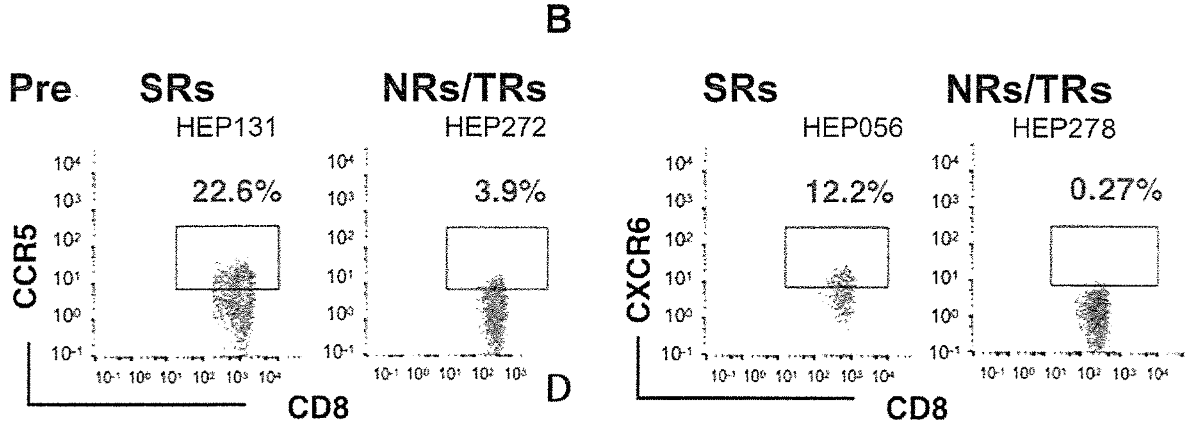

15A). FlowJo manual gating on all samples confirmed a significantly higher percentages of CCR5+CD8+ T cells and CXCR6+CD8+ T cells from SRs at both time points (FIG. 13A and FIG. 15B). Interestingly, the expression of CCR5 and CXCR6 was also significantly higher on the Tim-3+ CD8+ T-cell subsets that were enriched in SRs (FIG. 14A and FIG. 14B). The higher percentages of CCR5- and CXCR6-expressing CD8+ T cells is also consistent with the previous results showing the recruitment of activated CD8+ T cells to the tumour microenvironment upon Y90-RE (FIG. 11B). Furthermore, a drop in percentage of both CCR5 and CXCR6 on CD8+ T cells and CD8+Tim-3+ T-cells that was observed at 1-month post-Y90-RE further implicated the recruitment of activated T cells to the tumour site upon Y90-RE (FIG. 13A).

It should be further appreciated by the person skilled in the art that variations and combinations of features described above, not being alternatives or substitutes, may be combined to form yet further embodiments falling within the intended scope of the invention.

The invention claimed is:

1. An ex vivo method for the prognosis of response to treatment for a patient suffering from hepatocellular carcinoma, the method comprising:

creating a prediction model comprising;

Measuring expression of a plurality of immune markers on each cell in samples taken from a plurality of patients with hepatocellular carcinoma;

Evaluating a clinical response of the patients with hepatocellular carcinoma to treatment with radioembolization (RE) at 3 and/or 6 months after treatment wherein the clinical response is selected from sustained responder (SR) to RE, and transient/non-responder (TR/NR) to RE;

Determining if there is a correlation between each immune marker and either the clinical response SR, or the clinical response TR/NR;

Determining the probability of each immune marker one by one to positively affect the accuracy of the clinical response;

allocating a probability score using a weighted neighbourhood scheme, to each sample based on the number of immune markers that positively affects the accuracy of the clinical response;

measuring expression of at least one immune marker in a leukocyte sample taken from the patient with hepatocellular carcinoma;

allocating the same probability score obtained using the weighted neighbourhood scheme for each immune marker in the leukocyte sample taken from the patient suffering from hepatocellular carcinoma to classify the patient suffering from cancer as a predicted SR or predicted TR/NR, further classifying the patient leukocyte sample into (i) SR to RE or (ii) TR/NR to RE based on evaluating the expression of the at least one immune marker on each cell in the leukocyte sample; wherein a sample is classified as SR, when equal to or greater than 50% of the cells in the sample express the at least one marker, and a sample is classified as TR/NR when less than 50% of the cells express the at least one marker;

wherein the at least one immune marker comprises co-expression of CD8 and PD-1, or co-expression of CD8 and CCR5; or co-expression of CD8 and Tim-3, or co-expression of CD8 and CXCR6, or co-expression of CD8 and Tim-3 with CCR5, or expression of CD8 and Tim-3, with CXCR6 whereby patient predicted to be a SR is administered treatment with selective internal radiation therapy (SIRT) alone or SIRT in combination with immunotherapy and patient predicted to be TR/NR is administered treatment with trans-arterial chemoembolization (TACE), Sorafenib or immunotherapy alone.

2. The method of claim 1, wherein the leukocyte sample comprises a tumour infiltrating leukocyte sample.

3. The method of claim 1, wherein the leukocyte sample comprises a peripheral blood mononuclear cell (PBMC) sample.

4. The method of claim 1, wherein the sample is analysed using mass spectrometry by time of flight (CyTOF).

5. The method of claim 1, wherein the RE comprises Y90-RE.

6. The method of claim 1, wherein the probability score using the weighted neighbourhood scheme is allocated using a random forest prediction model.

7. The method of claim 1, wherein the plurality of immune markers include at least two immune markers selected from the group comprising CD14; CD3; CD19; CD45RO; HLA-DR; T-bet; CD28; PD-1; CD4; CD154; CD103; CXCR6; TNF-α, CD25; CD27; CD152; PD-L1; CD244; IL-10, LAG-3; Tim-3; CCR7; CD56; CXCR3; GITR; FoxP3; KI67; CD80; IFN-γ; IL-17A; EOMES; Granzyme B; CD37; CCR5; or CD69.

8. The method of claim 1, wherein an immune marker allocated with a higher probability score comprises the at least one immune marker or an additional at least one immune marker for evaluating the expression on each cell in the leukocyte sample.

* * * * *